US011351176B2

(12) United States Patent
Gold

(10) Patent No.: US 11,351,176 B2
(45) Date of Patent: Jun. 7, 2022

(54) COMBINATION THERAPY

(71) Applicant: MEI Pharma, Inc., San Diego, CA (US)

(72) Inventor: Daniel P. Gold, San Diego, CA (US)

(73) Assignee: MEI Pharma, Inc., San Diego, CA (US)

( * ) Notice: Subject to any disclaimer, the term of this patent is extended or adjusted under 35 U.S.C. 154(b) by 0 days.

(21) Appl. No.: 16/639,088

(22) PCT Filed: Aug. 14, 2018

(86) PCT No.: PCT/US2018/046742
§ 371 (c)(1),
(2) Date: Feb. 13, 2020

(87) PCT Pub. No.: WO2019/036489
PCT Pub. Date: Feb. 11, 2009

(65) Prior Publication Data
US 2020/0222415 A1    Jul. 16, 2020

Related U.S. Application Data

(60) Provisional application No. 62/545,427, filed on Aug. 14, 2017.

(51) Int. Cl.
*A61K 31/5377* (2006.01)
*A61P 35/00* (2006.01)
*C07K 16/28* (2006.01)
*A61K 9/00* (2006.01)

(52) U.S. Cl.
CPC .......... *A61K 31/5377* (2013.01); *A61P 35/00* (2018.01); *C07K 16/2887* (2013.01); *A61K 9/0019* (2013.01); *A61K 9/0053* (2013.01)

(58) Field of Classification Search
CPC ................................................ A61K 31/5377
See application file for complete search history.

(56) References Cited

U.S. PATENT DOCUMENTS

| | | | |
|---|---|---|---|
| 5,597,854 | A | 1/1997 | Birbaum et al. |
| 5,750,292 | A | 5/1998 | Sato et al. |
| 6,251,900 | B1 | 6/2001 | Kawashima et al. |
| 7,071,189 | B2 | 7/2006 | Kawashima et al. |
| 7,153,853 | B2 | 12/2006 | Kawashima et al. |
| 7,307,077 | B2 | 12/2007 | Kawashima et al. |
| 7,745,485 | B2 | 6/2010 | Durden |
| 8,486,939 | B2 | 7/2013 | Rewcastle et al. |
| 8,912,180 | B2 | 12/2014 | Takahashi et al. |
| 9,056,852 | B2 | 6/2015 | Brown et al. |
| 9,499,474 | B2 | 11/2016 | Kaufhold et al. |
| 10,064,868 | B2 | 9/2018 | Brown et al. |
| 10,335,415 | B2 | 7/2019 | Brown et al. |
| 10,603,324 | B2 | 3/2020 | Brown et al. |
| 2004/0002424 | A1 | 1/2004 | Minn et al. |
| 2007/0244110 | A1 | 10/2007 | Yaguchi et al. |
| 2008/0113987 | A1 | 5/2008 | Haruta et al. |
| 2008/0221103 | A1 | 9/2008 | Sharma et al. |
| 2008/0287431 | A1 | 11/2008 | Kawashima et al. |
| 2009/0192176 | A1 | 7/2009 | Zask et al. |
| 2009/0233926 | A1 | 9/2009 | Butterworth et al. |
| 2009/0270390 | A1 | 10/2009 | Butterworth et al. |
| 2009/0312319 | A1 | 12/2009 | Ren et al. |
| 2009/0325954 | A1 | 12/2009 | Butterworth et al. |
| 2010/0022534 | A1 | 1/2010 | Butterworth et al. |
| 2010/0202963 | A1 | 8/2010 | Gallatin et al. |
| 2011/0009405 | A1 | 1/2011 | Rewcastle et al. |
| 2012/0165309 | A1 | 6/2012 | Takahashi et al. |
| 2012/0252802 | A1 | 10/2012 | Brown et al. |
| 2013/0150364 | A1 | 6/2013 | Takahashi et al. |
| 2014/0079686 | A1 | 3/2014 | Barman et al. |
| 2014/0088103 | A1 | 3/2014 | Brown et al. |
| 2015/0265625 | A1 | 9/2015 | Brown et al. |
| 2016/0193211 | A1 | 7/2016 | Lavitrano et al. |
| 2017/0136014 | A1 | 5/2017 | Hamdy et al. |
| 2017/0231995 | A1 | 8/2017 | Hamdy et al. |
| 2017/0266191 | A1 | 9/2017 | Hamdy et al. |
| 2017/0349594 | A1 | 12/2017 | Kim et al. |
| 2018/0250298 | A1 | 9/2018 | Hamdy et al. |
| 2020/0197403 | A1 | 6/2020 | Gold |
| 2020/0316080 | A1 | 10/2020 | Brown et al. |
| 2021/0000838 | A1 | 1/2021 | Gold |
| 2021/0196725 | A1 | 7/2021 | Gold |

FOREIGN PATENT DOCUMENTS

| | | |
|---|---|---|
| CA | 2808435 A1 | 2/2012 |
| EP | 0711804 A2 | 5/1996 |
| EP | 1020462 A1 | 7/2000 |
| EP | 1389617 A1 | 2/2004 |
| EP | 1864665 A1 | 12/2007 |

(Continued)

OTHER PUBLICATIONS

McMahon et al. (2000).*
Pinedo et al. (2000).*
Barber et al.: PI3Kgamma inhibition blocks glomerulonephritis and extends lifespan in a mouse model of systemic lupus, Nat. Med. 2005, 11:933-935.
Bedingfield et al.: Structure activity relationships for a series of phenylglyceine derivatives acting at mGluRs, British Journal of Pharmacology, 1995, 116:3323-3329.
Berrie. Phosphoinositide 3-kinase inhibition in cancer treatment, Exp.Opin. Invest. Drugs 2001, 10:1085-1098.
Billottet et al.: A selective inhibitor of the p110delta isoform of PI 3-kinase inhibits AML cell proliferation and survival and increases the cytotoxic effects of VP16, Oncogene 2006, 25:6648-6659.
Byrn et al. Chapter II: Hydrates and Solvates. Solid-State Chemistry of Drugs, 2nd edition pp. 233-248 (1999).

(Continued)

*Primary Examiner* — Paul V Ward
(74) *Attorney, Agent, or Firm* — Wilson Sonsini Goodrich & Rosati

(57) ABSTRACT

Provided herein are methods of treating diseases, such as cancer, using a combination therapy. In certain embodiments, the methods comprise administering an effective amount of a phosphoinositide-3-kinase (PI3K) inhibitor and an effective amount of a CD20 inhibitor to a patient.

19 Claims, No Drawings

(56) References Cited

FOREIGN PATENT DOCUMENTS

| | | |
|---|---|---|
| EP | 2050749 A1 | 4/2009 |
| EP | 2397479 A1 | 12/2011 |
| JP | H11174638 A | 7/1999 |
| TW | 201105662 A | 2/2011 |
| WO | WO-9905138 A1 | 2/1999 |
| WO | WO-0181346 A2 | 11/2001 |
| WO | WO-02088112 A1 | 11/2002 |
| WO | WO-03077921 A1 | 9/2003 |
| WO | WO-03078423 A1 | 9/2003 |
| WO | WO-03078426 A1 | 9/2003 |
| WO | WO-03078427 A1 | 9/2003 |
| WO | WO-03097862 A1 | 11/2003 |
| WO | WO-2004037812 A1 | 5/2004 |
| WO | WO-2004048365 A1 | 6/2004 |
| WO | WO-2005028467 A1 | 3/2005 |
| WO | WO-2005066156 A1 | 7/2005 |
| WO | WO-2005095389 A1 | 10/2005 |
| WO | WO-2006021881 A2 | 3/2006 |
| WO | WO-2006053109 A1 | 5/2006 |
| WO | WO-2006053227 A1 | 5/2006 |
| WO | WO-2006095906 A1 | 9/2006 |
| WO | WO-2006122806 A2 | 11/2006 |
| WO | WO-2007066099 A1 | 6/2007 |
| WO | WO-2007066103 A1 | 6/2007 |
| WO | WO-2007084786 A1 | 7/2007 |
| WO | WO-2007127175 A2 | 11/2007 |
| WO | WO-2007127183 A1 | 11/2007 |
| WO | WO-2008018426 A1 | 2/2008 |
| WO | WO-2008032027 A1 | 3/2008 |
| WO | WO-2008032028 A1 | 3/2008 |
| WO | WO-2008032033 A1 | 3/2008 |
| WO | WO-2008032036 A1 | 3/2008 |
| WO | WO-2008032041 A1 | 3/2008 |
| WO | WO-2008032060 A1 | 3/2008 |
| WO | WO-2008032064 A1 | 3/2008 |
| WO | WO-2008032072 A1 | 3/2008 |
| WO | WO-2008032077 A1 | 3/2008 |
| WO | WO-2008032086 A1 | 3/2008 |
| WO | WO-2008032089 A1 | 3/2008 |
| WO | WO-2008032091 A1 | 3/2008 |
| WO | WO-2008098058 A1 | 8/2008 |
| WO | WO-2008115974 A2 | 9/2008 |
| WO | WO-2008116129 A2 | 9/2008 |
| WO | WO-2008154026 A1 | 12/2008 |
| WO | WO-2009007751 A2 | 1/2009 |
| WO | WO-2009045174 A1 | 4/2009 |
| WO | WO-2009045175 A1 | 4/2009 |
| WO | WO-2009066775 A1 | 5/2009 |
| WO | WO-2009093981 A1 | 7/2009 |
| WO | WO-2009097490 A1 | 8/2009 |
| WO | WO-2009099163 A1 | 8/2009 |
| WO | WO-2009120094 A2 | 10/2009 |
| WO | WO-2009143313 A1 | 11/2009 |
| WO | WO-2009143317 A1 | 11/2009 |
| WO | WO-2009157880 A1 | 12/2009 |
| WO | WO-2010005558 A2 | 1/2010 |
| WO | WO-2010048149 A2 | 4/2010 |
| WO | WO-2010052569 A2 | 5/2010 |
| WO | WO-2010092962 A1 | 8/2010 |
| WO | WO-2010110685 A2 | 9/2010 |
| WO | WO-2010110686 A1 | 9/2010 |
| WO | WO-2010136491 A1 | 12/2010 |
| WO | WO-2010138589 A1 | 12/2010 |
| WO | WO-2010151735 A2 | 12/2010 |
| WO | WO-2010151737 A2 | 12/2010 |
| WO | WO-2010151740 A2 | 12/2010 |
| WO | WO-2010151791 A2 | 12/2010 |
| WO | WO-2011005119 A1 | 1/2011 |
| WO | WO-2012020762 A1 | 2/2012 |
| WO | WO-2012129562 A2 | 9/2012 |
| WO | WO-2012135160 A1 | 10/2012 |
| WO | WO-2012135166 A1 | 10/2012 |
| WO | WO-2012135175 A1 | 10/2012 |
| WO | WO-2012178123 A1 | 12/2012 |
| WO | WO-2012178124 A1 | 12/2012 |
| WO | WO-2012178125 A1 | 12/2012 |
| WO | WO-2013006408 A1 | 1/2013 |
| WO | WO-2013068075 A1 | 5/2013 |
| WO | WO-2014025960 A1 | 2/2014 |
| WO | WO-2014055647 A1 | 4/2014 |
| WO | WO-2014141129 A2 | 9/2014 |
| WO | WO-2015125085 A1 | 8/2015 |
| WO | WO-2016049214 A1 | 3/2016 |
| WO | WO-2016105118 A2 | 6/2016 |
| WO | WO-2017015267 A1 | 1/2017 |
| WO | WO-2017035234 A1 | 3/2017 |
| WO | WO-2017066705 A1 | 4/2017 |
| WO | WO-2018017708 A1 | 1/2018 |
| WO | WO-2018053437 A1 | 3/2018 |
| WO | WO-2018060833 A1 | 4/2018 |
| WO | WO-2019036489 A1 | 2/2019 |
| WO | WO-2020036997 A1 | 2/2020 |
| WO | WO-2020036999 A1 | 2/2020 |
| WO | WO-2020132563 A1 | 6/2020 |

OTHER PUBLICATIONS

Camps et al.: Blockade of PI3Kgamma suppresses joint inflammation and damage in mouse models of rheumatoid arthritis, Nat. Med. 2005, 11:936-943.
Foukas and Sheperd. Phosphoinositide 3-kinase: the protein kinase that time forgot Biochem. Soc. Trans. 2004, 32:330-331.
Fry. Phosphoinositide 3-kinase signaling in breast cancer: how big a role might it play? Breast Cancer Res. 2001, 3:304-312.
Fry. Structure, regulation and function of phosphoinositide 3-kinases, Biochem. Biophys. Acta 1994, 1226:237-268.
Furman et al.: Idelalisib and Rituximab in Relapsed Chronic Lymphocytic Leukemia; New England Journal of Medicine; vol. 370(11); pp. 997-1007 (2014).
Golub et al.: Molecular classification of cancer: Class discovery and class prediction by gene expression monitoring. Science, 286:531-537, 1999.
Gymnopoulos et al.: Rare cancer-specific mutations in PIK3CA show gain of function, Proc. Natl. Acad. Sci., 2007, 104:5569-5574.
Hayakawa et al.: Synthesis and biological evaluation of imidazo[1,2-a]pyridine derivatives as novel PI3 kinase p110alpha inhibitors, Bioorg. Med. Chem. 2007, 15:403-412.
Hayakawa et al.: Synthesis and biological evaluation of pyrido[3',2':4,5]furo[3,2-d]pyrimidine derivatives as novel PI3 kinase p110alpha inhibitors, Bioorg. Med. Chem. Lett. 2007, 17:2438-2442.
Hayakawa et al.: Synthesis and biological evaluation of sulfonylhydrazone-substituted imidazo[1,2-a]pyridines as novel PI3 kinase p110alpha inhibitors, Bioorg. Med. Chem. 2007, 15:5837-5844.
Hu et al.: Inhibition of phosphatidylinositol 3'-kinase increases efficacy of paclitaxel in in vitro and in vivo ovarian cancer models, Cancer Res. 2002, 62:1087-1092.
Huang et al.: The structure of a human p110alpha/p85alpha complex elucidates the effects of oncogenic PI3Kalpha mutations, Science 2007, 318:1744-1748.
Ikenoue et al.: Functional analysis of PIK3CA gene mutations in human colorectal cancer, Cancer Res. 2005, 65:4562-4567.
International Application No. PCT/US2017/052086 International Search Report and Written Opinion dated Mar. 22, 2018.
International Application No. PCT/US2018/046742 International Search Report and Written Opinion dated Oct. 24, 2018.
International Application No. PCT/US2019/023172 International Search Report and Written Opinion dated Jun. 6, 2019.
Ito et al.: Therapeutic potential of phosphatidylinositol 3-kinase inhibitors in inflammatory respiratory disease, J. Pharm. Exp. Ther. 2007, 321:1-8.
Jackson et al.: PI 3-kinase p110beta: a new target for antithrombotic therapy, Nat. Med. 2005, 11:507-514.
Jaworska and Nikolova. SAR applicability domain. Review of methods for assessing the applicability domains of SARS and QSARS. Paper 4: SAR applicability domain. 9 pages, 2004.

(56) References Cited

OTHER PUBLICATIONS

Kang et al.: Phosphatidylinositol 3-kinase mutations identified in human cancer are oncogenic, Proc. Natl. Acad. Sci. USA 2005, 102:802-807.
Knight et al.: A pharmacological map of the PI3-K family defines a role for p110alpha in insulin signaling, Cell 2006, 125:733-747.
Kong et al.: ZSTK474 is an ATP-competitive inhibitor of class I phosphatidylinositol 3 kinase isoforms, Cancer Sci. 2007, 98:1638-1642.
Lala and Orucevic. Role of nitric oxide in tumor progression: Lessons from experimental tumors. Cancer and Metastasis Reviews, 17(1):91-106, 1998.
Lanni et al.: Design and synthesis of phenethyl benzo[1,4]oxazine-3-ones as potent inhibitors of PI3Kinasegamma, Bioorg. Med. Chem. Lett. 2007, 17:756-760.
Liew et al.: SVM model for virtual screening of Lck inhibitors, J. Chem. Inf. Model. 2009, 49:877-885.
Maira et al.: Identification and characterization of NVP-BEZ235, a new orally available dual phosphatidylinositol 3-kinase/mammalian target of rapamycin inhibitor with potent in vivo antitumor activity, Mol. Cancer Ther. 2008, 7:1851-1863.
Marshall et al.: Estimation of radiation-induced interphase cell death in cultures of human tumor material and in cell lines, Oncol. Res. 2004, 14:297-304.
Matsuno et al.: Synthesis and antitumor activity of benzimidazolyl-1,3,5-triazine and benzimidazolylpyrimidine derivatives, Chem. Pharm. Bull. 2000, 48:1778-1781.
Miled et al.: Mechanism of two classes of cancer mutations in the phosphoinositide 3-kinase catalytic subunit, Science 2007, 317:239-242.
PCT/NZ2010_000139 International Search Report and Written Opinion dated Jan. 13, 2011.
PCT/JP2011/068169 International Search Report dated Aug. 26, 2011 (w/English translation).
PCT/US2012/030653 International Search Report dated Jul. 5, 2012.
PCT/US2012/030664 International Search Report dated Jul. 5, 2012.
PCT/US2013/063067 International Search Report dated Dec. 6, 2013.
PCT/US2019/046408 International Search Report and Written Opinion dated Oct. 24, 2019.
PCT/US2019/046411 International Search Report and Written Opinion dated Oct. 29, 2019.
PUBCHEM-SID: 340590222; pp. 1-4; p. 2; Aug. 23, 2017 (https://pubchem.ncbi.nlm.nih.gov/substance/340590222).
Raynaud et al.: Pharmacologic characterization of a potent inhibitor of class I phosphatidylinositide 3-kinases, Cancer Res. 2007, 67: 5840-5850.
Rommel et al.: PI3K delta and PI3K gamma: partners in crime in inflammation in rheumatoid arthritis and beyond? Nat. Rev. Immunol. 2007, 7:191-201.
Sabat et al.: The development of 2-benzimidazole substituted pyrimidine based inhibitors of lymphocyte specific kinase (Lek), Bioorg. Med. Che. Lett. 2006, 16:5973-5977.
Samuels et al.: High frequency of mutations of the PIK3CA gene in human cancers, Science 2004, 304:554.
Semba et al.: The in vitro and in vivo effects of 2-(4-morpholinyl)-8-phenyl-chromone (LY294002), a specific inhibitor of phosphatidylinositol 3'-kinase, in human colon cancer cells, Clin. Cancer Res. 2002, 8:1957-1963.
Shepherd. Mechanisms regulating phosphoinositide 3-kinase signalling in insulin-sensitive tissues, Acta Physiol. Scand. 2005, 183:3-12.
Stauffer et al.: Blocking the PI3K/PKB pathway in tumor cells, Curr. Med. Chem. Anticancer Agents 2005, 5:449-462.
Stephens et al.: Phosphoinositide 3-kinases as drug targets in cancer, Curr. Opin. Pharmacol. 2005, 5, 357-365.
Stirdivant et al.: Cloning and mutagenesis of the p110 alpha subunit of human phosphoinositide 3'-hydroxykinase, Bioorg. Med. Chem. 1997, 5:65-74.
U.S. Appl. No. 14/729,700 Office Action dated Feb. 7, 2017.
U.S. Appl. No. 14/729,700 Office Action dated Oct. 17, 2017.
U.S. Appl. No. 16/334,303 Restriction Requirement dated Dec. 5, 2019.
U.S. Appl. No. 16/389,371 Notice of Allowance dated Nov. 15, 2019.
Vanhaesebroeck and Waterfield. Signaling by distinct classes of phosphoinositide 3-kinases, Exp. Cell. Res. 1999, 253:239-254.
Volinia et al.: Molecular cloning, cDNA sequence, and chromosomal localization of the human phosphatidylinositol 3-kinase p110 alpha (PIK3CA) gene, Genomics 1994, 24:472-477.
Voskoglou-Nomikos et al.: Clinical predictive value of the in Vitro cell line, human xenograft, and mouse allograft preclinical cancer models. Clinical Cancer Research, 9:4227-4239, 2003.
Walker et al.: Structural determinants of phosphoinositide 3-kinase inhibition by wortmannin, LY294002, quercetin, myricetin, and staurosporine, Mol .Cell. 2000, 6:909-919.
Wipf et al.: Synthesis and biological evaluation of synthetic viridins derived from C(20)-heteroalkylation of the steroidal PI-3-kinase inhibitor wortmannin, Org. Biomol. Chem., 2004, 2:1911-1920.
Yaguchi et al.: Antitumor activity of ZSTK474, a new phosphatidylinositol 3-kinase inhibitor, J. Natl. Cancer Inst. 2006, 98:545-556.
Zask et al.: Synthesis and structure-activity relationships of ring-opened 17-hydroxywortmannins: potent phosphoinositide 3-kinase inhibitors with improved properties and anticancer efficacy, J. Med. Chem., 2008, 51:1319-1323.
Zhu et al.: Pegylated wortmannin and 17-hydroxywortmannin conjugates as phosphoinositide 3-kinase inhibitors active in human tumor xenograft models, J. Med. Chem., 2006, 49:1373-1378.
De Vos et al.: Combinations of idelalisib with rituximab and/or bendamustine in patients with recurrent indolent non-Hodgkin lymphoma. Blood Advances. 1(2):122-131 (2016).
Lichtman: Battling the Hematological Malignancies: The 200 Years' War. The Oncologist. 13:126-138 (2008).
Mei Pharma et al.: MEI Pharma Presents Updated Clinical Data from the ME-401 Monotherapy and in Combination with Rituximab Phase 1b study in Patients with Follicular Lymphoma at the 2019 American Society of Clinical Oncology (ASCO) Annual Meeting. 2019.
O'Farrell: Preclinical Characterization of PWT143, a Novel Selective and potent Phosphatidylinositol 3-kinase Delta (PI3K delta) Inhibitor with Ex-Vivo Activity in Hematologic Malignancies. Blood. American Society of Hematoloty. Title; Abstract (2012).
PCT/US2019/068050 International Search Report and Written Opinion dated Mar. 31, 2020.
Salles et al.: Efficacy and safety of idelalisib in patients with relapsed, rituximab-and alkylating agent-refractory follicular lympohoma: a subgroup analysis of a phase 2 study. Haematologica. 102:3158(2017).
U.S. Appl. No. 16/789,954 Final Office Action dated Sep. 27, 2021.

\* cited by examiner

COMBINATION THERAPY

CROSS-REFERENCE

This application is a national stage entry of PCT/US2018/046742, filed on Aug. 14, 2018, and claims benefit of U.S. Patent Application No. 62/545,427, filed on Aug. 14, 2017, which are all hereby incorporated by reference in their entirety.

BACKGROUND OF THE INVENTION

Phosphoinositide-3-kinases (PI3Ks) play a variety of roles in normal tissue physiology, with p110α having a specific role in cancer growth, p110β in thrombus formation mediated by integrin $α_{IIb}β$, and p110γ, in inflammation, rheumatoid arthritis, and other chronic inflammation states. Inhibitors of PI3K have therapeutic potential in the treatment of various proliferative diseases, including cancer.

SUMMARY OF THE INVENTION

Disclosed herein is a method for treating or preventing a disease comprising administering:
(i) an effective amount of a compound of Formula (I);

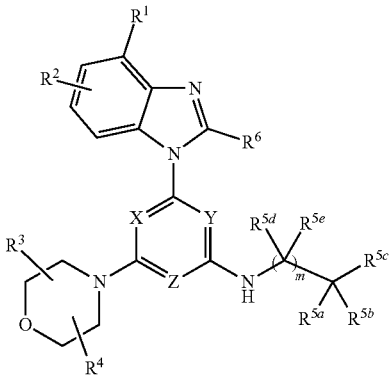

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2$ $R^{1a}$, —S(C)N$R^{1b}R^{1c}$, or —S(O)$_2$N$R^{1b}R^{1c}$;

wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O) $R^{1a}$, —OC(O)O$R^{1a}$, —OC(O)N$R^{1b}R^{1c}$, —OC(=N$R^{1a}$) N$R^{1b}R^{1c}$, —OS(O)$R^{1a}$, —OS(O)$_2R^{1a}$, —OS(O) N$R^{1b}R^{1c}$, —OS(O)$_2$N$R^{1b}R^{1c}$, —N$R^{1b}R^{1c}$, —N$R^{1a}$C(O) $R^{1d}$, —N$R^{1a}$C(O)O$R^{1d}$, —N$R^{1a}$C(O)N$R^{1b}R^{1c}$, —N$R^{1a}$C (=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O) N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$) N$R^{1b}R^{1c}$, —OS(O)$R^{1a}$, —OS(O)$_2R^{1a}$, —OS(O) N$R^{1b}R^{1c}$, —OS(O)$_2$N$R^{1b}R^{1c}$, —N$R^{1b}R^{1c}$, —N$R^{1a}$C(O) $R^{1d}$, —N$R^{1a}$C(O)O$R^{1d}$, —N$R^{1a}$C(O)N$R^{1b}R^{1c}$, —N$R^{1a}$C (=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$ N$R^{1b}R^{1c}$;

$R^{5c}$ is —$(CR^{5f}R^{5g})_n$—$(C_{6-14}$ aryl) or —$(CR^{5f}R^{5g})_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$) N$R^{1b}R^{1c}$, —O$R^{1a}$, —OC(O)$R^{1a}$, —OC(O)O$R^{1a}$, —OC (O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O) N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$) N$R^{1b}R^{1c}$, —O$R^{1a}$, —OC(O)$R^{1a}$, —OC(O)O$R^{1a}$, —OC (O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O) N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$; or —S(O)$_2$N$R^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in $R^1$, $R^2$, $R^3$, $R^4$, $R^6$, $R^X$, $R^{1a}$, $R^{1b}$, $R^{1c}$, $R^{1d}$, $R^{5a}$, $R^{5b}$, $R^{5c}$, $R^{5d}$, $R^{5e}$, $R^{5f}$, and $R^{5g}$ is optionally substituted with one, two, three, four, or five substituents Q, wherein each substituent Q is independently selected from (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one, two, three, or four, substituents $Q^a$; and (c) —C(O)$R^a$, —C(O)O$R^a$, —C(O)NR$^b$R$^c$, —C(NR$^a$)NR$^b$R$^c$, —O$R^a$, —OC(O)$R^a$, —OC(O)O$R^a$, —OC(O)NR$^b$R$^c$, —OC(=NR$^a$)NR$^b$R$^c$, —OS(O)$R^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one, two, three, or four, substituents $Q^a$; or (iii) R$^b$ and R$^c$ together with the N atom to which they are attached form heterocyclyl, which is further optionally substituted with one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl;

wherein two substituents Q that are adjacent to each other optionally form a $C_{3-10}$ cycloalkenyl, $C_{6-14}$ aryl, heteroaryl, or heterocyclyl, each optionally substituted with one, two, three, or four substituents $Q^a$; and (ii) an effective amount of a CD20 inhibitor to a patient in need thereof.

In some embodiments, $R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —S(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1b}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

In some embodiments, $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

In some embodiments, $R^{5a}$ and $R^{5b}$ are each methyl, optionally substituted with one, two or three halos. In some embodiments, n is 1. In some embodiments, n is 1 and $R^{5f}$ and $R^{5g}$ are each hydrogen. In some embodiments, n is 0. In some embodiments, m is 0.

In some embodiments, the compound of Formula (I) is of Formula (XI):

Formula (XI)

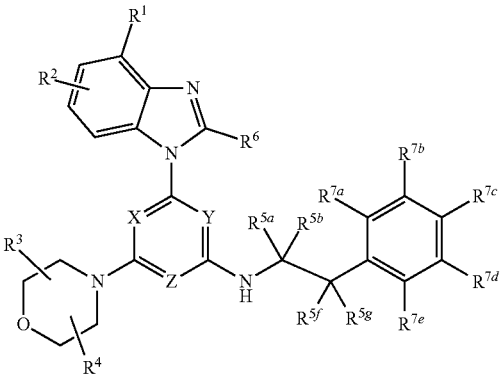

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, or —S(O)$_2$NR$^b$R$^c$;

or two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one, two, three, or four substituents $Q^a$.

In some embodiments, the compound of Formula (I) is Compound A35:

Compound A35

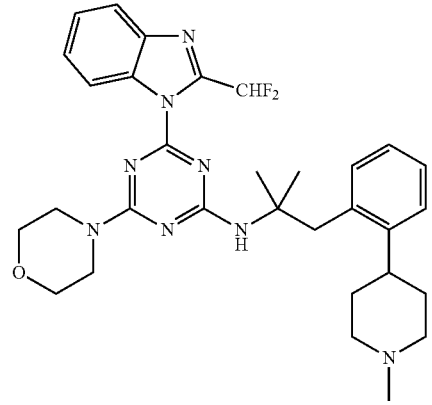

or an isotopic variant thereof, a pharmaceutically acceptable salt, solvate, hydrate, or prodrug thereof.

In some embodiments, the compound of Formula (I) is Compound A36:

Compound A36

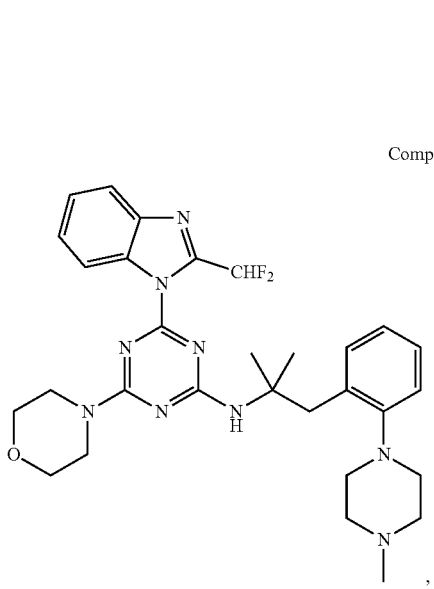

or an isotopic variant thereof, a pharmaceutically acceptable salt, solvate, hydrate, or prodrug thereof.

In some embodiments, the compound of Formula (I) is Compound A68:

Compound A68

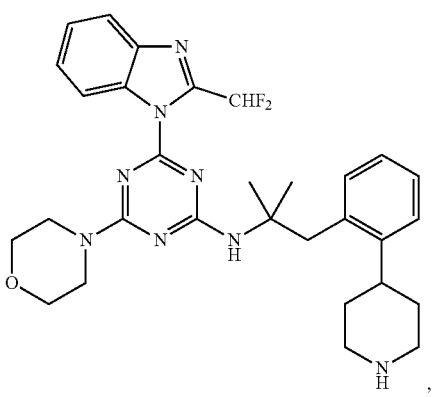

or an isotopic variant thereof, a pharmaceutically acceptable salt, solvate, hydrate, or prodrug thereof.

In some embodiments, the compound of Formula (I) is Compound A70:

Compound A70

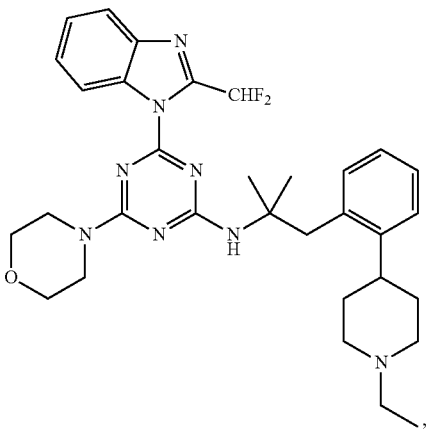

or an isotopic variant thereof, a pharmaceutically acceptable salt, solvate, hydrate, or prodrug thereof.

In some embodiments, the compound of Formula (I) is Compound A37:

Compound A37

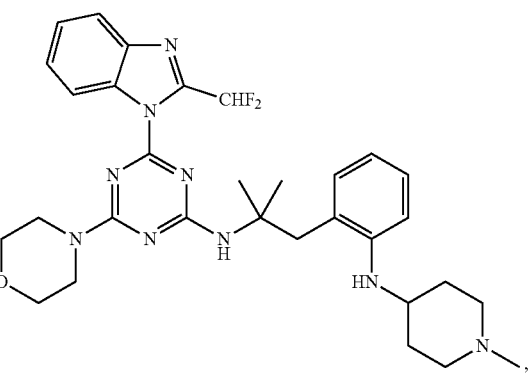

or an isotopic variant thereof, a pharmaceutically acceptable salt, solvate, hydrate, or prodrug thereof.

In some embodiments, the compound of Formula (I) is Compound A38:

Compound A38

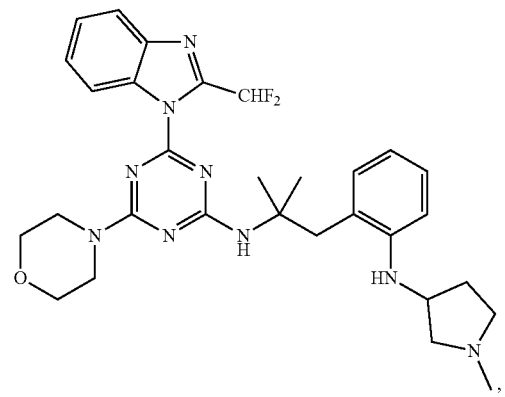

or an isotopic variant thereof, a pharmaceutically acceptable salt, solvate, hydrate, or prodrug thereof.

In some embodiments, the compound of Formula (I) is Compound A41:

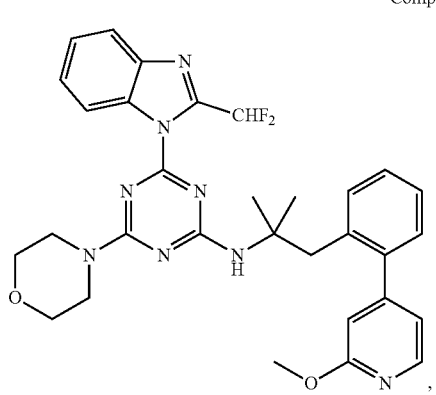

Compound A41 or an isotopic variant thereof, a pharmaceutically acceptable salt, solvate, hydrate, or prodrug thereof.

In some embodiments, the compound of Formula (I) is Compound A42:

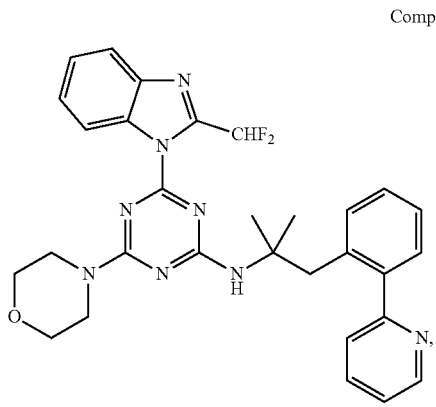

Compound A42 or an isotopic variant thereof, a pharmaceutically acceptable salt, solvate, hydrate, or prodrug thereof.

In some embodiments, the compound of Formula (I) is Compound A43:

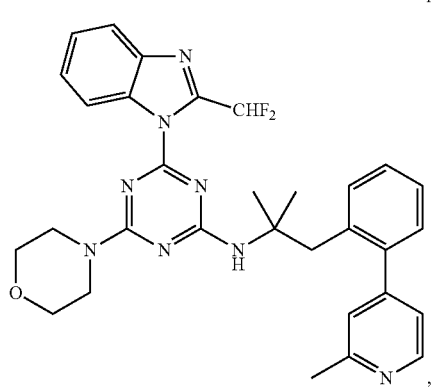

Compound A43 or an isotopic variant thereof, a pharmaceutically acceptable salt, solvate, hydrate, or prodrug thereof.

In some embodiments, the compound of Formula (I) is Compound A44:

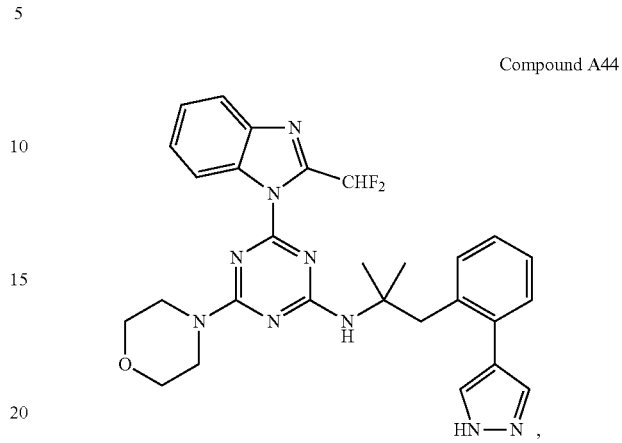

Compound A44 or an isotopic variant thereof, a pharmaceutically acceptable salt, solvate, hydrate, or prodrug thereof.

In some embodiments, the CD20 inhibitor is ofatumumab, obinutuzumab, rituximab, ocaratuzumab, ocrelizumab, tositumomab, ibritumomab tiuxetan, tisotumab vedotin, ublituximab, TRU-015, veltuzumab, BTCT4465A (RG7828), EDC9, MT-3724, or a variant or biosimilar thereof, or combinations thereof.

In some embodiments, the disease being treated is cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Described herein are pharmaceutical compositions comprising a PI3K inhibitor and a CD20 inhibitor. In some instances, the pharmaceutical compositions described herein may be used for treating diseases or disorders associated with excessive cell proliferation, such as cancer. Also described herein are methods of treating the proliferative diseases and disorders with i) a PI3K inhibitor; and ii) a CD20 inhibitor.

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "therapeutically effective amount" or "effective amount" are meant to include the amount of a compound that, when administered, is sufficient to prevent development of, or alleviate to some extent, one or more of the symptoms of the disorder, disease, or condition being treated. The terms "therapeutically effective amount" or "effective amount" also refer to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st Edition, Lippincott Williams & Wilkins: Philadelphia, Pa., 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; *Pharmaceutical Preformulation and Formulation*, 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a disorder, disease, or condition. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a disorder, disease, or condition.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "PI3K" refers to a phosphoinositide 3-kinase or variant thereof, which is capable of phosphorylating the inositol ring of PI in the D-3 position. The term "PI3K variant" is intended to include proteins substantially homologous to a native PI3K, i.e., proteins having one or more naturally or non-naturally occurring amino acid deletions, insertions, or substitutions (e.g., PI3K derivatives, homologs, and fragments), as compared to the amino acid sequence of a native PI3K. The amino acid sequence of a PI3K variant is at least about 80% identical, at least about 90% identical, or at least about 95% identical to a native PI3K. Examples of PI3K include, but are not limited to, p110α, p110β, p110δ, p110γ, PI3K-C2α, PI3K-C2β, PI3K-C2γ, Vps34, mTOR, ATM, ATR, and DNA-PK. See, Fry, *Biochem. Biophys. Acta* 1994, 1226, 237-268; Vanhaesebroeck and Waterfield, *Exp. Cell. Res.* 1999, 253, 239-254; and Fry, *Breast Cancer Res.* 2001, 3, 304-312. PI3Ks are classified into at least four classes. Class I includes p110α, p110β, p110δ, and p110γ. Class II includes PI3K-C2α, PI3K-C2β, and PI3K-C2γ. Class III includes Vps34. Class IV includes mTOR, ATM, ATR, and DNA-PK. In certain embodiments, the PI3K is a Class I kinase. In certain embodiments, the PI3K is p110α, p110γ, p110δ, or p110γ. In certain embodiments, the PI3K is a variant of a Class I kinase. In certain embodiments, the PI3K is a p110α mutant. Examples of p110α mutants include, but are not limited to, R38H, G106V, K111N, K227E, N345K, C420R, P539R, E542K, E545A, E545G, E545K, Q546K, Q546P, E453Q, H710P, 1800L, T1025S, M10431, M1043V, H1047L, H1047R, and H1047Y (Ikenoue et al., *Cancer Res.* 2005, 65, 4562-4567; Gymnopoulos et al., *Proc. Natl. Acad Sci.*, 2007, 104, 5569-5574). In certain embodiments, the PI3K is a Class II kinase. In certain embodiments, the PI3K is PI3K-C2α, PI3K-C2β, or PI3K-C2γ. In certain embodiments, the PI3K is a Class III kinase. In certain embodiments, the PI3K is Vps34. In certain embodiments, the PI3K is a Class IV kinase. In certain embodiments, the PI3K is mTOR, ATM, ATR, or DNA-PK.

The term "CD20" refers to an activated-glycosylated phosphoprotein expressed on the surface of all B-cells beginning at the pro-B phase (CD45R+, CD117+) and progressively increasing in concentration until maturity. The CD20 in humans is encoded by the MS4A1 gene. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes a B-lymphocyte surface molecule that plays a role in the development and differentiation of B-cells into plasma cells. This family member is localized to 11q12, among a cluster of family members. Alternative splicing of this gene results in two transcript variants that encode the same protein. The protein has no known natural ligand and its function is to enable optimal B-cell immune response, specifically against T-independent antigens. It is suspected that it acts as a calcium channel in the cell membrane. It has been shown that CD20 plays a role in the microenvironmental interactions of B cells and are therefore used to treat some types of cancer.

The term "antibody" refers to (a) immunoglobulin polypeptides and immunologically active portions of immunoglobulin polypeptides, i.e., polypeptides of the immunoglobulin family, or fragments thereof, that contain an antigen binding site that specifically binds to a specific antigen, or (b) conservatively substituted derivatives of such immunoglobulin polypeptides or fragments that specifically bind to the antigen. Examples of antibody fragments include, but are not limited to, a Fab, Fab', F(ab')2, Fd, Fv, scFv and scFv-Fc fragment, diabody, triabody, tetrabody, linear antibody, single-chain antibody, and other multispecific antibodies formed from antibody fragments. (See Holliger and Hudson, 2005, Nat. Biotechnol. 23: 1126-1136.) The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. Included in the term immunoglobulin are those immunoglobulin molecules that have modifications in the constant region, including modification (e.g., substitutions, deletions or additions) in amino acid residues that interact with Fcy receptors. Antibodies are generally described in, for example, Harlow & Lane, Antibodies: A Laboratory Manual (Cold Spring Harbor Laboratory Press, 1988).

The term "monoclonal antibody" (mAb) refers to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Kohler et al., 1975, Nature 256: 495, or recombinant DNA methods known in the art (see, e.g., U.S. Pat. No. 4,816,567). In another example, monoclonal antibodies can also be isolated from phage antibody libraries, using techniques described in Clackson et al., 1991, Nature 352: 624-628, and Marks et al., 1991, J. Mol. Biol. 222:581-597. In contrast, the antibodies in a preparation of polyclonal antibodies are typically a heterogeneous population of immunoglobulin isotypes and/or classes and also exhibit a variety of epitope specificity.

The term "biosimilar" or "follow-on biologic" or "subsequent entry biologic" refers to a biologic medical product which is almost an identical copy of an original product that is manufactured by a different company. Biosimilars are officially approved versions of original "innovator" products, and can be manufactured when the original product's patent expires. Reference to the innovator product is an integral component of the approval. A biosimilar biological product is highly similar to the reference product notwithstanding minor differences in clinically inactive components, and there are no clinically meaningful differences between the biological product and the reference product in terms of the safety, purity, and potency of the product.

The term "variant" when referring to an antibody as disclosed herein can include any antibody that retains at least some of the activity, e.g., antigen-binding activity, of the reference antibody, but which is structurally different. Variants include fragments of antibodies (e.g., Fab, Fab' and F(ab')2, Fd, Fvs, single-chain Fvs (scFv), single-chain antibodies, disulfide-linked Fvs (sdFv) fragments) and also antibodies with altered amino acid sequences, e.g., in the variable domains, due to amino acid substitutions, deletions, or insertions. Variants can occur spontaneously or be intentionally constructed. Intentionally constructed variants can be produced using art-known mutagenesis techniques. Variant antibodies can comprise conservative or non-conservative amino acid substitutions, deletions or additions. The variations are limited by the constraint that the antibody maintains a function of the reference antibody, e.g., binding to the same epitope as the reference antibody, or competitively inhibiting the reference antibody.

The terms "synergy," "synergism," or "synergistic" as used herein refer to a combination of therapies (e.g., use of a PI3K inhibitor of Formula (I) and an anti-CD20 antibody) that is more effective than the expected additive effects of any two or more single therapies. For example, a synergistic effect of a combination of therapies permits the use of lower dosages of one or more of the therapies and/or less frequent administration of said therapies to a subject. The ability to utilize lower dosages of therapies and/or to administer the therapies less frequently reduces the toxicity associated with the administration of the therapies to a subject without reducing the efficacy of said therapies in the prevention, management, treatment, or amelioration of a given disease, such as a B cell malignancy. In addition, a synergistic effect can result in improved efficacy of therapies in the prevention, management, treatment, or amelioration of a given disease, such as a B cell malignancy. Finally, synergistic effects of a combination of therapies may avoid or reduce adverse or unwanted side effects associated with the use of any single therapy. The "synergy," "synergism," or "synergistic" effect of a combination may be determined herein by the methods of Chou et al., and/or Clarke et al. See Ting-Chao Chou, Theoretical Basis, Experimental Design, and Computerized Simulation of Synergism and Antagonism in Drug Combination Studies, Pharmacol Rev 58:621-681 (2006), and Clarke et al., Issues in experimental design and endpoint analysis in the study of experimental cytotoxic agents in vivo in breast cancer and other models, Breast Cancer Research and Treatment 46:255-278 (1997), which are both incorporated by reference for the methods of determining the "synergy," synergism," or "synergistic" effect of a combination.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^{1}H$), deuterium ($^{2}H$), tritium ($^{3}H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^{1}H$), deuterium ($^{2}H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 ($^{18}O$), fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^{3}$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^{2}$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a compound contains unnatural proportions of deuterium (D).

The term "alkyl" refers to a linear or branched saturated monovalent hydrocarbon radical, wherein the alkylene may optionally be substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkylene" refers to a linear or branched saturated divalent hydrocarbon radical, wherein the alkylene may optionally be substituted with one or more substituents Q as described herein. The term "alkylene" encompasses both linear and branched alkylene, unless otherwise specified. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{1-6}$ alkylene refers to a linear saturated divalent hydrocarbon radical of 1 to 6 carbon atoms or a branched saturated divalent hydrocarbon radical of 3 to 6 carbon atoms.

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —CH$_2$O—, —CH$_2$OCH$_2$—, —CH$_2$CH$_2$O—, —CH$_2$NH—, —CH$_2$NHCH$_2$—, —CH$_2$CH$_2$NH—, —CH$_2$S—, —CH$_2$SCH$_2$—, and —CH$_2$CH$_2$S—. In certain embodiments, heteroalkylene may also be optionally substituted with one or more substituents Q as described herein.

The term "alkenyl" refers to a linear or branched monovalent hydrocarbon radical, which contains one or more, in one embodiment, one, two, three, four, or five, in another embodiment, one, carbon-carbon double bond(s). The alkenyl may be optionally substituted with one or more substituents Q as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one, two, three, four, or five, in another embodiment, one, carbon-carbon double bond(s). The alkenylene may be optionally substituted with one or more substituents Q as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more, in one embodiment, one, two, three, four, or five, in another embodiment, one, carbon-carbon double bond(s), and which contains one or more heteroatoms each independently selected from O, S, and N in the hydrocarbon chain. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—.

The term "alkynyl" refers to a linear or branched monovalent hydrocarbon radical, which contains one or more, in one embodiment, one, two, three, four, or five, in another embodiment, one, carbon-carbon triple bond(s). The alkynyl may be optionally substituted with one or more substituents Q as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic saturated bridged and/or non-bridged monovalent hydrocarbon radical, which may be optionally substituted with one or more substituents Q as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "cycloalkenyl" refers to a cyclic unsaturated, nonaromatic bridged and/or non-bridged monovalent hydrocarbon radical, which may be optionally substituted with one or more substituents Q as described herein. In certain embodiments, the cycloalkenyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclobutenyl, cyclopentenyl, cyclohexenyl, or cycloheptenyl, The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, the aralkyl are optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, N, and P in the ring. A heteroaryl group is bonded to the rest of a molecule through its aromatic ring. Each ring of a heteroaryl group can contain one or two 0 atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl may also be optionally substituted with one or more substituents Q as described herein as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. A heterocyclyl group is bonded to the rest of a molecule through its non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl may also be optionally substituted with one or more substituents Q as described herein.

The term "halogen", "halide" or "halo" refers to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, cycloalkyl, cycloalkenyl, aryl, aralkyl, heteroaryl, heteroaryl-$C_{1-6}$ alkyl, and heterocyclyl group, may be substituted with one or more substituents Q, each of which is independently selected from, e.g., (a) oxo (=O), halo, cyano (—CN), and nitro (—NO$_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, four, or five, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —P(O)R$^a$R$^d$, —P(O)(OR$^a$)R$^d$, —P(O)(OR$^a$)(OR$^d$), —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each substituent $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —P(O)(OR$^e$)R$^h$, —P(O)(OR$^e$)R$^h$, —P(O)(OR$^e$)(OR$^h$), —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The phrase "an enantiomer, a mixture of enantiomers, a mixture of two or more diastereomers, or an isotopic variant thereof; or a pharmaceutically acceptable salt, solvate, hydrate, or prodrug thereof" has the same meaning as the phrase "an enantiomer, a mixture of enantiomers, a mixture of two or more diastereomers, or an isotopic variant of the compound referenced therein; or a pharmaceutically acceptable salt, solvate, hydrate, or prodrug of the compound referenced therein; or a pharmaceutically acceptable salt, solvate, hydrate, or prodrug of an enantiomer, a mixture of enantiomers, a mixture of two or more diastereomers, or an isotopic variant of the compound referenced therein."

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The terms "resistent," "relapsed," or "refractory" refer to a cancer that has a reduced responsiveness to a treatment, e.g., the point at which the cancer does not respond to attempted forms of treatment. The cancer can be resistant at the beginning of treatment or it may become resistant during treatment. The term "refractory" can refer to a cancer for which treatment (e.g., chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

"Responsiveness" or to "respond" to treatment, and other forms of this term, as used herein, refer to the reaction of a subject to treatment with a therapeutic, e.g., a PI3K inhibitor, alone or in combination, e.g., monotherapy or combination therapy. Responsiveness to a therapy, e.g., treatment with a PI3K inhibitor alone or in combination, can be evaluated by comparing a subject's response to the therapy using one or more clinical criteria, such as IWCLL 2008 (for CLL) described in, e.g., Hallek, M. et al. (2008) Blood 111 (12): 5446-5456; the Lugano Classification described in, e.g., Cheson, B. D. et al. Journal of Clinical Oncology, 32(27): 3059-3067; and the like. Additional classifications of responsiveness are provided by. These criteria provide a set of published rules that define when cancer patients improve ("respond"), stay the same ("stable") or worsen ("progression") during treatments.

For example, a subject having CLL can be determined to be in complete remission (CR) or partial remission (PR). For example, according to IWCLL 2008, a subject is considered to be in CR if at least all of the following criteria as assessed after completion of therapy are met: (i) Peripheral blood lymphocytes (evaluated by blood and different count) below $4 \times 10^9$/L (4000 μi.); (ii) no hepatomegaly or splenomegaly by physical examination; (iii) absence of constitutional symptoms; and (iv) blood counts (e.g., neutrophils, platelets, hemoglobin) above the values set forth in Hallek, M. et al. Partial remission (PR) for CLL is defined according to IWCLL 2008 as including one of: (i) a decrease in number of blood lymphocytes by 50% or more from the value before therapy; (ii) a reduction in lymphadenopathy, as detected by CT scan or palpation; or (iii) a reduction in pretreatment enlargement of spleen or liver by 50% or more, as detected by CT scan or palpation; and blood counts (e.g., neutrophils, platelets, hemoglobin) according to the values set forth in Hallek, M. et al. In other embodiments, a subject having CLL is determined to have progressive disease (PD) or stable disease (SD). For example, according to IWCLL 2008, a subject is considered to be in PD during therapy or after therapy if at least one of the following criteria is met: (i) progression on lymphadenopathy; (ii) an increase in pretreatment enlargement of spleen or liver by 50% or more, or de novo appearance of hepatomegaly or splenomegaly; (iii) an increase in the number of blood lymphocytes by 50% or more with at least 5000 B lymphocytes per microliter; (iv) transformation to a more aggressive histology (e.g., Richter syndrome); or (v) occurrence of cytopenia (neutropenia, anemia or thrombocytopenia) attributable to CLL. Stable disease (SD) for CLL is defined according to IWCLL 2008 as a patient who has not achieved CR or a PR, and who has not exhibited progressive disease.

For example, in some embodiments, a subject with CLL responds to treatment with a PI3K inhibitor, alone or in combination, if at least one of the criteria for disease progression according to IWCLL is retarded or reduced, e.g., by about 10%, 20%, 30%, 40%, 50%, 60%, 70%, 80%, 90% or more. In another example, a subject responds to treatment with a PI3K inhibitor, alone or in combination, if the subject experiences a life expectancy extension, e.g., extended by about 5%, 10%, 20%, 30%, 40%, 50% or more beyond the life expectancy predicted if no treatment is administered. In another example, a subject responds to treatment with a PI3K inhibitor, alone or in combination, if the subject has one or more of: an increased progression-free survival, overall survival or increased time to progression (TTP), e.g., as described in Hallek, M. et al.

Compounds

Disclosed herein are PI3K inhibitors of Formula (I):

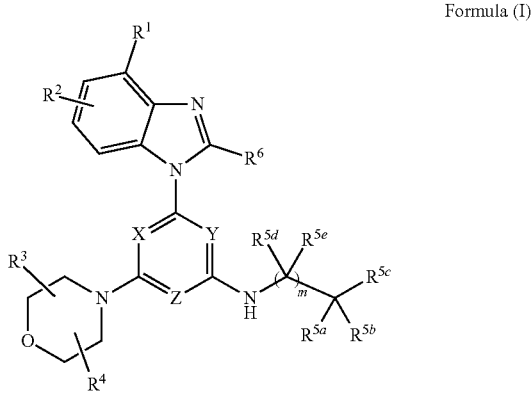

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or $CR^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —C(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5c}$ is —$(CR^{5f}R^{5g})_n$—$(C_{6-14}$ aryl$)$ or —$(CR^{5f}R^{5g})_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$; or —S(O)$_2$N$R^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in $R^1$, $R^2$, $R^3$, $R^4$, $R^6$, $R^X$, $R^{1a}$, $R^{1b}$, $R^{1c}$, $R^{1d}$, $R^{5a}$, $R^{5b}$, $R^{5c}$, $R^{5d}$, $R^{5e}$, $R^{5f}$ and $R^{5g}$ is optionally substituted with one or more, in one embodiment, one, two, three, four, or five substituents Q, wherein each substituent Q is independently selected from (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)NleR$^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents $Q^a$; or (iii) $R^b$ and $R^c$ together with the N atom to which they are attached form heterocyclyl, which is further optionally substituted with one or more, in one embodiment, one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl; or wherein two substituents Q that are adjacent to each other optionally form a $C_{3-10}$ cycloalkenyl, $C_{6-14}$ aryl, heteroaryl, or heterocyclyl, each optionally substituted with one, two, three, or four substituents $Q^a$.

In one embodiment of a compound of Formula (I),

X, Y, and Z are each independently N or C$R^X$, with the proviso that at least two of X, Y, and Z are nitrogen atoms; where $R^x$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{10}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5c}$ is —(C$R^{5f}R^{5g}$)$_n$—(C$_{6-14}$ aryl) or —(C$R^{5f}R^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$; or —S(O)$_2$N$R^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five substituents Q as defined herein.

In another embodiment of a compound of Formula (I),

X, Y, and Z are each independently N or C$R^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2$ $R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene; $R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(C)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(C)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(C)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5c}$ is —(C$R^{5f}R^{5g}$)$_n$—(C$_{6-14}$ aryl) or —(C$R^{5f}R^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1a}$C(O)$R^{1d}$, —N$R^{1a}$C(O)O$R^{1d}$, —N$R^{1a}$C(C)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(C)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1a}$C(O)$R^{1d}$, —N$R^{1a}$C(O)O$R^{1d}$, —N$R^{1a}$C(C)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(C)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$; or —S(O)$_2$N$R^{1b}R^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five substituents Q as defined herein.

In yet another embodiment of a compound of Formula (I),

X, Y, and Z are each independently N or C$R^X$, with the proviso that at least two of X, Y, and Z are nitrogen atoms; where $R^X$ is hydrogen or $C_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2$ $R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(C)NR$^{1b}$R$^{1c}$, —NR$^{1a}$C(=NR$^1$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(C)NR$^{1b}$R$^{1c}$, —NR$^{1a}$C(=NR$^1$)NR$^{1b}$R$^{1c}$, —NR$^{1a}$S(O)R$^{1d}$, —NR$^{1a}$S(O)$_2$R$^{1d}$, —NR$^{1a}$S(C)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^5$ is —(CR$^{5f}$R$^{5g}$)$_n$—(C$_{6-14}$ aryl) or —(CR$^{5f}$R$^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of $R^{5f}$ and one occurrence of $R^{5g}$ are attached to the same carbon atom, the R$^{5f}$ and R$^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five substituents Q as defined herein.

In still another embodiment of a compound of Formula (I),

X, Y, and Z are N;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^1$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5c}$ is —(CR$^{5f}$R$^{5g}$)$_n$—(C$_{6-14}$ aryl) or —(CR$^{5f}$R$^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS (O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —S(O)R$^{1a}$, —S(O)$_2$R$^{1a}$, —S(O)NR$^{1b}$R$^{1c}$, or —S(O)$_2$NR$^{1b}$R$^{1c}$; or (d) when one occurrence of R$^{5f}$ and one occurrence of R$^{5g}$ are attached to the same carbon atom, the R$^{5f}$ and R$^{5g}$ together with the carbon atom to which they are attached form a $C_{3-10}$ cycloalkyl or heterocyclyl;

R$^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl is optionally substituted with one or more, in one embodiment, one, two, three, four, or five substituents Q as defined herein.

In some embodiments of compounds of structural Formula (I):

X, Y, and Z are each N;

R$^1$ and R$^2$ are each hydrogen;

R$^3$ and R$^4$ are each hydrogen;

R$^{ya}$ is $C_{1-6}$ alkyl;

R$^{5b}$ is $C_{1-6}$ alkyl;

R$^{5c}$ is —(CH$_2$)-phenyl, wherein R$^{5c}$ is optionally substituted with one, two, three, or four, substituents Q;

R$^{5d}$ and R$^{5e}$ are each hydrogen;

R$^6$ is CHF$_2$; and m is 0;

wherein each alkyl is optionally substituted with one, two, three, or four, substituents Q, wherein each substituent Q is independently selected from $C_{6-14}$ aryl, heteroaryl, and heterocyclyl, each of which is further optionally substituted with one, two, three, or four, substituents Q$^a$, wherein the heteroaryl has from 5 to 10 ring atoms and one or more heteroatoms independently selected from O, S, and N, and the heterocyclyl has from 3 to 15 ring atoms and one or more heteroatoms independently selected from O, S, and N;

wherein each Q$^a$ is independently selected from the group consisting of halo, $C_{1-6}$ alkyl, $C_{1-6}$ alkylsulfonyl and —OR$^e$, wherein R$^e$ is hydrogen or $C_{1-6}$ alkyl.

Also provided herein is a compound of Formula (IX):

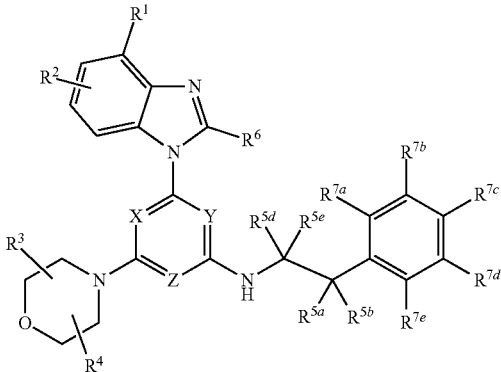

Formula (IX)

or an enantiomer, a mixture of enantiomers, a mixture of two or more diastereomers, or an isotopic variant thereof; or a pharmaceutically acceptable salt, solvate, hydrate, or prodrug thereof; wherein: R$^{7a}$, R$^{7b}$, R$^{7c}$, R$^{7d}$, and R$^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents Q$^a$; or (c) —C(O)R$^a$, —C(O)OR$^a$, —C(O)NR$^b$R$^e$, —C(NR$^a$)NR$^b$R$^c$, —OR$^a$, —OC(O)R$^a$, —OC(O)OR$^a$, —OC(O)NR$^b$R$^e$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^e$, —NR$^a$C(O)R$^d$, —NR$^a$C(O)OR$^d$, —NR$^a$C(O)NR$^b$R$^e$, —NR$^a$C(=NR$^d$)NR$^b$R$^e$, —NR$^a$S(O)R$^d$, —NR$^a$S(O)$_2$R$^d$, —NR$^a$S(O)NR$^b$R$^e$, —NR$^a$S(O)$_2$NR$^b$R$^c$, —SR$^a$, —S(O)R$^a$, —S(O)$_2$R$^a$, —S(O)NR$^b$R$^c$, or —S(O)$_2$NR$^b$R$^c$; or two of R$^{7a}$, R$^{7b}$, R$^{7c}$, R$^{7d}$, and R$^{7e}$ that are adjacent to each other form $C_{3-10}$ cycloalkenyl, $C_{6-14}$ aryl, heteroaryl, or heterocyclyl, each optionally substituted with one, two, three, or four substituents Q$^a$; and R$^1$, R$^2$, R$^3$, R$^4$, R$^6$, R$^{1a}$, R$^{1b}$, R$^{1c}$, R$^{1d}$, R$^{5a}$, R$^{5b}$, R$^{5d}$, R$^{5e}$, X, Y, and Z are each as defined herein.

In certain embodiments of compounds of Formula (IX), one of R$^{7a}$, R$^{7b}$, R$^{7c}$, R$^{7d}$, and R$^{7e}$ is $C_{6-14}$ aryl, heteroaryl, or heterocyclyl, each of which is optionally substituted with one, two, three, or four substituents Q$^a$; in certain embodiments, one of R$^{7a}$, R$^{7b}$, R$^{7c}$, R$^{7d}$, and R$^{7e}$ is $C_{6-14}$ aryl, e.g., phenyl, optionally substituted with one, two, three, or four substituents Q$^a$; in certain embodiments, one of R$^{7a}$, R$^{7b}$, R$^{7c}$, R$^{7d}$, and R$^{7e}$ is heteroaryl, e.g., 5-membered or 6-membered heteroaryl, optionally substituted with one, two, three, or four substituents Q$^a$; in certain embodiments, one of R$^{7a}$, R$^{7b}$, R$^{7c}$, R$^{7d}$, and R$^{7e}$ is heterocyclyl, e.g., 5-membered or 6-membered heterocyclyl, optionally substituted with one, two, three, or four substituents Q$^a$; in certain embodiments, one of R$^{7a}$, R$^{7b}$, R$^{7c}$, R$^{7d}$, and R$^{7e}$ is phenyl, imidazolyl, pyrozolyl, pyridinyl, piperidinyl, or piperazinyl, each optionally substituted with one, two, three, or four substituents Q$^a$; in certain embodiments, one of R$^{7a}$, R$^{7b}$, R$^{7c}$, R$^{7d}$, and R$^{7e}$ is phenyl, imidazolyl, pyrozolyl, pyridinyl, pyrimidinyl, pyrrolidinyl, piperidinyl, or piperazinyl, each optionally substituted with one, two, three, or four substituents Q$^a$; in certain embodiments, one of R$^{7a}$, R$^{7b}$, R$^{7c}$, R$^{7d}$, and R$^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of R$^{7a}$, R$^{7b}$, R$^{7c}$, R$^{7d}$, and R$^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formula (IX), R$^{7a}$ is $C_{6-14}$ aryl, heteroaryl, or heterocyclyl, each of which is optionally substituted with one, two, three, or four substituents $Q^a$; in certain embodiments, $R^{7a}$ is $C_{6-14}$ aryl, e.g., phenyl, optionally substituted with one, two, three, or four substituents $Q^a$; in certain embodiments, $R^{7a}$ is heteroaryl, e.g., 5-membered or 6-membered heteroaryl, optionally substituted with one, two, three, or four substituents $Q^a$; in certain embodiments, $R^{7a}$ is heterocyclyl, e.g., 5-membered or 6-membered heterocyclyl, optionally substituted with one, two, three, or four substituents $Q^a$; in certain embodiments, $R^{7a}$ is phenyl, imidazolyl, pyrozolyl, pyridinyl, piperidinyl, or piperazinyl, each optionally substituted with one, two, three, or four substituents $Q^a$; in certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formula (IX),
$R^1$ is hydrogen or —$OR^{1a}$, where $R^{1a}$ is $C_{1-6}$ alkyl, optionally substituted with one, two, three, four, or five substituents Q;
$R^2$ is hydrogen;
$R^3$ and $R^4$ are hydrogen;
$R^6$ is $C_{1-6}$ alkyl, optionally substituted with one, two, three, four, or five substituents Q;
$R^{5a}$ and $R^{5b}$ are each independently hydrogen, halo, $C_{1-6}$ alkyl, optionally substituted with one, two, three, four, or five substituents Q;
$R^{5d}$ and $R^{5e}$ are each independently $C_{1-6}$ alkyl, optionally substituted with one, two, three, four, or five substituents Q;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or $CR^x$, with the proviso that at least two of X, Y, and Z are N;
where $R^x$ is a hydrogen or $C_{1-6}$ alkyl, optionally substituted with one, two, three, or four substituents $Q^a$.

In certain embodiments of compounds of Formula (IX),
$R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are hydrogen;
$R^{5d}$ and $R^{5e}$ are each independently $C_{1-6}$ alkyl;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formula (IX),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is $C_{6-14}$ aryl, monocyclic heteroaryl, or monocyclic heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formula (IX),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, 5- or 6-membered heteroaryl, or 5- or 6-membered heterocyclyl, each of which is optionally substituted with one, two, three, or four substituents $Q^a$;
$R^{7c}$, $R^{7d}$, and $R^{7e}$ are hydrogen; and
X, Y, and Z are each independently N or CH.

In certain embodiments of compounds of Formula (IX),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$;
$R^{7c}$, $R^{7d}$, and $R^{7e}$ are hydrogen; and
X, Y, and Z are each independently N or CH.

In certain embodiments of compounds of Formula (IX),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are hydrogen;
$R^{5d}$ and $R^{5e}$ are methyl;
$R^{7a}$ is phenyl, imidazolyl, pyrozolyl, pyridinyl, piperidinyl, or piperazinyl, each of which is optionally substituted with one, two, three, or four substituents $Q^a$;
$R^{7c}$, $R^{7d}$, and $R^{7e}$ are hydrogen; and
X, Y, and Z are each independently N or CH.

Also provided herein is a compound of Formula (X):

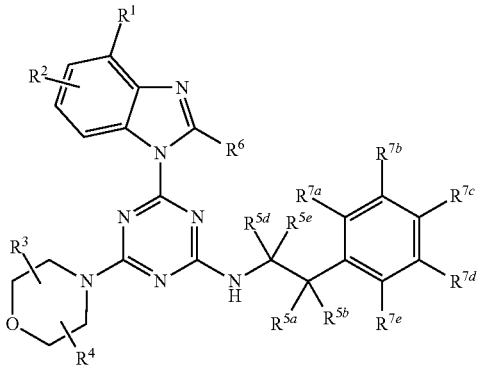

Formula (X)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{5d}$, $R^{5e}$, $R^{7a}$, $R^{7b}$, $R^{7c}$, $R^{7d}$, and $R^{7e}$ are each as defined herein.

In certain embodiments of compounds of Formula (X), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$; in certain embodiments, one of $R^{7a}$, $R^{7b}$, $R^{7c}$, $R^{7d}$, and $R^{7e}$ is $C_{6-14}$ aryl, e.g., phenyl, optionally substituted with one, two, three, or four substituents $Q^a$; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one, two, three, or four substituents $Q^a$; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formula (X), $R^{7a}$ is $C_{6-14}$ aryl, heteroaryl, or heterocyclyl, each of which is optionally substituted with one, two, three, or four substituents $Q^a$; in certain embodiments, $R^{7a}$ is $C_{6-14}$ aryl, e.g., phenyl, optionally substituted with one, two, three, or four substituents $Q^a$; in certain embodiments, $R^{7a}$ is heteroaryl, e.g., 5-membered or 6-membered heteroaryl, optionally substituted with one, two, three, or four substituents $Q^a$; in certain embodiments, $R^{7a}$ is heterocyclyl, e.g., 5-membered or 6-membered heterocyclyl, optionally substituted with one, two, three, or four substituents $Q^a$; in certain embodiments, $R^{7a}$ is phenyl, imidazolyl, pyrozolyl, pyridinyl, piperidinyl, or piperazinyl, each optionally substituted with one, two, three, or four substituents $Q^a$; in certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formula (X), $R^1$ is hydrogen or $-OR^{1a}$, where $R^{1a}$ is $C_{1-6}$ alkyl, optionally substituted with one, two, three, four, or five substituents Q;

$R^2$ is hydrogen;

$R^3$ and $R^4$ are hydrogen;

$R^6$ is $C_{1-6}$ alkyl, optionally substituted with one, two, three, four, or five substituents Q;

$R^{5a}$ and $R^{5b}$ are each independently hydrogen, halo, $C_{1-6}$ alkyl, optionally substituted with one, two, three, four, or five substituents Q;

$R^{5d}$ and $R^{5e}$ are each independently $C_{1-6}$ alkyl, optionally substituted with one, two, three, four, or five substituents Q;

$R^{7a}$ is $C_{6-14}$ aryl, heteroaryl, or heterocyclyl, each of which is optionally substituted with one, two, three, or four substituents $Q^a$; and $R^{7b}$, $R^{7c}$, $R^{7d}$, and $R^{7e}$ are hydrogen.

In certain embodiments of compounds of Formula (X), $R^1$ is hydrogen or methoxy;

$R^2$ is hydrogen;

$R^3$ and $R^4$ are hydrogen;

$R^6$ is $C_{1-6}$ alkyl, optionally substituted with one or more halo;

$R^{5a}$ and $R^{5b}$ are hydrogen;

$R^{5d}$ and $R^{5b}$ are each independently $C_{1-6}$ alkyl;

$R^{7a}$ is $C_{6-14}$ aryl, heteroaryl, or heterocyclyl, each of which is optionally substituted with one, two, three, or four substituents $Q^a$; and $R^{7b}$, $R^{7c}$, $R^{7d}$, and $R^{7e}$ are hydrogen.

In certain embodiments of compounds of Formula (X), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are hydrogen;

$R^{5d}$ and $R^{5e}$ are methyl;

$R^{7a}$ is $C_{6-14}$ aryl, monocyclic heteroaryl, or monocyclic heterocyclyl, each of which is optionally substituted with one, two, three, or four substituents $Q^a$; and $R^{7b}$, $R^{7c}$, $R^{7d}$, and $R^{7e}$ are hydrogen.

In certain embodiments of compounds of Formula (X), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are hydrogen;

$R^{5d}$ and $R^{5e}$ are methyl;

$R^{7a}$ is phenyl, 5- or 6-membered heteroaryl, or 5- or 6-membered heterocyclyl, each of which is optionally substituted with one, two, three, or four substituents $Q^a$; and $R^{7b}$, $R^{7c}$, $R^{7d}$, and $R^{7e}$ are hydrogen.

In certain embodiments of compounds of Formula (X), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are hydrogen;

$R^{5d}$ and $R^{5b}$ are methyl;

$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$; and $R^{7b}$, $R^{7c}$, $R^{7d}$, and $R^{7e}$ are hydrogen.

In certain embodiments of compounds of Formula (X), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are hydrogen;

$R^{5d}$ and $R^{5e}$ are methyl;

$R^{7a}$ is phenyl, imidazolyl, pyrozolyl, pyridinyl, piperidinyl, or piperazinyl, each of which is optionally substituted with one, two, three, or four substituents $Q^a$; and $R^{7b}$, $R^{7c}$, $R^{7d}$, and $R^{7e}$ are hydrogen.

Provide herein is a compound of Formula (XI):

Formula (XI)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)$R^a$, —C(O)O$R^a$, —C(O)N$R^b$$R^c$, —C(N$R^a$)N$R^b$$R^c$, —O$R^a$, —OC(O)$R^a$, —OC(O)O$R^a$, —OC(O)N$R^b$$R^c$, —OC(=N$R^a$)N$R^b$$R^c$, —OS(O)$R^a$, —OS(O)$_2$$R^a$, —OS(O)N$R^b$$R^c$, —OS(O)$_2$N$R^b$$R^c$, —N$R^b$$R^c$, —N$R^a$C(O)$R^d$, —N$R^a$C(O)O$R^d$, —N$R^a$C(O)N$R^b$$R^c$, —N$R^a$C(=N$R^d$)N$R^b$$R^c$, —N$R^a$S(O)$R^d$, —N$R^a$S(O)$_2$$R^d$, —N$R^a$S(O)N$R^b$$R^c$, —N$R^a$S(O)$_2$N$R^b$$R^c$, —S$R^a$, —S(O)$R^a$, —S(O)$_2$$R^a$, —S(O)N$R^b$$R^c$, or —S(O)$_2$N$R^b$$R^c$; or two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one, two, three, or four substituents $Q^a$; and $R^1$, $R^2$, $R^3$, $R^4$, $R^6$, $R^{1a}$, $R^{1b}$, $R^{1c}$, $R^{1d}$, $R^{5a}$, $R^{5b}$, $R^{5f}$, $R^{5g}$, X, Y, and Z are each as defined herein.

In certain embodiments of compounds of Formula (XI), $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}$$R^{1c}$, —C(N$R^{1a}$)N$R^{1b}$$R^{1c}$, —O$R^{1a}$, —OC(O)$R^{1a}$, —OC(O)O$R^{1a}$, —OC(O)N$R^{1b}$$R^{1c}$, —OC(=N$R^{1a}$)N$R^{1b}$$R^{1c}$, —OS(O)$R^{1a}$, —OS(O)$_2$$R^{1a}$, —OS(O)N$R^{1b}$$R^{1c}$, —OS(O)$_2$N$R^{1b}$$R^{1c}$, —N$R^{1b}$$R^{1c}$, —N$R^{1a}$C(O)$R^{1d}$, —N$R^{1a}$C(O)O$R^{1d}$, —N$R^{1a}$C(O)N$R^{1b}$$R^{1c}$, —N$R^{1a}$C(=N$R^{1d}$)N$R^{1b}$$R^{1c}$, —N$R^{1a}$S(O)$R^{1d}$, —N$R^{1a}$S(O)$_2$$R^{1d}$, —N$R^{1a}$S(O)N$R^{1b}$$R^{1c}$, —N$R^{1a}$S(O)$_2$N$R^{1b}$$R^{1c}$, —S$R^{1a}$, —S(O)$R^{1a}$, —S(O)$_2$$R^{1a}$, —S(O)N$R^{1b}$$R^{1c}$, or —S(O)$_2$N$R^{1b}$$R^{1c}$; and $R^1$, $R^2$, $R^3$, $R^4$, $R^{5f}$, $R^{5g}$, $R^6$, $R^{7a}$, $R^{7b}$, $R^{7c}$, $R^{7d}$, $R^{7e}$, X, Y, Z, $R^{1a}$, $R_{1b}$, $R_{1c}$, and $R^{1d}$ are defined herein elsewhere.

In certain embodiments of compounds of Formula (XI), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$; in certain embodiments, one of $R^{7a}$, $R^{7b}$, $R^{7c}$, $R^{7d}$, and $R^{7e}$ is $C_{6-14}$ aryl, e.g., phenyl, optionally substituted with one, two, three, or four substituents $Q^a$; in certain embodiments, one of $R^{7a}$, $R^{7b}$, $R^{7c}$, $R^{7d}$, and $R^{7e}$ is heteroaryl, e.g., 5-membered or 6-membered heteroaryl, optionally substituted with one, two, three, or four substituents $Q^a$; in certain embodiments, one of $R^{7a}$, $R^{7b}$, $R^{7c}$, $R^{7d}$, and $R^{7e}$ is heterocyclyl, e.g., 5-membered or 6-membered heterocyclyl, optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formula (XI), $R^{7a}$ is $C_{6-14}$ aryl, heterocyclyl, or heterocyclyl, each of which is optionally substituted with one, two, three, or four substituents $Q^a$; in certain embodiments, $R^{7a}$ is $C_{6-14}$ aryl, e.g., phenyl, optionally substituted with one, two, three, or four substituents $Q^a$; in certain embodiments, $R^{7a}$ is heteroaryl, e.g., 5-membered or 6-membered heteroaryl, optionally substituted with one, two, three, or four substituents $Q^a$; in certain embodiments, $R^{7a}$ is heterocyclyl, e.g., 5-membered or 6-membered heterocyclyl, optionally substituted with one, two, three, or four substituents $Q^a$; in certain embodiments, $R^{7a}$ is phenyl, imidazolyl, pyrozolyl, pyridinyl, piperidinyl, or piperazinyl, each optionally substituted with one, two, three, or four substituents $Q^a$; in certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; in certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and in certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments of compounds of Formula (XI),
$R^1$ is hydrogen or $-OR^{1a}$, where $R^{1a}$ is $C_{1-6}$ alkyl, optionally substituted with one, two, three, four, or five substituents Q;
$R^2$ is hydrogen;
$R^3$ and $R^4$ are hydrogen;
$R^6$ is $C_{1-6}$ alkyl, optionally substituted with one, two, three, four, or five substituents Q;
$R^{5a}$ and $R^{5b}$ are each independently $C_{1-6}$ alkyl, optionally substituted with one, two, three, four, or five substituents Q;
$R^{5f}$ and $R^{5g}$ are each independently hydrogen, halo, $C_{1-6}$ alkyl, optionally substituted with one, two, three, four, or five substituents Q; or $R^{5f}$ and $R^{5g}$ together with the carbon atom to which they are attached form $C_{1-10}$ cycloalkyl or heterocyclyl, each of which is optionally substituted with one, two, three, four, or five substituents Q;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or $CR^x$, with the proviso that at least two of X, Y, and Z are N; where $R^x$ is a hydrogen or $C_{1-6}$ alkyl, optionally substituted with one, two, three, or four substituents $Q^a$.

In certain embodiments of compounds of Formula (XI),
$R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are each independently $C_{1-6}$ alkyl;
$R^{5f}$ and $R^{5g}$ are each independently hydrogen or $C_{1-6}$ alkyl; or $R^{5f}$ and $R^{5g}$ together with the carbon atom to which they are attached form $C_{1-10}$ cycloalkyl;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formula (XI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;
$R^{7a}$ is $C_{6-14}$ aryl, monocyclic heteroaryl, or monocyclic heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In certain embodiments of compounds of Formula (XI),
$R^1$ is hydrogen or methoxy;
$R^2$ is hydrogen;
$R^3$ and $R^4$ are hydrogen;
$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;

$R^{7a}$ is phenyl, 5- or 6-membered heteroaryl, or 5- or 6-membered heterocyclyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

In certain embodiments of compounds of Formula (XI), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;

$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

In certain embodiments of compounds of Formula (XI), $R^1$ is hydrogen or methoxy;

$R^2$ is hydrogen;

$R^3$ and $R^4$ are hydrogen;

$R^6$ is difluoromethyl;

$R^{5a}$ and $R^{5b}$ are methyl;

$R^{5f}$ and $R^{5g}$ are hydrogen; or $R^{5f}$ and $R^{5g}$ together with the carbon atom to which they are attached form cyclopropyl, cyclobutyl, cyclopentyl, or cyclohexyl;

$R^{7a}$ is phenyl, imidazolyl, pyrozolyl, pyridinyl, piperidinyl, or piperazinyl, each of which is optionally substituted with one, two, three, or four substituents $Q^a$;

$R^{7b}$, $R^{7c}$, $R^{7d}$, and $R^{7e}$ are hydrogen; and

X, Y, and Z are each independently N or CH.

Provided herein is a compound of Formula (XVI):

Formula (XVI)

or an enantiomer, a mixture of enantiomers, a mixture of two or more diastereomers, or an isotopic variant thereof; or a pharmaceutically acceptable salt, solvate, hydrate, or prodrug thereof; wherein $R^1$, $R^2$, $R^3$, $R^4$, $R^6$, $R^{5a}$, $R^{5b}$, $R^{7a}$, $R^{7b}$, $R^{7c}$, and $R^{7e}$ are each as defined herein.

In one embodiment of a compound of Formula (XVI), one of $R^{7a}$, $R^{7b}$, $R^{7c}$, $R^{7d}$, and $R^{7e}$ is $C_{6-14}$ aryl, heteroaryl, or heterocyclyl, each of which is optionally substituted with one, two, three, or four substituents $Q^a$, and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In another embodiment of a compound of Formula (XVI), one of $R^{7a}$, $R^{7b}$, $R^{7c}$, $R^{7d}$, and $R^{7e}$ is $C_{6-14}$ aryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is heteroaryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is 5-membered or 6-membered heteroaryl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is heterocyclyl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is 5-membered or 6-membered heterocyclyl, which is optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is phenyl, imidazolyl, pyrozolyl, pyridinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In yet another embodiment of a compound of Formula (XVI), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In still another embodiment of a compound of Formula (XVI), one of $R^{7a}$, $R^{7b}$, $R^{7c}$, $R^{7d}$, and $R^{7e}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, the remaining of $R^{7a}$, $R^{7b}$, $R^{7c}$, $R^{7d}$, and $R^{7e}$, X, Y, and Z are each as defined herein.

In one embodiment of a compound of Formula (XVI), $R^{7a}$ is $C_{6-14}$ aryl, heteroaryl, or heterocyclyl, each of which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In another embodiment of a compound of Formula (XVI), $R^{7a}$ is $C_{6-14}$ aryl, which is optionally substituted with one, two, three, or four substituents $Q^a$; and $R^1$, $R^2$, $R^3$, $R^4$, $R^6$, $R^{5a}$, $R^{5b}$, $R^{7c}$, $R^{7e}$, X, Y, and Z are each as defined herein.

In yet another embodiment of a compound of Formula (XVI), $R^{7a}$ is heteroaryl, which is optionally substituted with one, two, three, or four substituents $Q^a$; and $R^1$, $R^2$, $R^3$, $R^4$, $R^6$, $R^{5a}$, $R^{5b}$, $R^{7c}$, $R^{7d}$, $R^{7e}$, X, Y, and Z are each as defined herein.

In yet another embodiment of a compound of Formula (XVI), $R^{7a}$ is 5-membered or 6-membered heteroaryl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is heterocyclyl, which is optionally substituted with one, two, three, or four substituents $Q^a$; and $R^1$, $R^2$, $R^3$, $R^4$, $R^6$, $R^{5a}$, $R^{5b}$, $R^{7c}$, $R^{7d}$, $R^{7e}$, X, Y, and Z are each as defined herein.

In yet another embodiment of a compound of Formula (XVI), $R^{7a}$ is 5-membered or 6-membered heterocyclyl, which is optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is phenyl, imidazolyl, pyrozolyl, pyridinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In yet another embodiment of a compound of Formula (XVI), $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In yet another embodiment of a compound of Formula (XVI), $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-methylpyridin-4-yl, 2-methoxypyridin-4-yl, 1-methylpiperidin-4-yl, or 4-methylpiperazin-1-yl; and $R^1$, $R^2$, $R^3$, $R^4$, $R^6$, $R^{5a}$, $R^{5b}$, $R^{7b}$, $R^{7c}$, $R^{7d}$, $R^{7e}$, X, Y, and Z are each as defined herein.

In one embodiment of a compound of Formula (XVI),
$R^1$ is hydrogen or —$OR^{1a}$, where $R^{1a}$ is $C_{1-6}$ alkyl, optionally substituted with one, two, three, four, or five substituents Q;
$R^2$ is hydrogen;
$R^3$ and $R^4$ are hydrogen;
$R^6$ is $C_{1-6}$ alkyl, optionally substituted with one, two, three, four, or five substituents Q;
$R^{5a}$ and $R^{5b}$ are each independently $C_{1-6}$ alkyl, optionally substituted with one, two, three, four, or five substituents Q;
$R^{7a}$ is $C_{6-14}$ aryl, heteroaryl, or heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are each independently $C_{1-6}$ alkyl;
$R^{7a}$ is $C_{6-14}$ aryl, heteroaryl, or heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is $C_{6-14}$ aryl, monocyclic heteroaryl, or monocyclic heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, 5- or 6-membered heteroaryl, or 5- or 6-membered heterocyclyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI),
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, imidazolyl, pyrozolyl, pyridinyl, pyrimidinyl, pyrrolidinyl, piperidinyl, or piperazinyl, each of which is optionally substituted with one, two, three, four, or five substituents Q; and
$R^{7b}$, $R^{7c}$, $R^{7d}$, and $R^{7e}$ are hydrogen.

In one embodiment of a compound of Formula (XVI),
$R^1$ is hydrogen or methoxy;

$R^2$ is hydrogen;
$R^3$ and $R^4$ are hydrogen;
$R^6$ is difluoromethyl;
$R^{5a}$ and $R^{5b}$ are methyl;
$R^{7a}$ is phenyl, imidazolyl, pyrozolyl, pyridinyl, piperidinyl, or piperazinyl, each of which is optionally substituted with one, two, three, or four substituents $Q^a$; and
$R^{7b}$, $R^{7c}$, $R^{7d}$, and $R^{7e}$ are hydrogen.

In one embodiment of a compound of Formula (XVI), $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$ $R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^3$, $R^4$, $R^6$, $R^{7a}$, $R^{7b}$, $R^{7c}$, $R^{7d}$, $R^{7e}$, $R^{1a}$, $R^{1b}$, $R^{1c}$, and $R^{1d}$ are defined herein elsewhere.

In one embodiment of any of the formulae provided herein,
$R^1$ is hydrogen or —O$R^{1a}$, where $R^{1a}$ is $C_{1-6}$ alkyl, optionally substituted with one, two, three, four, or five substituents Q;
$R^2$ is hydrogen;
$R^3$ and $R^4$ are hydrogen;
$R^6$ is $C_{1-6}$ alkyl, optionally substituted with one, two, three, four, or five substituents Q;
$R^{5a}$ and $R^{5b}$ are each independently hydrogen or $C_{1-6}$ alkyl optionally substituted with one, two, three, four, or five substituents Q;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CR$^x$, with the proviso that at least two of X, Y, and Z are N;
where $R^x$ is a hydrogen or $C_{1-6}$ alkyl, optionally substituted with one, two, three, or four substituents $Q^a$.

In one embodiment of any of the formulae provided herein,
$R^1$ is hydrogen or methoxy;
$R^2$ is hydrogen;
$R^3$ and $R^4$ are hydrogen;
$R^6$ is $C_{1-6}$ alkyl, optionally substituted with one or more halo;
$R^{5a}$ and $R^{5b}$ are each independently hydrogen or $C_{1-6}$ alkyl;
$R^{7a}$ is $C_{6-14}$ aryl, heteroaryl, or heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In one embodiment of any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is $C_{6-14}$ aryl, monocyclic heteroaryl, or monocyclic heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In one embodiment of any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, 5- or 6-membered heteroaryl, or 5- or 6-membered heterocyclyl, each of which is optionally substituted with one, two, three, or four substituents $Q^a$;
$R^{7b}$, $R^{7c}$, $R^{7d}$, and $R^{7e}$ are hydrogen; and
X, Y, and Z are each independently N or CH.

In one embodiment of any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, imidazolyl, pyrozolyl, pyridinyl, pyrimidinyl, pyrrolidinyl, piperidinyl, or piperazinyl, each of which is optionally substituted with one, two, three, or four substituents $Q^a$;
$R^{7b}$, $R^{7d}$, and $R^{7e}$ are hydrogen; and
X, Y, and Z are each independently N or CH.

In one embodiment of any of the formulae provided herein,
$R^1$ is hydrogen or methoxy;
$R^2$ is hydrogen;
$R^3$ and $R^4$ are hydrogen;
$R^6$ is difluoromethyl;
$R^{5a}$ and $R^{5b}$ are each independently hydrogen or $C_{1-6}$ alkyl;
$R^{7a}$ is phenyl, imidazolyl, pyrozolyl, pyridinyl, piperidinyl, or piperazinyl, each of which is optionally substituted with one, two, three, or four substituents $Q^a$;
$R^{7b}$, $R^{7d}$, and $R^{7e}$ are hydrogen; and
X, Y, and Z are each independently N or CH.

The groups or variables, $R^1$, $R^2$, $R^3$, $R^4$, $R^6$, $R^{5a}$, $R^{5b}$, $R^{5c}$, $R^{5d}$, $R^{5e}$, $R^{5f}$, $R^{5g}$, $R^{7a}$, $R^{7b}$, $R^{7c}$, $R^{7d}$, $R^{7e}$, m, n, X, Y, and Z in Formulae provided herein, e.g., Formulae (I), (IX), (X), (XI), (XVI), are further defined in the embodiments described herein. All combinations of the embodiments provided herein for such groups and/or variables are within the scope of this disclosure.

In certain embodiments, $R^1$ is hydrogen. In certain embodiments, $R^1$ is cyano. In certain embodiments, $R^1$ is halo. In certain embodiments, $R^1$ is fluoro, chloro, bromo, or iodo. In certain embodiments, $R^1$ is nitro. In certain embodiments, $R^1$ is $C_{1-6}$ alkyl, optionally substituted with one, two, three, four, or five substituents Q as described herein. In certain embodiments, $R^1$ is $C_{2-6}$ alkenyl, optionally substituted with one, two, three, four, or five substituents Q as described herein. In certain embodiments, $R^1$ is $C_{2-6}$ alkynyl, optionally substituted with one, two, three, four, or five substituents Q as described herein. In certain embodiments, $R^1$ is $C_{3-10}$ cycloalkyl, optionally substituted with one, two, three, four, or five substituents Q as described herein. In certain embodiments, $R^1$ is $C_{6-14}$ aryl, optionally substituted with one, two, three, four, or five substituents Q as described herein. In certain embodiments, $R^1$ is $C_{7-15}$ aralkyl, optionally substituted with one, two, three, four, or five substituents Q as described herein. In certain embodiments, $R^1$ is heteroaryl, optionally substituted with one, two, three, four, or five substituents Q as described herein. In certain embodiments, $R^1$ is heterocyclyl, optionally substituted with one, two, three, four, or five substituents Q as described herein.

In certain embodiments, $R^1$ is —C(O)$R^{1a}$, wherein $R^{1a}$ is as defined herein. In certain embodiments, $R^1$ is —C(O)O$R^{1a}$, wherein $R^{1a}$ is as defined herein. In certain embodiments, $R^1$ is —C(O)N$R^{1b}R^{1c}$, wherein $R^{1b}$ and $R^{1c}$ are each as defined herein. In certain embodiments, $R^1$ is —C(N$R^{1a}$)N$R^{1b}R^{1c}$, wherein $R^{1a}$, $R^{1b}$, and $R^{1c}$ are each as defined herein. In certain embodiments, $R^1$ is —O$R^{1a}$, wherein $R^{1a}$ is as defined herein. In certain embodiments, $R^1$ is —O—$C_{1-6}$ alkyl, wherein the alkyl is optionally substituted with one, two, three, four, or five substituents Q as described herein. In certain embodiments, $R^1$ is methoxy, ethoxy, propoxy, isopropoxy, or 3-dimethylaminopropoxy. In certain embodiments, $R^1$ is —OC(O)$R^{1d}$, wherein $R^{1a}$ is as defined herein. In certain embodiments, $R^1$ is —OC(O)O$R^{1d}$, wherein $R^{1a}$ is as defined herein. In certain embodiments, $R^1$ is —OC(O)N$R^{1b}R^{1c}$, wherein $R^{1b}$ and $R^{1c}$ are each as defined herein. In certain embodiments, $R^1$ is —OC(=N$R^{1a}$)N$R^{1b}R^{1c}$, wherein $R^{1a}$, $R^{1b}$, and $R^{1c}$ are each as defined herein. In certain embodiments, $R^1$ is —OS(O)$R^{1d}$, wherein $R^{1d}$ is as defined herein. In certain embodiments, $R^1$ is —OS(O)$_2R^{1d}$, wherein $R^{1d}$ is as defined herein. In certain embodiments, $R^1$ is —OS(O)N$R^{1b}R^{1c}$, wherein $R^{1b}$ and $R^{1c}$ are each as defined herein. In certain embodiments, $R^1$ is —OS(O)$_2$N$R^{1b}R^{1c}$, wherein $R^{1b}$ and $R^{1c}$ are each as defined herein. In certain embodiments, $R^1$ is —N$R^{1b}R^{1c}$, wherein $R^{1b}$ and $R^{1c}$ are each as defined herein. In certain embodiments, $R^1$ is —N$R^{1a}$C(O)$R^{1d}$, wherein $R^{1a}$ and $R^{1d}$ are each as defined herein. In certain embodiments, $R^1$ is —N$R^{1d}$C(O)O$R^{1d}$, wherein $R^{1a}$ and $R^{1d}$ are each as defined herein. In certain embodiments, $R^1$ is —N$R^{1a}$dC(O)N$R^{1b}R^{1c}$, wherein $R^{1a}$, $R^{1b}$ and $R^{1c}$ are each as defined herein. In certain embodiments, $R^1$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^1$ is —N$R^{1a}$S(O)$R^{1d}$, wherein $R^{1a}$ and $R^{1d}$ are each as defined herein. In certain embodiments, $R^1$ is —N$R^{1a}$S(O)$_2R^{1d}$, wherein $R^{1a}$ and $R^{1d}$ are each as defined herein. In certain embodiments, $R^1$ is —N$R^{1a}$S(O)N$R^{1b}R^{1c}$, wherein $R^{1a}$, $R^{1b}$, and $R^{1c}$ are each as defined herein. In certain embodiments, $R^1$ is —N$R^{1a}$S(O)$_2$N$R^{1b}R^{1c}$, wherein $R^{1a}$, $R^{1b}$, and $R^{1c}$ are each as defined herein. In certain embodiments, $R^1$ is —S$R^{1a}$, wherein $R^{1a}$ is as defined herein. In certain embodiments, $R^1$ is —S(O)$R^{1a}$, wherein $R^{1a}$ is as defined herein. In certain embodiments, $R^1$ is —S(O)$_2R^{1a}$, wherein $R^{1a}$ is as defined herein. In certain embodiments, $R^1$ is —S(O)N$R^{1b}R^{1c}$, wherein $R^{1b}$ and $R^{1c}$ are each as defined herein. In certain embodiments, $R^1$ is —S(O)$_2$N$R^{1b}R^{1c}$; wherein $R^{1b}$ and $R^{1c}$ are each as defined herein.

In certain embodiments, $R^2$ is hydrogen. In certain embodiments, $R^2$ is cyano. In certain embodiments, $R^2$ is halo. In certain embodiments, $R^2$ is fluoro, chloro, bromo, or iodo. In certain embodiments, $R^2$ is nitro. In certain embodiments, $R^2$ is $C_{1-6}$ alkyl, optionally substituted with one, two, three, four, or five substituents Q as described herein. In certain embodiments, $R^2$ is $C_{2-6}$ alkenyl, optionally substituted with one, two, three, four, or five substituents Q as described herein. In certain embodiments, $R^2$ is $C_{2-6}$ alkynyl, optionally substituted with one, two, three, four, or five substituents Q as described herein. In certain embodiments, $R^2$ is $C_{3-10}$ cycloalkyl, optionally substituted with one, two, three, four, or five substituents Q as described herein. In certain embodiments, $R^2$ is $C_{3-7}$ cycloalkyl, optionally substituted with one, two, three, four, or five substituents Q as described herein. In certain embodiments, $R^2$ is $C_{6-14}$ aryl, optionally substituted with one, two, three, four, or five substituents Q as described herein. In certain embodiments, $R^2$ is $C_{7-15}$ aralkyl, optionally substituted with one, two, three, four, or five substituents Q as described herein. In certain embodiments, $R^2$ is heteroaryl, optionally substituted with one, two, three, four, or five substituents Q as described herein. In certain embodiments, $R^2$ is heterocyclyl, optionally substituted with one, two, three, four, or five substituents Q as described herein.

In certain embodiments, $R^2$ is —C(O)$R^{1a}$, wherein $R^{1a}$ is as defined herein. In certain embodiments, $R^2$ is —C(O)O$R^{1a}$, wherein $R^{1a}$ is as defined herein. In certain embodiments, $R^2$ is —C(O)N$R^{1b}R^{1c}$, wherein $R^{1b}$ and $R^{1c}$ are each as defined herein. In certain embodiments, $R^2$ is —C(N$R^{1a}$)N$R^{1b}R^{1c}$, wherein $R^{1a}$, $R^{1b}$, and $R^{1c}$ are each as defined herein. In certain embodiments, $R^2$ is —O$R^{1a}$, wherein $R^{1a}$ is as defined herein. In certain embodiments, $R^1$ is —O—$C_{1-6}$ alkyl, wherein the alkyl is optionally substituted with one, two, three, four, or five substituents Q as described herein. In certain embodiments, $R^1$ is methoxy, ethoxy, propoxy, isopropoxy, or 3-dimethylaminopropoxy. In certain embodiments, $R^2$ is —OC(O)$R^{1a}$, wherein $R^{1a}$ is as defined herein. In certain embodiments, $R^2$ is —OC(O)O$R^{1a}$, wherein $R^{1a}$ is as defined herein. In certain embodiments, $R^2$ is —OC(O)N$R^{1b}R^{1c}$, wherein $R^{1b}$ and $R^{1c}$ are each as defined herein. In certain embodiments, $R^2$ is —OC(=N$R^{1a}$)N$R^{1b}R^{1c}$, wherein $R^{1a}$, $R^{1b}$, and $R^{1c}$ are each as defined herein. In certain embodiments, $R^2$ is —OS(O)$R^{1a}$, wherein $R^{1a}$ is as defined herein. In certain embodiments, $R^2$ is —OS(O)$_2R^{1a}$, wherein $R^{1a}$ is as defined herein. In certain embodiments, $R^2$ is —OS(O)N$R^{1b}R^{1c}$, wherein $R^{1b}$ and $R^{1c}$ are each as defined herein. In certain embodiments, $R^2$ is —OS(O)$_2$N$R^{1b}R^{1c}$, wherein $R^{1b}$ and $R^{1c}$ are each as defined herein. In certain embodiments, $R^2$ is —N$R^{1b}R^{1c}$, wherein $R^{1b}$ and $R^{1c}$ are each as defined herein. In certain embodiments, $R^2$ is amino (—NH$_2$). In certain embodiments, $R^2$ is —N$R^{1a}$C(O)$R^{1d}$, wherein $R^{1a}$ and $R^{1d}$ are each as defined herein. In certain embodiments, $R^2$ is —N$R^{1a}$C(O)O$R^{1d}$, wherein $R^{1a}$ and $R^{1d}$ are each as defined herein. In certain embodiments, $R^2$ is —N$R^{1a}$C(O)N$R^{1b}$, wherein $R^{1a}$, $R^{1b}$, and $R^{1c}$ are each as defined herein. In certain embodiments, $R^2$ is N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^2$ is —N$R^{1a}$S(O)$R^{1d}$, wherein $R^{1a}$ and $R^{1d}$ are each as defined herein. In certain embodiments, $R^2$ is —N$R^{1a}$S(O)$_2R^{1d}$, wherein $R^{1a}$ and $R^{1d}$ are each as defined herein. In certain embodiments, $R^2$ is —N$R^{1a}$S(O)N$R^{1b}R^{1c}$, wherein $R^{1a}$, $R^{1b}$, and $R^{1c}$ are each as defined herein. In certain embodiments, $R^2$ is —N$R^{1a}$S(O)$_2$N$R^{1b}R^{1c}$, wherein $R^{1a}$, $R^{1b}$, and $R^{1c}$ are each as defined herein. In certain embodiments, $R^2$ is —S$R^{1a}$, wherein $R^{1a}$ is as defined herein. In certain embodiments, $R^2$ is —S(O)$R^{1a}$, wherein $R^{1a}$ is as defined herein. In certain embodiments, $R^2$ is —S(O)$_2R^{1a}$, wherein $R^{1a}$ is as defined herein. In certain embodiments, $R^2$ is —S(O)N$R^{1b}R^{1c}$, wherein $R^{1b}$ and $R^{1c}$ are each as defined herein. In certain embodiments, $R^2$ is —S(O)$_2$N$R^{1b}R^{1c}$; wherein $R^{1b}$ and $R^{1c}$ are each as defined herein.

In certain embodiments, $R^3$ is hydrogen. In certain embodiments, $R^3$ is $C_{1-6}$ alkyl, optionally substituted with one, two, three, four, or five substituents Q as described herein. In certain embodiments, $R^3$ is hydrogen, methyl, ethyl, or propyl (e.g., n-propyl, isopropyl, or 2-isopropyl).

In certain embodiments, $R^4$ is hydrogen. In certain embodiments, $R^4$ is $C_{1-6}$ alkyl, optionally substituted with one, two, three, four, or five substituents Q as described herein. In certain embodiments, $R^4$ is hydrogen, methyl, ethyl, or propyl (e.g., n-propyl, isopropyl, or 2-isopropyl).

In certain embodiments, $R^3$ and $R^4$ are linked together to form a bond. In certain embodiments, $R^3$ and $R^4$ are linked together to form $C_{1-6}$ alkylene, optionally substituted with one, two, three, four, or five substituents Q as described herein. In certain embodiments, $R^3$ and $R^4$ are linked together to form methylene, ethylene, or propylene, each optionally substituted with one, two, three, four, or five substituents Q as described herein. In certain embodiments, $R^3$ and $R^4$ are linked together to form $C_{1-6}$ heteroalkylene, optionally substituted with one, two, three, four, or five substituents Q as described herein. In certain embodiments, $R^3$ and $R^4$ are linked together to form $C_{2-6}$ alkenylene, optionally substituted with one, two, three, four, or five substituents Q as described herein. In certain embodiments, $R^3$ and $R^4$ are linked together to form $C_{2-6}$ heteroalkenylene, optionally substituted with one, two, three, four, or five substituents Q as described herein.

In certain embodiments, $R^6$ is hydrogen. In certain embodiments, $R^6$ is $C_{1-6}$ alkyl, optionally substituted with one, two, three, four, or five substituents Q as described herein. In certain embodiments, $R^6$ is $C_{1-6}$ alkyl, optionally substituted with one or more, in one embodiment, one, two, or three, halo. In certain embodiments, $R^6$ is $C_{1-6}$ alkyl, optionally substituted with one or more, in one embodiment, one, two, or three, fluoro. In certain embodiments, $R^6$ is methyl, fluoromethyl, difluoromethyl, or trifluoromethyl. In certain embodiments, $R^6$ is difluoromethyl. In certain embodiments, $R^6$ is —S—$C_{1-6}$ alkyl, wherein the alkyl is optionally substituted with one, two, three, four, or five substituents Q as described herein. In certain embodiments, $R^6$ is —S(O)—$C_{1-6}$ alkyl, wherein the alkyl is optionally substituted with one, two, three, four, or five substituents Q as described herein. In certain embodiments, $R^6$ is —SO$_2$—$C_{1-6}$ alkyl, wherein the alkyl is optionally substituted with one, two, three, four, or five substituents Q as described herein.

In certain embodiments, $R^{5a}$ is hydrogen. In certain embodiments, $R^{5a}$ is not hydrogen. In certain embodiments, $R^{5a}$ is halo. In certain embodiments, $R^{5a}$ is fluoro, chloro, bromo, or iodo. In certain embodiments, $R^{5a}$ is $C_{1-6}$ alkyl, optionally substituted with one, two, three, four, or five substituents Q as described herein. In certain embodiments, $R^{5a}$ is methyl, ethyl, propyl, or butyl, each optionally substituted with one, two, three, four, or five substituents Q as described herein. In certain embodiments, $R^{5a}$ is methyl, ethyl, n-propyl, isopropyl, n-butyl, isobutyl, or t-butyl. In certain embodiments, $R^{5a}$ is methyl. In certain embodiments, $R^{5a}$ is $C_{2-6}$ alkenyl, optionally substituted with one, two, three, four, or five substituents Q as described herein. In certain embodiments, $R^{5a}$ is $C_{2-6}$ alkynyl, optionally substituted with one, two, three, four, or five substituents Q as described herein. In certain embodiments, $R^{5a}$ is $C_{3-10}$ cycloalkyl, optionally substituted with one, two, three, four, or five substituents Q as described herein. In certain embodiments, $R^{5a}$ is $C_{3-7}$ cycloalkyl, optionally substituted with one, two, three, four, or five substituents Q as described herein. In certain embodiments, $R^{5a}$ is $C_{6-14}$ aryl, optionally substituted with one, two, three, four, or five substituents Q as described herein. In certain embodiments, $R^{5a}$ is $C_{7-15}$ aralkyl, optionally substituted with one, two, three, four, or five substituents Q as described herein. In certain embodiments, $R^{5a}$ is heteroaryl, optionally substituted with one, two, three, four, or five substituents Q as described herein. In certain embodiments, $R^{5a}$ is heterocyclyl, optionally substituted with one, two, three, four, or five substituents Q as described herein.

In certain embodiments, $R^{5a}$ is —C(O)$R^{1a}$, wherein $R^{1a}$ is as defined herein. In certain embodiments, $R^{5a}$ is —C(O)O$R^{1a}$, wherein $R^{1a}$ is as defined herein. In certain embodiments, $R^{5a}$ is —C(O)O$R^{1a}$, wherein $R^{1a}$ is $C_{1-6}$ alkyl, optionally substituted with one, two, three, four, or five substituents Q as described herein. In certain embodiments, $R^{5a}$ is —C(O)OCH$_3$. In certain embodiments, $R^{5a}$ is —C(O)NR$^{1b}$R$^{1c}$, wherein R$^{1b}$ and R$^{1c}$ are each as defined herein. In certain embodiments, $R^{5a}$ is —C(NR$^{1a}$)NR$^{1b}$R$^{1c}$, wherein R$^{1a}$, R$^{1b}$, and R$^{1c}$ are each as defined herein. In certain embodiments, $R^{5a}$ is OR$^{1a}$, wherein R$^{1a}$ is as defined herein. In certain embodiments, $R^{5a}$ is —OC(O)R$^{1a}$, wherein R$^{1a}$ is as defined herein. In certain embodiments, $R^{5a}$ is —OC(O)OR$^{1a}$, wherein R$^{1a}$ is as defined herein. In certain embodiments, $R^{5a}$ is —OC(O)NR$^{1b}$R$^{1c}$, wherein R$^{1b}$ and R$^{1c}$ are each as defined herein. In certain embodiments, $R^{5a}$ is —OC(=NR$^{1a}$)NR$^{1b}$R$^{1c}$, wherein R$^{1a}$, R$^{1b}$, and R$^{1c}$ are each as defined herein. In certain embodiments, $R^{5a}$ is —OS(O)R$^{1a}$, wherein R$^{1a}$ is as defined herein. In certain embodiments, $R^{5a}$ is —OS(O)$_2$R$^{1a}$, wherein R$^{1a}$ is as defined herein. In certain embodiments, $R^{5a}$ is —OS(O)NR$^{1b}$R$^{1c}$, wherein R$^{1b}$ and R$^{1c}$ are each as defined herein. In certain embodiments, $R^{5a}$ is —OS(O)$_2$NR$^{1b}$R$^{1c}$, wherein R$^{1b}$ and R$^{1c}$ are each as defined herein. In certain embodiments, $R^{5a}$ is —NR$^{1b}$R$^{1c}$, wherein R$^{1b}$ and R$^{1c}$ are each as defined herein. In certain embodiments, $R^{5a}$ is amino (—NH$_2$). In certain embodiments, $R^{5a}$ is —NR$^{1a}$C(O)R$^{1d}$, wherein R$^{1a}$ and R$^{1d}$ are each as defined herein. In certain embodiments, $R^{5a}$ is —NR$^{1a}$C(O)OR$^{1d}$, wherein R$^{1a}$ and R$^{1d}$ are each as defined herein. In certain embodiments, $R^{5a}$ is —NR$^{1a}$C(O)NR$^{1b}$R$^{1c}$, wherein R$^{1a}$, R$^{1b}$, and R$^{1c}$ are each as defined herein. In certain embodiments, $R^{5a}$ is —NR$^{1a}$C(=NR$^{1}$)NR$^{1b}$R$^{1c}$, wherein R$^{1a}$, R$^{1b}$, R$^{1c}$, and R$^{1d}$ are each as defined herein. In certain embodiments, $R^{5a}$ is —NR$^{1a}$S(O)R$^{1d}$, wherein R$^{1a}$ and R$^{1d}$ are each as defined herein. In certain embodiments, $R^{5a}$ is —NR$^{1a}$S(O)$_2$R$^{1d}$, wherein R$^{1a}$ and R$^{1d}$ are each as defined herein. In certain embodiments, $R^{5a}$ is —NR$^{1a}$S(O)NR$^{1b}$R$^{1c}$, wherein R$^{1a}$, R$^{1b}$, and R$^{1c}$ are each as defined herein. In certain embodiments, $R^{5a}$ is —NR$^{1a}$S(O)$_2$NR$^{1b}$R$^{1c}$, wherein R$^{1a}$, R$^{1b}$ and R$^{1c}$ are each as defined herein. In certain embodiments, $R^{5a}$ is —SR$^{1a}$, wherein R$^{1a}$ is as defined herein. In certain embodiments, $R^{5a}$ is —S(O)R$^{1a}$, wherein R$^{1a}$ is as defined herein. In certain embodiments, $R^{5a}$ is —S(O)$_2$R$^{1a}$, wherein R$^{1d}$ is as defined herein. In certain embodiments, $R^{5a}$ is —S(O)NR$^{1b}$R$^{1c}$, wherein R$^{1b}$ and R$^{1c}$ are each as defined herein. In certain embodiments, $R^{5a}$ is —S(O)$_2$NR$^{1b}$R$^{1c}$; wherein R$^{1b}$ and R$^{1c}$ are each as defined herein.

In certain embodiments, $R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl, each of which is optionally substituted with one, two, three, four, or five substituents Q; or (c) —C(O)R$^{1d}$, —C(O)OR$^{1d}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$_{1a}$C(O)NR$^{1b}$R$^{1c}$, NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$. In certain embodiments, $R^{5a}$ is (a) hydrogen or halo; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, or heteroaryl, each of which is optionally substituted with one, two, three, four, or five substituents Q.

In certain embodiments, $R^{5b}$ is halo. In certain embodiments, $R^{5b}$ is fluoro, chloro, bromo, or iodo. In certain embodiments, $R^{5b}$ is $C_{1-6}$ alkyl, optionally substituted with one, two, three, four, or five substituents Q as described herein. In certain embodiments, $R^{5b}$ is methyl, ethyl, propyl, or butyl, each optionally substituted with one, two, three, four, or five substituents Q as described herein. In certain embodiments, $R^{5b}$ is methyl, ethyl, n-propyl, isopropyl, n-butyl, isobutyl, or t-butyl. In certain embodiments, $R^{5b}$ is methyl. In certain embodiments, $R^{5b}$ is $C_{2-6}$ alkenyl, optionally substituted with one, two, three, four, or five substituents Q as described herein. In certain embodiments, $R^{5b}$ is $C_{2-6}$ alkynyl, optionally substituted with one, two, three, four, or five substituents Q as described herein. In certain embodiments, $R^{5b}$ is $C_{3-10}$ cycloalkyl, optionally substituted with one, two, three, four, or five substituents Q as described herein. In certain embodiments, $R^{5b}$ is $C_{3-7}$ cycloalkyl, optionally substituted with one, two, three, four, or five substituents Q as described herein. In certain embodiments, $R^{5b}$ is $C_{6-14}$ aryl, optionally substituted with one, two, three, four, or five substituents Q as described herein. In certain embodiments, $R^{5b}$ is $C_{7-15}$ aralkyl, optionally substituted with one, two, three, four, or five substituents Q as described herein. In certain embodiments, $R^{5b}$ is heteroaryl, optionally substituted with one, two, three, four, or five substituents Q as described herein. In certain embodiments, $R^{5b}$ is heterocyclyl, optionally substituted with one, two, three, four, or five substituents Q as described herein. In certain embodiments, $R^{5b}$ is not heterocyclyl.

In certain embodiments, $R^{5b}$ is —C(O)$R^{1a}$, wherein $R^{1a}$ is as defined herein. In certain embodiments, $R^{5b}$ is —C(O)O$R^{1a}$, wherein $R^{1a}$ is as defined herein. In certain embodiments, $R^{5b}$ is C(O)O$R^{1a}$, wherein $R^{1a}$ is $C_{1-6}$ alkyl, optionally substituted with one, two, three, four, or five substituents Q as described herein. In certain embodiments, $R^{5b}$ is —C(O)OCH$_3$. In certain embodiments, $R^{5b}$ is —C(O)N$R^{1b}R^{1c}$, wherein $R^{1b}$ and $R^{1c}$ are each as defined herein. In certain embodiments, $R^{5b}$ is —C(N$R^{1a}$)N$R^{1b}R^{1c}$, wherein $R^{1a}$, $R^{1b}$, and $R^{1c}$ are each as defined herein. In certain embodiments, $R^{5b}$ is —O$R^{1a}$, wherein $R^{1a}$ is as defined herein. In certain embodiments, $R^{5b}$ is —OC(O)$R^{1a}$, wherein $R^{1a}$ is as defined herein. In certain embodiments, $R^{5b}$ is —OC(O)O$R^{1a}$, wherein $R^{1a}$ is as defined herein. In certain embodiments, $R^{5b}$ is —OC(O)N$R^{1b}R^{1c}$, wherein $R^{1b}$ and $R^{1c}$ are each as defined herein. In certain embodiments, $R^{5b}$ is —OC(=N$R^{1a}$)N$R^{1b}R^{1c}$, wherein $R^{1a}$, $R^{1b}$, and $R^{1c}$ are each as defined herein. In certain embodiments, $R^{5b}$ is —OS(O)$R^{1a}$, wherein $R^{1a}$ is as defined herein. In certain embodiments, $R^{5b}$ is —OS(O)$_2R^{1a}$, wherein $R^{1a}$ is as defined herein. In certain embodiments, $R^{5b}$ is —OS(O)N$R^{1b}R^{1c}$, wherein $R^{1b}$ and $R^{1c}$ are each as defined herein. In certain embodiments, $R^{5b}$ is —OS(O)$_2$N$R^{1b}R^{1c}$, wherein $R^{1b}$ and $R^{1c}$ are each as defined herein. In certain embodiments, $R^{5b}$ is —N$R^{1b}R^{1c}$, wherein $R^{1b}$ and $R^{1c}$ are each as defined herein. In certain embodiments, $R^{5b}$ is amino (—NH$_2$). In certain embodiments, $R^{5b}$ is —N$R^{1a}$C(O)$R^{1d}$, wherein $R^{1a}$ and $R^{1d}$ are each as defined herein. In certain embodiments, $R^{5b}$ is —N$R^{1a}$C(O)O$R^{1d}$, wherein $R^{1a}$ and $R^{1d}$ are each as defined herein. In certain embodiments, $R^{5b}$ is —N$R^{1a}$C(O)N$R^{1b}R^{1c}$, wherein $R^{1a}$, $R^{1b}$, and $R^{1c}$ are each as defined herein. In certain embodiments, $R^{5b}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5b}$ is —N$R^{1a}$S(O)$R^{1d}$, wherein $R^{1a}$ and $R^{1d}$ are each as defined herein. In certain embodiments, $R^{5b}$ is —N$R^{1a}$S(O)$_2R^{1d}$, wherein $R^{1a}$ and $R^{1d}$ are each as defined herein. In certain embodiments, $R^{5b}$ is —N$R^{1a}$S(O)N$R^{1b}R^{1c}$, wherein $R^{1a}$, $R^{1b}$, and $R^{1c}$ are each as defined herein. In certain embodiments, $R^{5b}$ is —N$R^{1a}$S(O)$_2$N$R^{1b}R^{1c}$, wherein $R^{1a}$, $R^{1b}$, and $R^{1c}$ are each as defined herein. In certain embodiments, $R^{5b}$ is S$R^{1a}$, wherein $R^{1a}$ is as defined herein. In certain embodiments, $R^{5b}$ is —S(O)$R^{1a}$, wherein $R^{1a}$ is as defined herein. In certain embodiments, $R^{5b}$ is —S(O)$_2R^{1a}$, wherein $R^{1a}$ is as defined herein. In certain embodiments, $R^{5b}$ is —S(O)N$R^{1b}R^{1c}$, wherein $R^{1b}$ and $R^{1c}$ are each as defined herein. In certain embodiments, $R^{5b}$ is —S(O)$_2$N$R^{1b}R^{1c}$; wherein $R^{1b}$ and $R^{1c}$ are each as defined herein.

In certain embodiments, $R^{5a}$ and $R^{5b}$ are each independently methyl, ethyl, n-propyl, isopropyl, n-butyl, isobutyl, or t-butyl, each optionally substituted with one, two, three, four, or five substituents Q as described herein. In certain embodiments, $R^{5a}$ and $R^{5b}$ are each independently methyl, ethyl, n-propyl, isopropyl, n-butyl, isobutyl, or t-butyl, each optionally substituted with one or more halo. In certain embodiments, $R^{5a}$ and $R^{5b}$ are each independently methyl, ethyl, n-propyl, isopropyl, n-butyl, isobutyl, or t-butyl. In certain embodiments, $R^{5a}$ and $R^{5b}$ are each methyl.

In certain embodiments, $R^{5c}$ is $C_{6-14}$ aryl, optionally substituted with one, two, three, four, or five substituents Q as described herein. In certain embodiments, $R^{5b}$ is $C_{6-14}$ aryl substituted at the 2-position with one substituent Q as described herein. In certain embodiments, $R^{5c}$ is phenyl or naphthyl, each optionally substituted with one, two, three, four, or five substituents Q as described herein. In certain embodiments, $R^{5c}$ is phenyl, naphtha-1-yl, or naphtha-2-yl, each optionally substituted with one, two, three, four, or five substituents Q as described herein. In certain embodiments, $R^{5c}$ is phenyl, 4-chlorophenyl, 4-methoxyphenyl, or naphtha-2-yl. In certain embodiments, $R^{5c}$ is heteroaryl, optionally substituted with one or more substituents as described herein. In certain embodiments, $R^{5c}$ is monocyclic heteroaryl, optionally substituted with one or more substituents as described herein. In certain embodiments, $R^{5c}$ is 5- or 6-membered heteroaryl, optionally substituted with one or more substituents as described herein. In certain embodiments, $R^{5c}$ is bicyclic heteroaryl, optionally substituted with one or more substituents as described herein.

In certain embodiments, $R^{5c}$ is —(C$R^{5f}R^{5g}$)$_n$—(C$_{6-14}$ aryl), wherein the $C_{6-14}$ aryl is optionally substituted with one, two, three, four, or five substituents Q as described herein. In certain embodiments, $R^{5c}$ is benzyl, 2-phenethyl, 3-phenylpropyl, or 4-phenylbutyl, wherein each of the phenyl moiety is optionally substituted with one, two, three, four, or five substituents Q as described herein. In certain embodiments, $R^{5c}$ is benzyl, 2-phenethyl, 3-phenylpropyl, or 4-phenylbutyl. In certain embodiments, $R^{5c}$ is benzyl, fluorobenzyl, chlorobenzyl, bromobenzyl, cyanobenzyl, methylbenzyl, or methoxybenzyl. In certain embodiments, $R^{5c}$ is (naphthalen-1-yl)methyl, (naphthalen-2-yl)methyl 2-(naphthalen-1-yl)ethyl, 2-(naphthalen-2-yl)ethyl, 3-(naphthalen-1-yl)propyl, 3-(naphthalen-2-yl)propyl, 4-(naphthalen-1-yl)butyl, or 4-(naphthalen-2-yl)butyl, wherein each of the naphthyl moiety is optionally substituted with one, two, three, four, or five substituents Q as described herein. In certain embodiments, n is 0 or 1. In one embodiment, n is 1. In one embodiment, n is 1, 2, 3, or 4. In certain embodiments, $R^{5c}$ is —CH$_2$—(C$_{6-14}$ aryl), wherein the $C_{6-14}$ aryl is optionally substituted with one, two, three, four, or five substituents Q as described herein. In certain embodiments, $R^{5c}$ is —C(CH$_3$)$_2$—(C$_{6-14}$ aryl), wherein the $C_{6-14}$ aryl is optionally substituted with one, two, three, four, or five substituents Q as described herein. In certain embodiments, $R^{5c}$ is —CH$_2$-phenyl or —CH$_2$-naphthyl, wherein the phenyl or naphthyl is each optionally substituted with one, two, three, four, or five substituents Q as described herein, such as, e.g., optionally substituted with one or more F, Cl, Br, I, —CN, —CH$_3$, —CF$_3$, —OCH$_3$, or —OCF$_3$. In certain embodiments, $R^{5c}$ is —CH$_2$-phenyl, —CH$_2$-naphtha-1-yl, or —CH$_2$-naphtha-2-yl, wherein the phenyl or naphthyl is each optionally substituted with one, two, three, four, or five substituents Q as described herein, such as, e.g., optionally substituted with one or more F, Cl, Br, I, —CN, —CH$_3$, —CF$_3$, —OCH$_3$, or —OCF$_3$. In certain embodiments, R$^{5c}$ is —CH$_2$-phenyl, —CH$_2$-naphtha-1-yl, or —CH$_2$-naphtha-2-yl, wherein the phenyl or naphthyl is each optionally substituted with one or more F, Cl, Br, I, —CN, —CH$_3$, —CF$_3$, —OCH$_3$, —OCF$_3$. In other embodiments, R$^{5c}$ is —CH$_2$-phenyl, —CH$_2$-naphtha-1-yl, or —CH$_2$-naphtha-2-yl, wherein the phenyl or naphthyl is each optionally substituted with one or more F, Cl, Br, I, —CN, —CH$_3$, —CF$_3$, —OCH$_3$, —OCF$_3$, —O—(C$_{1-4}$ alkylene)-N—(C$_{1-4}$ alkyl)$_2$ (e.g., —O—CH$_2$CH$_2$—N(CH$_3$)$_2$), —O-heterocyclyl (e.g., —O—(N-methylpiperidinyl) or —O-piperidinyl), —O-heteroaryl (e.g., —O-pyridyl), —NH-heterocyclyl (e.g., —N—(N-methylpiperidinyl), —NH—(N-methylpyrrolidinyl), —NH-piperidinyl, or —NH-pyrrolidinyl), —NH-heteroaryl (e.g., —NH-pyridyl), —NCH$_3$-heterocyclyl (e.g., —NCH$_3$—(N-methylpiperidinyl), —NCH$_3$(N-methylpyrrolidinyl), —NCH$_3$-piperidinyl, or —NCH$_3$-pyrrolidinyl), —NCH$_3$-heteroaryl (e.g., —NCH$_3$-pyridyl), heterocyclyl (e.g., piperidinyl, piperazinyl, N-methylpiperidinyl, or N-methylpiperazinyl), or heteroaryl (e.g., pyridyl or imidazolyl). In certain embodiments, R$^{5c}$ is —CH$_2$-phenyl, —C(CH$_3$)$_2$-phenyl, —CH$_2$-(2-methylphenyl), —CH$_2$-(2-methoxyphenyl), —CH$_2$-(2-fluorophenyl), —CH$_2$-(2-chlorophenyl), —CH$_2$-(2-bromophenyl), —CH$_2$-(3-methylphenyl), —CH$_2$-(3-methoxyphenyl), —CH$_2$-(3-fluorophenyl), —CH$_2$-(3-chlorophenyl), —CH$_2$-(3-bromophenyl), —CH$_2$-(4-methylphenyl), —CH$_2$-(4-methoxylphenyl), —CH$_2$-(4-fluorophenyl), —CH$_2$-(4-chlorophenyl), —CH$_2$-(4-bromophenyl), CH$_2$-naphtha-1-yl, or —CH$_2$-naphtha-2-yl.

In certain embodiments, R$^{5c}$ is —(CR$^{5f}$R$^{5g}$)—(C$_{6-14}$ aryl), wherein the C$_{6-14}$ aryl is optionally substituted with one, two, three, four, or five substituents Q as described herein, and wherein R$^{5f}$ and R$^{5g}$ together with the carbon atom to which they are attached form a 3- to 6-membered cycloalkyl or heterocyclyl. In one embodiment, R$^{5c}$ is cyclopropyl-phenyl. In one embodiment, R$^{5c}$ is cyclobutyl-phenyl. In one embodiment, R$^{5c}$ is cyclopentyl-phenyl. In one embodiment, R$^{5c}$ is cyclohexyl-phenyl.

In certain embodiments, R$^{5c}$ is —(CR$^{5f}$R$^{5g}$)$_n$-heteroaryl, wherein the heteroaryl is optionally substituted with one, two, three, four, or five substituents Q as described herein, wherein n is defined elsewhere. In certain embodiments, R$^{5c}$ is —CH$_2$-(monocyclic heteroaryl), wherein the heteroaryl is optionally substituted with one or more substituents as described herein. In certain embodiments, R$^{5c}$ is —CH$_2$-(5- or 6-membered heteroaryl), wherein the heteroaryl is optionally substituted with one or more substituents as described herein. In certain embodiments, R$^{5c}$ is —CH$_2$-(bicyclic heteroaryl), wherein the heteroaryl is optionally substituted with one or more substituents as described herein.

In certain embodiments, R$^{5d}$ is hydrogen. In certain embodiments, R$^{5d}$ is halo. In certain embodiments, R$^{5d}$ is fluoro, chloro, bromo, or iodo. In certain embodiments, R$^{5d}$ is C$_{1-6}$ alkyl, optionally substituted with one, two, three, four, or five substituents Q as described herein. In certain embodiments, R$^{5d}$ is methyl, optionally substituted with one, two, three, four, or five substituents Q as described herein. In certain embodiments, R$^{5d}$ is methyl. In certain embodiments, R$^{5d}$ is methyl, ethyl, propyl, or butyl, each optionally substituted with one, two, three, four, or five substituents Q as described herein. In certain embodiments, R$^{5d}$ is methyl, ethyl, n-propyl, isopropyl, n-butyl, isobutyl, or t-butyl. In certain embodiments, R$^{5d}$ is C$_{2-6}$ alkenyl, optionally substituted with one, two, three, four, or five substituents Q as described herein. In certain embodiments, R$^{5d}$ is C$_{2-6}$ alkynyl, optionally substituted with one, two, three, four, or five substituents Q as described herein. In certain embodiments, R$^{5d}$ is C$_{3-10}$ cycloalkyl, optionally substituted with one, two, three, four, or five substituents Q as described herein. In certain embodiments, R$^{5d}$ is C$_{6-14}$ aryl, optionally substituted with one, two, three, four, or five substituents Q as described herein. In certain embodiments, R$^{5d}$ is C$_{7-15}$ aralkyl, optionally substituted with one, two, three, four, or five substituents Q as described herein. In certain embodiments, R$^{5d}$ is heteroaryl, optionally substituted with one, two, three, four, or five substituents Q as described herein. In certain embodiments, R$^{5d}$ is heterocyclyl, optionally substituted with one, two, three, four, or five substituents Q as described herein.

In certain embodiments, R$^{5d}$ is —C(O)R$^{1a}$, wherein R$^{1a}$ is as defined herein. In certain embodiments, R$^{5d}$ is —C(O)OR$^{1a}$, wherein R$^{1a}$ is as defined herein. In certain embodiments, R$^{5d}$ is —C(O)OR$^{1a}$, wherein R$^{1a}$ is —C$_{1-6}$ alkyl, optionally substituted with one, two, three, four, or five substituents Q as described herein. In certain embodiments, R$^{5d}$ is —C(O)OCH$_3$. In certain embodiments, R$^{5d}$ is —C(O)NR$^{1b}$R$^{1c}$, wherein R$^{1b}$ and R$^{1c}$ are each as defined herein. In certain embodiments, R$^{5d}$ is —C(NR$^{1a}$)NR$^{1b}$R$^{1c}$, wherein R$^{1a}$, R$^{1b}$, and R$^{1c}$ are each as defined herein. In certain embodiments, R$^{5d}$ is —OR$^{1a}$, wherein R$^{1a}$ is as defined herein. In certain embodiments, R$^{5d}$ is —OC(O)R$^{1a}$, wherein R$^{1a}$ is as defined herein. In certain embodiments, R$^{5d}$ is —OC(O)OR$^{1a}$, wherein R$^{1a}$ is as defined herein. In certain embodiments, R$^{5d}$ is —OC(O)NR$^{1b}$R$^{1c}$, wherein R$^{1b}$ and R$^{1c}$ are each as defined herein. In certain embodiments, R$^{5d}$ is —OC(=NR$^{1a}$)NR$^{1b}$R$^{1c}$, wherein R$^{1a}$, R$^{1b}$, and R$^{1c}$ are each as defined herein. In certain embodiments, R$^{5d}$ is —OS(O)R$^{1a}$, wherein R$^{1a}$ is as defined herein. In certain embodiments, R$^{5d}$ is —OS(O)$_2$R$^{1a}$, wherein R$^{1a}$ is as defined herein. In certain embodiments, R$^{5d}$ is —OS(O)NR$^{1b}$R$^{1c}$, wherein R$^{1b}$ and R$^{1c}$ are each as defined herein. In certain embodiments, R$^{5d}$ is —OS(O)$_2$NR$^{1b}$R$^{1c}$, wherein R$^{1b}$ and R$^{1c}$ are each as defined herein. In certain embodiments, R$^{5d}$ is —NR$^{1b}$R$^{1c}$, wherein R$^{1b}$ and R$^{1c}$ are each as defined herein. In certain embodiments, R$^{5d}$ is amino (—NH$_2$). In certain embodiments, R$^{5d}$ is —NR$^{1a}$C(O)R$^{1d}$, wherein R$^{1a}$ and R$^{1d}$ are each as defined herein. In certain embodiments, R$^{5d}$ is —NR$^{1a}$C(O)OR$^{1d}$, wherein R$^{1a}$ and R$^{1d}$ are each as defined herein. In certain embodiments, R$^{5d}$ is —NR$^{1a}$C(O)NR$^{1b}$R$^{1c}$, wherein R$^{1a}$, R$^{1b}$, and R$^{1c}$ are each as defined herein. In certain embodiments, R$^{5d}$ is —NR$^{1a}$C(=NR$^{1d}$)NR$^{1b}$R$^{1c}$, wherein R$^{1a}$, R$^{1b}$, R$^{1c}$, and R$^{1d}$ are each as defined herein. In certain embodiments, R$^{5d}$ is —NR$^{1a}$S(O)R$^{1d}$, wherein R$^{1a}$ and R$^{1d}$ are each as defined herein. In certain embodiments, R$^{5d}$ is —NR$^{1a}$S(O)$_2$R$^{1d}$, wherein R$^{1a}$ and R$^{1d}$ are each as defined herein. In certain embodiments, R$^{5d}$ is —NR$^{1a}$S(O)NR$^{1b}$R$^{1c}$, wherein R$^{1a}$, R$^{1b}$, and R$^{1c}$ are each as defined herein. In certain embodiments, R$^{5d}$ is —NR$^{1a}$S(O)$_2$NR$^{1b}$R$^{1c}$, wherein R$^{1a}$, R$^{1b}$, and R$^{1c}$ are each as defined herein. In certain embodiments, R$^{5d}$ is —SR$^{1a}$, wherein R$^{1a}$ is as defined herein. In certain embodiments, R$^{5d}$ is —S(O)R$^{1a}$, wherein R$^{1a}$ is as defined herein. In certain embodiments, R$^{5d}$ is —S(O)$_2$R$^{1a}$, wherein R$^{1a}$ is as defined herein. In certain embodiments, R$^{5d}$ is —S(O)NR$^{1b}$R$^{1c}$, wherein R$^{1b}$ and R$^{1c}$ are each as defined herein. In certain embodiments, R$^{5d}$ is —S(O)$_2$NR$^{1b}$R$^{1c}$; wherein R$^{1b}$ and R$^{1c}$ are each as defined herein.

In certain embodiments, R$^{5e}$ is hydrogen. In certain embodiments, R$^{5e}$ is halo. In certain embodiments, R$^{5e}$ is fluoro, chloro, bromo, or iodo. In certain embodiments, R$^{5e}$ is C$_{1-6}$ alkyl, optionally substituted with one, two, three, four, or five substituents Q as described herein. In certain embodiments, $R^{5e}$ is methyl, optionally substituted with one, two, three, four, or five substituents Q as described herein. In certain embodiments, $R^{5e}$ is methyl. In certain embodiments, $R^{5e}$ is methyl, ethyl, propyl, or butyl, each optionally substituted with one, two, three, four, or five substituents Q as described herein. In certain embodiments, $R^{5e}$ is methyl, ethyl, n-propyl, isopropyl, n-butyl, isobutyl, or t-butyl. In certain embodiments, $R^{5e}$ is $C_{2-6}$ alkenyl, optionally substituted with one, two, three, four, or five substituents Q as described herein. In certain embodiments, $R^{5c}$ is $C_{2-6}$ alkynyl, optionally substituted with one, two, three, four, or five substituents Q as described herein. In certain embodiments, $R^{5c}$ is $C_{3-10}$ cycloalkyl, optionally substituted with one, two, three, four, or five substituents Q as described herein. In certain embodiments, $R^{5c}$ is $C_{6-14}$ aryl, optionally substituted with one, two, three, four, or five substituents Q as described herein. In certain embodiments, $R^{5c}$ is $C_{7-15}$ aralkyl, optionally substituted with one, two, three, four, or five substituents Q as described herein. In certain embodiments, $R^{5c}$ is heteroaryl, optionally substituted with one, two, three, four, or five substituents Q as described herein. In certain embodiments, $R^{5c}$ is heterocyclyl, optionally substituted with one, two, three, four, or five substituents Q as described herein.

In certain embodiments, $R^{5c}$ is —C(O)$R^{1a}$, wherein $R^{1a}$ is as defined herein. In certain embodiments, $R^{5c}$ is —C(O)O$R^{1a}$, wherein $R^{1a}$ is as defined herein. In certain embodiments, $R^{5c}$ is —C(O)O$R^{1a}$, wherein $R^{1a}$ is $C_{1-6}$ alkyl, optionally substituted with one, two, three, four, or five substituents Q as described herein. In certain embodiments, $R^{5c}$ is —C(O)OCH$_3$. In certain embodiments, $R^{5c}$ is —C(O)N$R^{1b}R^{1c}$, wherein $R^{1b}$ and $R^{1c}$ are each as defined herein. In certain embodiments, $R^{5c}$ is —C(N$R^{1a}$)N$R^{1b}R^{1c}$, wherein $R^{1a}$, $R^{1b}$, and $R^{1c}$ are each as defined herein. In certain embodiments, $R^{5c}$ is —O$R^{1a}$, wherein $R^{1a}$ is as defined herein. In certain embodiments, $R^{5c}$ is —OC(O)$R^{1a}$, wherein $R^{1a}$ is as defined herein. In certain embodiments, $R^{5e}$ is —OC(O)O$R^{1a}$, wherein $R^{1a}$ is as defined herein. In certain embodiments, $R^{5e}$ is —OC(O)N$R^{1b}R^{1c}$, wherein $R^{1b}$ and $R^{1c}$ are each as defined herein. In certain embodiments, $R^{5e}$ is —OC(=N$R^{1a}$)N$R^{1b}R^{1c}$, wherein $R^{1a}$, $R^{1b}$, and $R^{1c}$ are each as defined herein. In certain embodiments, $R^{5e}$ is —OS(O)$R^{1a}$, wherein $R^{1a}$ is as defined herein. In certain embodiments, $R^{5c}$ is —OS(O)$_2R^{1a}$, wherein $R^{1a}$ is as defined herein. In certain embodiments, $R^{5c}$ is —OS(O)N$R^{1b}R^{1c}$, wherein $R^{1b}$ and $R^{1c}$ are each as defined herein. In certain embodiments, $R^{5c}$ is —OS(O)$_2$N$R^{1b}R^{1c}$, wherein $R^{1b}$ and $R^{1c}$ are each as defined herein. In certain embodiments, $R^{5c}$ is —N$R^{1b}R^{1c}$, wherein $R^{1b}$ and $R^{1c}$ are each as defined herein. In certain embodiments, $R^{5c}$ is amino (—NH$_2$). In certain embodiments, $R^{5e}$ is —N$R^{1a}$C(O)$R^{1d}$, wherein $R^{1a}$ and $R^{1d}$ are each as defined herein. In certain embodiments, $R^{5e}$ is —N$R^{1a}$C(O)O$R^{1d}$, wherein $R^{1a}$ and $R^{1d}$ are each as defined herein. In certain embodiments, $R^{5e}$ is —N$R^{1a}$C(O)N$R^{1b}R^{1c}$, wherein $R^{1a}$, $R^{1b}$, and $R^{1c}$ are each as defined herein. In certain embodiments, $R^{5e}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5e}$ is —N$R^{1a}$S(O)$R^{1d}$, wherein $R^{1a}$ and $R^{1d}$ are each as defined herein. In certain embodiments, $R^{5e}$ is —N$R^{1a}$S(O)$_2R^{1d}$, wherein $R^{1a}$ and $R^{1d}$ are each as defined herein. In certain embodiments, $R^{5e}$ is —N$R^{1a}$S(O)N$R^{1b}R^{1c}$, wherein $R^{1a}$, $R^{1b}$, and $R^{1c}$ are each as defined herein. In certain embodiments, $R^{5e}$ is —N$R^{1a}$S(O)$_2$N$R^{1b}R^{1c}$, wherein $R^{1a}$, $R^{1b}$, and $R^{1c}$ are each as defined herein. In certain embodiments, $R^{5e}$ is —S$R^{1a}$, wherein $R^{1a}$ is as defined herein. In certain embodiments, $R^{5c}$ is —S(O)$R^{1a}$, wherein $R^{1a}$ is as defined herein. In certain embodiments, $R^{5c}$ is —S(O)$_2R^{1a}$, wherein $R^{1a}$ is as defined herein. In certain embodiments, $R^{5c}$ is —S(O)N$R^{1b}R^{1c}$, wherein $R^{1b}$ and $R^{1c}$ are each as defined herein. In certain embodiments, $R^{5c}$ is —S(O)$_2$N$R^{1b}R^{1c}$; wherein $R^{1b}$ and $R^{1c}$ are each as defined herein.

In certain embodiments, $R^{5f}$ is hydrogen. In certain embodiments, $R^{5f}$ is halo. In certain embodiments, $R^{5f}$ is fluoro, chloro, bromo, or iodo. In certain embodiments, $R^{5f}$ is $C_{1-6}$ alkyl, optionally substituted with one, two, three, four, or five substituents Q as described herein. In certain embodiments, $R^{5f}$ is methyl, optionally substituted with one, two, three, four, or five substituents Q as described herein. In certain embodiments, $R^{5f}$ is methyl. In certain embodiments, $R^{5f}$ is methyl, ethyl, propyl, or butyl, each optionally substituted with one, two, three, four, or five substituents Q as described herein. In certain embodiments, $R^{5f}$ is methyl, ethyl, n-propyl, isopropyl, n-butyl, isobutyl, or t-butyl. In certain embodiments, $R^{5f}$ is $C_{2-6}$ alkenyl, optionally substituted with one, two, three, four, or five substituents Q as described herein. In certain embodiments, $R^{5f}$ is $C_{2-6}$ alkynyl, optionally substituted with one, two, three, four, or five substituents Q as described herein. In certain embodiments, $R^{5f}$ is $C_{3-10}$ cycloalkyl, optionally substituted with one, two, three, four, or five substituents Q as described herein. In certain embodiments, $R^{5f}$ is $C_{6-14}$ aryl, optionally substituted with one, two, three, four, or five substituents Q as described herein. In certain embodiments, $R^{5f}$ is $C_{7-15}$ aralkyl, optionally substituted with one, two, three, four, or five substituents Q as described herein. In certain embodiments, $R^{5f}$ is heteroaryl, optionally substituted with one, two, three, four, or five substituents Q as described herein. In certain embodiments, $R^{5f}$ is heterocyclyl, optionally substituted with one, two, three, four, or five substituents Q as described herein.

In certain embodiments, $R^{5f}$ is 13 C(O)$R^{1a}$, wherein $R^{1a}$ is as defined herein. In certain embodiments, $R^{5f}$ is —C(O)O$R^{1a}$, wherein $R^{1a}$ is as defined herein. In certain embodiments, $R^{5f}$ is —C(O)O$R^{1a}$, wherein $R^{1a}$ is $C_{1-6}$ alkyl, optionally substituted with one, two, three, four, or five substituents Q as described herein. In certain embodiments, $R^{5f}$ is —C(O)OCH$_3$. In certain embodiments, $R^{5f}$ is —C(O)N$R^{1a}$, wherein $R^{1b}$ and $R^{1c}$ are each as defined herein. In certain embodiments, $R^{5f}$ is —C(N$R^{1a}$)N$R^{1b}R^{1c}$, wherein $R^{1a}$, $R^{1b}$, and $R^{1c}$ are each as defined herein. In certain embodiments, $R^{5f}$ is —O$R^{1a}$, wherein $R^{1a}$ is as defined herein. In certain embodiments, $R^{5f}$ is —OC(O)$R^{1a}$, wherein $R^{1a}$ is as defined herein. In certain embodiments, $R^{5f}$ is —OC(O)O$R^{1a}$, wherein $R^{1a}$ is as defined herein. In certain embodiments, $R^{5f}$ is —OC(O)N$R^{1b}R^{1c}$, wherein $R^{1b}$ and $R^{1c}$ are each as defined herein. In certain embodiments, $R^{5f}$ is —OC(=N$R^{1a}$)N$R^{1b}R^{1c}$, wherein $R^{1a}$, $R^{1b}$, and $R^{1c}$ are each as defined herein. In certain embodiments, $R^{5f}$ is —OS(O)$R^{1a}$, wherein $R^{1a}$ is as defined herein. In certain embodiments, $R^{5f}$ is —OS(O)$_2R^{1a}$, wherein $R^{1a}$ is as defined herein. In certain embodiments, $R^{5f}$ is —OS(O)N$R^{1b}R^{1c}$, wherein $R^{1b}$ and $R^{1c}$ are each as defined herein. In certain embodiments, $R^{5f}$ is —OS(O)$_2$N$R^{1b}R^{1c}$, wherein $R^{1b}$ and $R^{1c}$ are each as defined herein. In certain embodiments, $R^{5f}$ is —N$R^{1b}R^{1c}$, wherein $R^{1b}$ and $R^{1c}$ are each as defined herein. In certain embodiments, $R^{5f}$ is amino (—NH$_2$). In certain embodiments, $R^{5f}$ is —N$R^{1a}$C(O)$R^{1d}$, wherein $R^{1a}$ and $R^{1d}$ are each as defined herein. In certain embodiments, $R^{5f}$ is —N$R^{1a}$C(O)O$R^{1d}$, wherein $R^{1a}$ and $R^{1d}$ are each as defined herein. In certain embodiments, $R^{5f}$ is —N$R^{1a}$C(O)N$R^{1b}R^{1c}$, wherein $R^{1a}$, $R^{1b}$, and $R^{1c}$ are each as defined herein. In certain embodiments, $R^{5f}$ is —N$R^{1a}$C(=N$R^{1d}$)N$R^{1b}R^{1c}$, wherein $R^{1a}$, $R^{1b}$, $R^{1c}$, and $R^{1d}$ are each as defined herein. In certain embodiments, $R^{5f}$ is $-NR^{1a}S(O)R^{1d}$, wherein $R^{1a}$ and $R^{1d}$ are each as defined herein. In certain embodiments, $R^{5f}$ is $-NR^{1a}S(O)_2R^{1d}$, wherein $R^{1a}$ and $R^{1d}$ are each as defined herein. In certain embodiments, $R^{5f}$ is $-NR^{1a}S(O)NR^{1b}R^{1c}$, wherein $R^{1a}$, $R^{1b}$, and $R^{1c}$ are each as defined herein. In certain embodiments, $R^{5f}$ is $-NR^{1a}S(O)_2NR^{1b}R^{1c}$, wherein $R^{1a}$, $R^{1b}$ and $R^{1c}$ are each as defined herein. In certain embodiments, $R^{5f}$ is $-SR^{1a}$, wherein $R^{1a}$ is as defined herein. In certain embodiments, $R^{5f}$ is $-S(O)R^{1a}$, wherein $R^{1a}$ is as defined herein. In certain embodiments, $R^{5f}$ is $-S(O)_2R^{1a}$, wherein $R^{1a}$ is as defined herein. In certain embodiments, $R^{5f}$ is $-S(O)NR^{1b}R^{1c}$, wherein $R^{1b}$ and $R^{1c}$ are each as defined herein. In certain embodiments, $R^{5f}$ is $-S(O)_2NR^{1b}R^{1c}$; wherein $R^{1b}$ and $R^{1c}$ are each as defined herein.

In certain embodiments, $R^{5g}$ is hydrogen. In certain embodiments, $R^{5g}$ is halo. In certain embodiments, $R^{5g}$ is fluoro, chloro, bromo, or iodo. In certain embodiments, $R^{5g}$ is $C_{1-6}$ alkyl, optionally substituted with one, two, three, four, or five substituents Q as described herein. In certain embodiments, $R^{5g}$ is methyl, optionally substituted with one, two, three, four, or five substituents Q as described herein. In certain embodiments, $R^{5g}$ is methyl. In certain embodiments, $R^{5g}$ is methyl, ethyl, propyl, or butyl, each optionally substituted with one, two, three, four, or five substituents Q as described herein. In certain embodiments, $R^{5g}$ is methyl, ethyl, n-propyl, isopropyl, n-butyl, isobutyl, or t-butyl. In certain embodiments, $R^{5g}$ is $C_{2-6}$ alkenyl, optionally substituted with one, two, three, four, or five substituents Q as described herein. In certain embodiments, $R^{5g}$ is $C_{2-6}$ alkynyl, optionally substituted with one, two, three, four, or five substituents Q as described herein. In certain embodiments, $R^{5g}$ is $C_{3-10}$ cycloalkyl, optionally substituted with one, two, three, four, or five substituents Q as described herein. In certain embodiments, $R^{5g}$ is $C_{6-14}$ aryl, optionally substituted with one, two, three, four, or five substituents Q as described herein. In certain embodiments, $R^{5g}$ is $C_{7-15}$ aralkyl, optionally substituted with one, two, three, four, or five substituents Q as described herein. In certain embodiments, $R^{5g}$ is heteroaryl, optionally substituted with one, two, three, four, or five substituents Q as described herein. In certain embodiments, $R^{5g}$ is heterocyclyl, optionally substituted with one, two, three, four, or five substituents Q as described herein.

In certain embodiments, $R^{5g}$ is $-C(O)R^{1a}$, wherein $R^{1a}$ is as defined herein. In certain embodiments, $R^{5g}$ is $-C(O)OR^{1d}$, wherein $R^{1d}$ is as defined herein. In certain embodiments, $R^{5g}$ is $-C(O)OR^{1d}$, wherein $R^{1a}$ is $C_{1-6}$ alkyl, optionally substituted with one, two, three, four, or five substituents Q as described herein. In certain embodiments, $R^{5g}$ is $-C(O)OCH_3$. In certain embodiments, $R^{5g}$ is $-C(O)NR^{1b}R^{1c}$, wherein $R^{1b}$ and $R^{1c}$ are each as defined herein. In certain embodiments, $R^{5g}$ is $-C(NR^{1a})NR^{1b}R^{1c}$, wherein $R^{1a}$, $R^{1b}$, and $R^{1c}$ are each as defined herein. In certain embodiments, $R^{5g}$ is $-OR^{1a}$, wherein $R^{1a}$ is as defined herein. In certain embodiments, $R^{5g}$ is $-OC(O)R^{1d}$, wherein $R^{1a}$ is as defined herein. In certain embodiments, $R^{5g}$ is $-OC(O)OR^{1a}$, wherein $R^{1a}$ is as defined herein. In certain embodiments, $R^{5g}$ is $-OC(O)NR^{1b}R^{1c}$, wherein $R^{1b}$ and $R^{1c}$ are each as defined herein. In certain embodiments, $R^{5g}$ is $-OC(=NR^{1a})NR^{1b}R^{1c}$, wherein $R^{1a}$, $R^{1b}$, and $R^{1c}$ are each as defined herein. In certain embodiments, $R^{5g}$ is $-OS(O)R^{1d}$, wherein $R^{1a}$ is as defined herein. In certain embodiments, $R^{5g}$ is $-OS(O)_2R^{1d}$, wherein $R^{1d}$ is as defined herein. In certain embodiments, $R^{5g}$ is $-OS(O)NR^{1b}R^{1c}$, wherein $R^{1b}$ and $R^{1c}$ are each as defined herein. In certain embodiments, $R^{5g}$ is $-OS(O)_2NR^{1b}R^{1c}$, wherein $R^{1b}$ and $R^{1c}$ are each as defined herein. In certain embodiments, $R^{5g}$ is $-NR^{1b}R^{1c}$, wherein $R^{1b}$ and $R^{1c}$ are each as defined herein. In certain embodiments, $R^{5g}$ is amino ($NH_2$). In certain embodiments, $R^{5g}$ is $NR^{1d}C(O)R^{1d}$, wherein $R^{1a}$ and $R^{1d}$ are each as defined herein. In certain embodiments, $R^{5g}$ is $-NR^{1d}C(O)OR^{1d}$, wherein $R^{1d}$ and $R^{1d}$ are each as defined herein. In certain embodiments, $R^{5g}$ is $-NR^{1a}C(O)NR^{1b}R^{1c}$, wherein $R^{1a}$, $R^{1b}$, and $R^{1c}$ are each as defined herein. In certain embodiments, $R^{5g}$ is $-NR^{1a}C(=NR^{1d})NR^{1b}R^{1c}$, wherein $R^{1a}$, $R^{1b}$, $R^{1c}$, and $R^{1d}$ are each as defined herein. In certain embodiments, $R^{5g}$ is $-NR^{1a}S(O)R^{1d}$, wherein $R^{1a}$ and $R^{1d}$ are each as defined herein. In certain embodiments, $R^{5g}$ is $NR^{1a}S(O)_2R^{1d}$, wherein $R^{1a}$ and $R^{1d}$ are each as defined herein. In certain embodiments, $R^{5g}$ is $-NR^{1a}S(O)NR^{1b}R^{1c}$, wherein $R^{1a}$, $R^{1b}$, and $R^{1c}$ are each as defined herein. In certain embodiments, $R^{5g}$ is $-NR^{1a}S(O)_2NR^{1b}R^{1c}$, where in $R^{1a}$, $R^{1b}$, and $R^{1c}$ are each as defined herein. In certain embodiments, $R^{5g}$ is $-SR^{1a}$, wherein $R^{1a}$ is as defined herein. In certain embodiments, $R^{5g}$ is $-S(O)R^{1a}$, wherein $R^{1a}$ is as defined herein. In certain embodiments, $R^{5g}$ is $-S(O)_2R^{1a}$, wherein $R^{1a}$ is as defined herein. In certain embodiments, $R^{5g}$ is $-S(O)NR^{1b}R^{1c}$, wherein $R^{1b}$ and $R^{1c}$ are each as defined herein. In certain embodiments, $R^{5g}$ is $-S(O)_2NR^{1b}R^{1c}$; wherein $R^{1b}$ and $R^{1c}$ are each as defined herein.

In certain embodiments, when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a $C_{3-7}$ cycloalkyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopropyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclobutyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopentyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclohexyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cycloheptyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a cyclopropyl.

In certain embodiments, when one occurrence of $R^{5f}$ and one occurrence of $R^{5g}$ are attached to the same carbon atom, the $R^{5f}$ and $R^{5g}$ together with the carbon atom to which they are attached form a heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 3-membered heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 4-membered heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 5-membered heterocyclyl, optionally substituted with one, two, three, four, or five substituents Q as described herein. In certain embodiments, when one occurrence of $R^{5f}$ and one occurrence of $R^{5g}$ are attached to the same carbon atom, the $R^{5f}$ and $R^{5g}$ together with the carbon atom to which they are attached form a 6-membered heterocyclyl, optionally substituted with one, two, three, four, or five substituents Q as described herein.

In certain embodiments, $R^{7a}$ is hydrogen. In certain embodiments, $R^{7a}$ is cyano. In certain embodiments, $R^{7a}$ is halo. In certain embodiments, $R^{7a}$ is fluoro, chloro, bromo, or iodo. In certain embodiments, $R^{7a}$ is nitro. In certain embodiments, $R^{7a}$ is $C_{1-6}$ alkyl, optionally substituted with one, two, three, or four substituents $Q^a$ as described herein. In certain embodiments, $R^{7a}$ is $C_{2-6}$ alkenyl, optionally substituted with one, two, three, or four substituents $Q^a$ as described herein. In certain embodiments, $R^{7a}$ is $C_{2-6}$ alkynyl, optionally substituted with one, two, three, or four substituents $Q^a$ as described herein. In certain embodiments, $R^{7a}$ is $C_{3-7}$ cycloalkyl, optionally substituted with one, two, three, or four substituents $Q^a$ as described herein. In certain embodiments, $R^{7a}$ is $C_{3-10}$ cycloalkyl, optionally substituted with one, two, three, or four substituents $Q^a$ as described herein. In certain embodiments, $R^{7a}$ is $C_{6-14}$ aryl, optionally substituted with one, two, three, or four substituents $Q^a$ as described herein. In certain embodiments, $R^{7a}$ is phenyl, optionally substituted with one, two, three, or four substituents $Q^a$ as described herein. In certain embodiments, $R^{7a}$ is phenyl, optionally substituted with one or more substituents, each of which is selected independently from the group consisting of fluoro, chloro, bromo, methyl, and methoxy. In certain embodiments, $R^{7a}$ is phenyl, 2-fluorophenyl, 2-chlorophenyl, 2-bromophenyl, 2-methylphenyl, 2-methoxyphenyl, 3-fluorophenyl, 3-chlorophenyl, 3-methoxyphenyl, 4-florophenyl, 4-chlorophenyl, 4-bromophenyl, 4-methoxyphenyl. In certain embodiments, $R^{7a}$ is $C_7$ aralkyl, optionally substituted with one, two, three, or four substituents $Q^a$ as described herein. In certain embodiments, $R^{7a}$ is heteroaryl, optionally substituted with one, two, three, or four substituents $Q^a$ as described herein. In certain embodiments, $R^{7a}$ is monocyclic heteroaryl, optionally substituted with one, two, three, or four substituents $Q^a$ as described herein. In certain embodiments, $R^{7a}$ is 5-membered heteroaryl, optionally substituted with one, two, three, or four substituents $Q^a$ as described herein. In certain embodiments, $R^{7a}$ is imidazolyl or pyrozolyl, optionally substituted with one, two, three, or four substituents $Q^a$ as described herein. In certain embodiments, $R^{7a}$ is imidazol-1-yl, pyrozol-4-yl, 1-methyl-pyrozol-4-yl, or 2-methylpyrozol-3-yl. In certain embodiments, $R^{7a}$ is 6-membered heteroaryl, optionally substituted with one, two, three, or four substituents $Q^a$ as described herein. In certain embodiments, $R^{7a}$ is pyridinyl, optionally substituted with one, two, three, or four substituents $Q^a$ as described herein. In certain embodiments, $R^{7a}$ is pyridin-2-yl, pyridin-3-yl, pyridin-4-yl, 2-methylpyridin-4-yl, or 2-methoxypyridin-4-yl. In certain embodiments, $R^{7a}$ is heterocyclyl, optionally substituted with one, two, three, or four substituents $Q^a$ as described herein. In certain embodiments, $R^{7a}$ is monocyclic heterocyclyl, optionally substituted with one, two, three, or four substituents $Q^a$ as described herein. In certain embodiments, $R^{7a}$ is 5-membered heterocyclyl, optionally substituted with one, two, three, or four substituents $Q^a$ as described herein. In certain embodiments, $R^{7a}$ is 6-membered heterocyclyl, optionally substituted with one, two, three, or four substituents $Q^a$ as described herein. In certain embodiments, $R^{7a}$ is piperidinyl or piperazinyl, optionally substituted with one, two, three, or four substituents $Q^a$ as described herein. In certain embodiments, $R^{7a}$ is 1-methylpiperidin-4-yl, or 4-methylpiperazin-1-yl.

In certain embodiments, $R^{7a}$ is —C(O)$R^a$, wherein $R^a$ is as defined herein. In certain embodiments, $R^{7a}$ is —C(O)O$R^a$, wherein $R^a$ is as defined herein. In certain embodiments, $R^{7a}$ is —C(O)N$R^bR^c$, wherein $R^b$ and $R^c$ are each as defined herein. In certain embodiments, $R^{7a}$ is —C(N$R^a$)N$R^bR^c$, wherein $R^a$, $R^b$, and $R^c$ are each as defined herein. In certain embodiments, $R^{7a}$ is —O$R^a$, wherein $R^a$ is as defined herein. In certain embodiments, $R^a$ is —O—$C_{1-6}$ alkyl, wherein the alkyl is optionally substituted with one, two, three, or four substituents $Q^a$ as described herein. In certain embodiments, $R^a$ is methoxy, ethoxy, propoxy, isopropoxy, or 3-dimethylaminopropoxy. In certain embodiments, $R^{7a}$ is —OC(O)$R^a$, wherein $R^a$ is as defined herein. In certain embodiments, $R^{7a}$ is —OC(O)O$R^a$, wherein $R^a$ is as defined herein. In certain embodiments, $R^{7a}$ is —OC(O)N$R^bR^c$, wherein $R^b$ and $R^c$ are each as defined herein. In certain embodiments, $R^{7a}$ is —OC(=N$R^a$)N$R^bR^c$, wherein $R^a$, $R^b$, and $R^c$ are each as defined herein. In certain embodiments, $R^{7a}$ is —OS(O)$R^a$, wherein $R^a$ is as defined herein. In certain embodiments, $R^{7a}$ is —OS(O)$_2R^a$, wherein $R^a$ is as defined herein. In certain embodiments, $R^{7a}$ is —OS(O)N$R^bR^c$, wherein $R^b$ and $R^c$ are each as defined herein. In certain embodiments, $R^{7a}$ is —OS(O)$_2$N$R^bR^c$, wherein $R^b$ and $R^c$ are each as defined herein. In certain embodiments, $R^{7a}$ is —N$R^bR^c$, wherein $R^b$ and $R^c$ are each as defined herein. In certain embodiments, $R^{7a}$ is amino (—NH$_2$). In certain embodiments, $R^{7a}$ is —N$R^a$C(O)$R^d$, wherein $R^a$ and $R^d$ are each as defined herein. In certain embodiments, $R^{7a}$ is —N$R^a$C(O)O$R^d$, wherein $R^a$ and $R^d$ are each as defined herein. In certain embodiments, $R^{7a}$ is —N$R^a$C(O)N$R^bR^c$, wherein $R^a$, $R^b$, and $R^c$ are each as defined herein. In certain embodiments, $R^{7a}$ is —N$R^a$C(=N$R^d$)N$R^bR^c$, wherein $R^a$, $R^b$, $R^c$, and $R^d$ are each as defined herein. In certain embodiments, $R^{7a}$ is —N$R^a$S(O)$R^d$, wherein $R^a$ and $R^d$ are each as defined herein. In certain embodiments, $R^{7a}$ is —N$R^a$S(O)$_2R^d$, wherein $R^a$ and $R^d$ are each as defined herein. In certain embodiments, $R^{7a}$ is —N$R^a$S(O)N$R^bR^c$, wherein $R^a$, $R^b$, and $R^c$ are each as defined herein. In certain embodiments, $R^{7a}$ is —N$R^a$S(O)$_2$N$R^bR^c$, wherein $R^a$, $R^b$, and $R^c$ are each as defined herein. In certain embodiments, $R^{7a}$ is —S$R^a$, wherein $R^a$ is as defined herein. In certain embodiments, $R^{7a}$ is —S(O)$R^a$, wherein $R^a$ is as defined herein. In certain embodiments, $R^{7a}$ is —S(O)$_2R^a$, wherein $R^a$ is as defined herein. In certain embodiments, $R^{7a}$ is —S(O)N$R^bR^c$, wherein $R^b$ and $R^c$ are each as defined herein. In certain embodiments, $R^{7a}$ is —S(O)$_2$N$R^bR^c$; wherein $R^b$ and $R^c$ are each as defined herein.

In certain embodiments, $R^{7a}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$. In certain embodiments, $R^{7a}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7b}$ is hydrogen. In certain embodiments, $R^{7b}$ is cyano. In certain embodiments, $R^{7b}$ is halo. In certain embodiments, $R^{7b}$ is fluoro, chloro, bromo, or iodo. In certain embodiments, $R^{7b}$ is nitro. In certain embodiments, $R^{7b}$ is $C_{1-6}$ alkyl, optionally substituted with one, two, three, or four substituents $Q^a$ as described herein. In certain embodiments, $R^{7b}$ is $C_{2-6}$ alkenyl, optionally substituted with one, two, three, or four substituents $Q^a$ as described herein. In certain embodiments, $R^{7b}$ is $C_{2-6}$ alkynyl, optionally substituted with one, two, three, or four substituents $Q^a$ as described herein. In certain embodiments, $R^{7b}$ is $C_{3-10}$ cycloalkyl, optionally substituted with one, two, three, or four substituents $Q^a$ as described herein. In certain embodiments, $R^{7b}$ is $C_{3-7}$ cycloalkyl, optionally substituted with one, two, three, or four substituents $Q^a$ as described herein. In certain embodiments, $R^{7b}$ is $C_{6-14}$ aryl, optionally substituted with one, two, three, or four substituents $Q^a$ as described herein. In certain embodiments, $R^{7b}$ is $C_{7-15}$ aralkyl, optionally substituted with one, two, three, or four substituents $Q^a$ as described herein. In certain embodiments, $R^{7b}$ is heteroaryl, optionally substituted with one, two, three, or four substituents $Q^a$ as described herein. In certain embodiments, $R^{7b}$ is heterocyclyl, optionally substituted with one, two, three, or four substituents $Q^a$ as described herein.

In certain embodiments, $R^{7b}$ is —C(O)$R^a$, wherein $R^a$ is as defined herein. In certain embodiments, $R^{7b}$ is —C(O)O$R^a$, wherein $R^a$ is as defined herein. In certain embodiments, $R^{7b}$ is —C(O)NR$^b$R$^c$, wherein $R^b$ and $R^c$ are each as defined herein. In certain embodiments, $R^{7b}$ is —C(NR$^a$)NR$^b$R$^c$, wherein $R^a$, $R^b$, and $R^c$ are each as defined herein. In certain embodiments, $R^{7b}$ is —OR$^a$, wherein $R^a$ is as defined herein. In certain embodiments, $R^a$ is —O—$C_{1-6}$ alkyl, wherein the alkyl is optionally substituted with one, two, three, or four substituents $Q^a$ as described herein. In certain embodiments, $R^a$ is methoxy, ethoxy, propoxy, isopropoxy, or 3-dimethylaminopropoxy. In certain embodiments, $R^{7b}$ is —OC(O)$R^a$, wherein $R^a$ is as defined herein. In certain embodiments, $R^{7b}$ is —OC(O)O$R^a$, wherein $R^a$ is as defined herein. In certain embodiments, $R^{7b}$ is —OC(O)NR$^b$R$^c$, wherein $R^b$ and $R^c$ are each as defined herein. In certain embodiments, $R^{7b}$ is —OC(=NR$^a$)NR$^b$R$^c$, wherein $R^a$, $R^b$, and $R^c$ are each as defined herein. In certain embodiments, $R^{7b}$ is —OS(O)$R^a$, wherein $R^a$ is as defined herein. In certain embodiments, $R^{7b}$ is —OS(O)$_2$$R^a$, wherein $R^a$ is as defined herein. In certain embodiments, $R^{7b}$ is —OS(O)NR$^b$R$^c$, wherein $R^b$ and $R^c$ are each as defined herein. In certain embodiments, $R^{7b}$ is —OS(O)$_2$NR$^b$R$^c$, wherein $R^b$ and $R^c$ are each as defined herein. In certain embodiments, $R^{7b}$ is —NR$^b$R$^c$, wherein $R^b$ and $R^c$ are each as defined herein. In certain embodiments, $R^{7b}$ is amino (—NH$_2$). In certain embodiments, $R^{7b}$ is —NR$^a$C(O)$R^d$, wherein $R^a$ and $R^d$ are each as defined herein. In certain embodiments, $R^{7b}$ is —NR$^a$C(O)O$R^d$, wherein $R^a$ and $R^d$ are each as defined herein. In certain embodiments, $R^{7b}$ is —NR$^a$C(O)NR$^b$R$^c$, wherein $R^a$, $R^b$, and $R^c$ are each as defined herein. In certain embodiments, $R^{7b}$ is —NR$^a$C(=NR$^d$)NR$^b$R$^c$, wherein $R^a$, $R^b$, $R^c$, and $R^d$ are each as defined herein. In certain embodiments, $R^{7b}$ is —NR$^a$S(O)$R^d$, wherein $R^a$ and $R^d$ are each as defined herein. In certain embodiments, $R^{7b}$ is —NR$^d$S(O)$_2$$R^d$, wherein $R^a$ and $R^d$ are each as defined herein. In certain embodiments, $R^{7b}$ is —NR$^d$S(O)NR$^b$R$^c$, wherein $R^a$, $R^b$, and $R^c$ are each as defined herein. In certain embodiments, $R^{7b}$ is —NR$^a$S(O)$_2$NR$^b$R$^c$, wherein $R^a$, $R^b$, and $R^c$ are each as defined herein. In certain embodiments, $R^{7b}$ is —SR$^a$, wherein $R^a$ is as defined herein. In certain embodiments, $R^{7b}$ is —S(O)$R^a$, wherein $R^a$ is as defined herein. In certain embodiments, $R^{7b}$ is —S(O)$_2$$R^a$, wherein $R^a$ is as defined herein. In certain embodiments, $R^{7b}$ is —S(O)NR$^b$R$^c$, wherein $R^b$ and $R^c$ are each as defined herein. In certain embodiments, $R^{7b}$ is —S(O)$_2$NR$^b$R$^c$; wherein $R^b$ and $R^c$ are each as defined herein.

In certain embodiments, $R^{7b}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$. In certain embodiments, $R^{7b}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7c}$ is hydrogen. In certain embodiments, $R^{7c}$ is cyano. In certain embodiments, $R^{7c}$ is halo. In certain embodiments, $R^{7c}$ is fluoro, chloro, bromo, or iodo. In certain embodiments, $R^{7c}$ is nitro. In certain embodiments, $R^{7c}$ is $C_{1-6}$ alkyl, optionally substituted with one, two, three, or four substituents $Q^a$ as described herein. In certain embodiments, $R^{7c}$ is $C_{2-6}$ alkenyl, optionally substituted with one, two, three, or four substituents $Q^a$ as described herein. In certain embodiments, $R^{7c}$ is $C_{2-6}$ alkynyl, optionally substituted with one, two, three, or four substituents $Q^a$ as described herein. In certain embodiments, $R^{7c}$ is $C_{3-10}$ cycloalkyl, optionally substituted with one, two, three, or four substituents $Q^a$ as described herein. In certain embodiments, $R^{7c}$ is $C_{3-7}$ cycloalkyl, optionally substituted with one, two, three, or four substituents $Q^a$ as described herein. In certain embodiments, $R^{7c}$ is $C_{6-14}$ aryl, optionally substituted with one, two, three, or four substituents $Q^a$ as described herein. In certain embodiments, $R^{7c}$ is $C_{7-15}$ aralkyl, optionally substituted with one, two, three, or four substituents $Q^a$ as described herein. In certain embodiments, $R^{7c}$ is heteroaryl, optionally substituted with one, two, three, or four substituents $Q^a$ as described herein. In certain embodiments, $R^{7c}$ is heterocyclyl, optionally substituted with one, two, three, or four substituents $Q^a$ as described herein.

In certain embodiments, $R^{7c}$ is —C(O)$R^a$, wherein $R^a$ is as defined herein. In certain embodiments, $R^{7c}$ is —C(O)O$R^a$, wherein $R^a$ is as defined herein. In certain embodiments, $R^{7c}$ is —C(O)N$R^b R^c$, wherein $R^b$ and $R^c$ are each as defined herein. In certain embodiments, $R^{7c}$ is —C(N$R^a$)N$R^b R^c$, wherein $R^a$, $R^b$, and $R^c$ are each as defined herein. In certain embodiments, $R^{7c}$ is —O$R^d$, wherein $R^a$ is as defined herein. In certain embodiments, $R^a$ is —O—$C_{1-6}$ alkyl, wherein the alkyl is optionally substituted with one, two, three, or four substituents $Q^a$ as described herein. In certain embodiments, $R^a$ is methoxy, ethoxy, propoxy, isopropoxy, or 3-dimethylaminopropoxy. In certain embodiments, $R^{7c}$ is —OC(O)$R^a$, wherein $R^a$ is as defined herein. In certain embodiments, $R^{7c}$ is —OC(O)O$R^a$, wherein $R^a$ is as defined herein. In certain embodiments, $R^{7c}$ is —OC(O)N$R^b R^c$, wherein $R^b$ and $R^c$ are each as defined herein. In certain embodiments, $R^{7c}$ is —OC(=N$R^a$)N$R^b R^c$, wherein $R^a$, $R^b$, and $R^c$ are each as defined herein. In certain embodiments, $R^{7c}$ is —OS(O)$R^a$, wherein $R^a$ is as defined herein. In certain embodiments, $R^{7c}$ is —OS(O)$_2 R^a$, wherein $R^a$ is as defined herein. In certain embodiments, $R^{7c}$ is —OS(O)N$R^b R^c$, wherein $R^b$ and $R^c$ are each as defined herein. In certain embodiments, $R^{7c}$ is —OS(O)$_2$N$R^b R^c$, wherein $R^b$ and $R^c$ are each as defined herein. In certain embodiments, $R^{7c}$ is —N$R^b R^c$, wherein $R^b$ and $R^c$ are each as defined herein. In certain embodiments, $R^{7c}$ is amino (—NH$_2$). In certain embodiments, $R^{7c}$ is —N$R^a$C(O)$R^d$, wherein $R^a$ and $R^d$ are each as defined herein. In certain embodiments, $R^{7c}$ is —N$R^a$C(O)O$R^d$, wherein $R^a$ and $R^d$ are each as defined herein. In certain embodiments, $R^{7c}$ is —N$R^a$C(O)N$R^b R^c$, wherein $R^a$, $R^b$, and $R^c$ are each as defined herein. In certain embodiments, $R^{7c}$ is —N$R^a$C(=N$R^d$)N$R^b R^c$, wherein $R^a$, $R^b$, $R^c$, and $R^d$ are each as defined herein. In certain embodiments, $R^{7c}$ is —N$R^a$S(O)$R^d$, wherein $R^a$ and $R^d$ are each as defined herein. In certain embodiments, $R^{7c}$ is —N$R^a$S(O)$_2 R^d$, wherein $R^a$ and $R^d$ are each as defined herein. In certain embodiments, $R^{7c}$ is —N$R^a$S(O)N$R^b R^c$, wherein $R^a$, $R^b$, and $R^c$ are each as defined herein. In certain embodiments, $R^{7c}$ is —N$R^a$S(O)$_2$N$R^b R^c$, wherein $R^a$, $R^b$, and $R^c$ are each as defined herein. In certain embodiments, $R^{7c}$ is —S$R^a$, wherein $R^a$ is as defined herein. In certain embodiments, $R^{7c}$ is —S(O)$R^a$, wherein $R^a$ is as defined herein. In certain embodiments, $R^{7c}$ is —S(O)$_2 R^a$, wherein $R^a$ is as defined herein. In certain embodiments, $R^{7c}$ is —S(O)N$R^b R^c$, wherein $R^b$ and $R^c$ are each as defined herein. In certain embodiments, $R^{7c}$ is —S(O)$_2$N$R^b R^c$; wherein $R^b$ and $R^c$ are each as defined herein.

In certain embodiments, $R^{7c}$ is phenyl, imidazolyl, pyrozolyl, pyridinyl, pyrimidinyl, pyrrolidinyl, piperidinyl, or piperazinyl, each optionally substituted with one, two, three, or four substituents $Q^a$. In certain embodiments, $R^{7c}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, $R^{7d}$ is hydrogen. In certain embodiments, $R^{7d}$ is cyano. In certain embodiments, $R^{7d}$ is halo. In certain embodiments, $R^{7d}$ is fluoro, chloro, bromo, or iodo. In certain embodiments, $R^{7d}$ is nitro. In certain embodiments, $R^{7d}$ is $C_{1-6}$ alkyl, optionally substituted with one, two, three, or four substituents $Q^a$ as described herein. In certain embodiments, $R^{7d}$ is $C_{2-6}$ alkenyl, optionally substituted with one, two, three, or four substituents $Q^a$ as described herein. In certain embodiments, $R^{7d}$ is $C_{2-6}$ alkynyl, optionally substituted with one, two, three, or four substituents $Q^a$ as described herein. In certain embodiments, $R^{7d}$ is $C_{3-10}$ cycloalkyl, optionally substituted with one, two, three, or four substituents $Q^a$ as described herein. In certain embodiments, $R^{7d}$ is $C_{3-7}$ cycloalkyl, optionally substituted with one, two, three, or four substituents $Q^a$ as described herein. In certain embodiments, $R^{7d}$ is $C_{6-14}$ aryl, optionally substituted with one, two, three, or four substituents $Q^a$ as described herein. In certain embodiments, $R^{7d}$ is $C_{7-15}$ aralkyl, optionally substituted with one, two, three, or four substituents $Q^a$ as described herein. In certain embodiments, $R^{7d}$ is heteroaryl, optionally substituted with one, two, three, or four substituents $Q^a$ as described herein. In certain embodiments, $R^{7d}$ is heterocyclyl, optionally substituted with one, two, three, or four substituents $Q^a$ as described herein.

In certain embodiments, $R^{7d}$ is —C(O)$R^a$, wherein $R^a$ is as defined herein. In certain embodiments, $R^{7d}$ is —C(O)O$R^a$, wherein $R^a$ is as defined herein. In certain embodiments, $R^{7d}$ is —C(O)N$R^b R^c$, wherein $R^b$ and $R^c$ are each as defined herein. In certain embodiments, $R^{7d}$ is —C(N$R^a$)N$R^b R^c$, wherein $R^a$, $R^b$, and $R^c$ are each as defined herein. In certain embodiments, $R^{7d}$ is —O$R^a$, wherein $R^a$ is as defined herein. In certain embodiments, $R^a$ is —O—$C_{1-6}$ alkyl, wherein the alkyl is optionally substituted with one, two, three, or four substituents $Q^a$ as described herein. In certain embodiments, $R^a$ is methoxy, ethoxy, propoxy, isopropoxy, or 3-dimethylaminopropoxy. In certain embodiments, $R^{7d}$ is —OC(O)$R^a$, wherein $R^a$ is as defined herein. In certain embodiments, $R^{7d}$ is —OC(O)O$R^a$, wherein $R^a$ is as defined herein. In certain embodiments, $R^{7d}$ is —OC(O)N$R^b R^c$, wherein $R^b$ and $R^c$ are each as defined herein. In certain embodiments, $R^{7d}$ is —OC(=N$R^a$)N$R^b R^c$, wherein $R^a$, $R^b$, and $R^c$ are each as defined herein. In certain embodiments, $R^{7d}$ is —OS(O)$R^a$, wherein $R^a$ is as defined herein. In certain embodiments, $R^{7d}$ is —OS(O)$_2 R^a$, wherein $R^a$ is as defined herein. In certain embodiments, $R^{7d}$ is —OS(O)N$R^b R^c$, wherein $R^b$ and $R^c$ are each as defined herein. In certain embodiments, $R^{7d}$ is —OS(O)$_2$N$R^b R^c$, wherein $R^b$ and $R^c$ are each as defined herein. In certain embodiments, $R^{7d}$ is —N$R^b R^c$, wherein $R^b$ and $R^c$ are each as defined herein. In certain embodiments, $R^{7d}$ is amino (—NH$_2$). In certain embodiments, $R^{7d}$ is —N$R^a$C(O)$R^d$, wherein $R^a$ and $R^d$ are each as defined herein. In certain embodiments, $R^{7d}$ is —N$R^a$C(O)O$R^d$, wherein $R^a$ and $R^d$ are each as defined herein. In certain embodiments, $R^{7d}$ is —N$R^a$C(O)N$R^b R^c$, wherein $R^a$, $R^b$, and $R^c$ are each as defined herein. In certain embodiments, $R^{7d}$ is —N$R^a$C(=N$R^d$)N$R^b R^c$, wherein $R^a$, $R^b$, $R^c$, and $R^d$ are each as defined herein. In certain embodiments, $R^{7d}$ is —N$R^a$S(O)$R^d$, wherein $R^a$ and $R^d$ are each as defined herein. In certain embodiments, $R^{7d}$ is —N$R^a$S(O)$_2 R^d$, wherein $R^a$ and $R^d$ are each as defined herein. In certain embodiments, $R^{7d}$ is —N$R^a$S(O)N$R^b R^c$, wherein $R^a$, $R^b$, and $R^c$ are each as defined herein. In certain embodiments, $R^{7d}$ is —N$R^a$S(O)$_2$ NR$^b$R$^c$, wherein R$^a$, R$^b$, and R$^c$ are each as defined herein. In certain embodiments, R$^{7d}$ is —SR$^a$, wherein R$^a$ is as defined herein. In certain embodiments, R$^{7d}$ is —S(O)R$^a$, wherein R$^a$ is as defined herein. In certain embodiments, R$^{7d}$ is —S(O)$_2$R$^a$, wherein R$^a$ is as defined herein. In certain embodiments, R$^{7d}$ is —S(O)NR$^b$R$^c$, wherein R$^b$ and R$^c$ are each as defined herein. In certain embodiments, R$^{7d}$ is —S(O)$_2$NR$^b$R$^c$; wherein R$^b$ and R$^c$ are each as defined herein.

In certain embodiments, R$^{7d}$ is phenyl, imidazolyl, pyrozolyl, pyridinyl, pyrimidinyl, pyrrolidinyl, piperidinyl, or piperazinyl, each optionally substituted with one, two, three, or four substituents Q$^a$. In certain embodiments, R$^{7d}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, R$^{7e}$ is hydrogen. In certain embodiments, R$^{7e}$ is cyano. In certain embodiments, R$^{7e}$ is halo. In certain embodiments, R$^{7e}$ is fluoro, chloro, bromo, or iodo. In certain embodiments, R$^{7e}$ is nitro. In certain embodiments, R$^{7e}$ is C$_{1-6}$ alkyl, optionally substituted with one, two, three, or four substituents Q$^a$ as described herein. In certain embodiments, R$^{7c}$ is C$_{2-6}$ alkenyl, optionally substituted with one, two, three, or four substituents Q$^a$ as described herein. In certain embodiments, R$^{7e}$ is C$_{2-6}$ alkynyl, optionally substituted with one, two, three, or four substituents Q$^a$ as described herein. In certain embodiments, R$^{7e}$ is C$_{3-10}$ cycloalkyl, optionally substituted with one, two, three, or four substituents Q$^a$ as described herein. In certain embodiments, R$^{7e}$ is C$_{3-7}$ cycloalkyl, optionally substituted with one, two, three, or four substituents Q$^a$ as described herein. In certain embodiments, R$^{7e}$ is C$_{6-14}$ aryl, optionally substituted with one, two, three, or four substituents Q$^a$ as described herein. In certain embodiments, R$^{7e}$ is C$_{7-15}$ aralkyl, optionally substituted with one, two, three, or four substituents Q$^a$ as described herein. In certain embodiments, R$^{7c}$ is heteroaryl, optionally substituted with one, two, three, or four substituents Q$^a$ as described herein. In certain embodiments, R$^{7e}$ is heterocyclyl, optionally substituted with one, two, three, or four substituents Q$^a$ as described herein.

In certain embodiments, R$^{7e}$ is —C(O)R$^a$, wherein R$^a$ is as defined herein. In certain embodiments, R$^{7e}$ is —C(O)OR$^a$, wherein R$^a$ is as defined herein. In certain embodiments, R$^{7c}$ is —C(O)NR$^b$R$^c$, wherein R$^b$ and R$^c$ are each as defined herein. In certain embodiments, R$^{7e}$ is —C(NR$^a$)NR$^b$R$^c$, wherein R$^a$, R$^b$, and R$^c$ are each as defined herein. In certain embodiments, R$^{7e}$ is —OR$^a$, wherein R$^a$ is as defined herein. In certain embodiments, R$^a$ is —O—C$_{1-6}$ alkyl, wherein the alkyl is optionally substituted with one, two, three, or four substituents Q$^a$ as described herein. In certain embodiments, R$^a$ is methoxy, ethoxy, propoxy, isopropoxy, or 3-dimethylaminopropoxy. In certain embodiments, R$^{7c}$ is —OC(O)R$^a$, wherein R$^a$ is as defined herein. In certain embodiments, R$^{7c}$ is —OC(O)OR$^a$, wherein R$^a$ is as defined herein. In certain embodiments, R$^{7e}$ is —OC(O)NR$^b$R$^c$, wherein R$^b$ and R$^c$ are each as defined herein. In certain embodiments, R$^{7c}$ is —OC(=NR$^a$)NR$^b$R$^c$, wherein R$^a$, R$^b$, and R$^c$ are each as defined herein. In certain embodiments, R$^{7e}$ is —OS(O)R$^a$, wherein R$^a$ is as defined herein. In certain embodiments, R$^{7e}$ is —OS(O)$_2$R$^a$, wherein R$^a$ is as defined herein. In certain embodiments, R$^{7c}$ is —OS(O)NR$^b$R$^c$, wherein R$^b$ and R$^c$ are each as defined herein. In certain embodiments, R$^{7e}$ is —OS(O)$_2$NR$^b$R$^c$, wherein R$^b$ and R$^c$ are each as defined herein. In certain embodiments, R$^{7c}$ is —NR$^b$R$^c$, wherein R$^b$ and R$^c$ are each as defined herein. In certain embodiments, R$^{7e}$ is amino (—NH$_2$). In certain embodiments, R$^{7c}$ is —NR$^a$C(O)R$^d$, wherein R$^a$ and R$^d$ are each as defined herein. In certain embodiments, R$^{7c}$ is —NR$^a$C(O)OR$^d$, wherein R$^a$ and R$^d$ are each as defined herein. In certain embodiments, R$^{7c}$ is —NR$^a$C(O)NR$^b$R$^c$, wherein R$^a$, R$^b$, and R$^c$ are each as defined herein. In certain embodiments, R$^{7c}$ is —NR$^a$C(=NR$^d$)NR$^b$R$^c$, wherein R$^a$, R$^b$, R$^c$, and R$^d$ are each as defined herein. In certain embodiments, R$^{7e}$ is —NR$^a$S(O)R$^d$, wherein R$^a$ and R$^d$ are each as defined herein. In certain embodiments, R$^{7e}$ is —NR$^a$S(O)$_2$R$^d$, wherein R$^a$ and R$^d$ are each as defined herein. In certain embodiments, R$^{7e}$ is —NR$^a$S(O)NR$^b$R$^c$, wherein R$^a$, R$^b$, and R$^c$ are each as defined herein. In certain embodiments, R$^{7e}$ is —NR$^a$S(O)$_2$NR$^b$R$^c$, wherein R$^a$, R$^b$, and R$^c$ are each as defined herein. In certain embodiments, R$^{7e}$ is —SR$^a$, wherein R$^a$ is as defined herein. In certain embodiments, R$^{7e}$ is —S(O)R$^a$, wherein R$^a$ is as defined herein. In certain embodiments, R$^{7e}$ is —S(O)$_2$R$^a$, wherein R$^a$ is as defined herein. In certain embodiments, R$^{7e}$ is —S(O)NR$^b$R$^c$, wherein R$^b$ and R$^c$ are each as defined herein. In certain embodiments, R$^{7e}$ is —S(O)$_2$NR$^b$R$^c$; wherein R$^b$ and R$^c$ are each as defined herein.

In certain embodiments, R$^{7e}$ is phenyl, imidazolyl, pyrozolyl, pyridinyl, pyrimidinyl, pyrrolidinyl, piperidinyl, or piperazinyl, each optionally substituted with one, two, three, or four substituents Q$^a$. In certain embodiments, R$^{7e}$ is phenyl, 2-fluorophenyl, 2-chlorophenyl, 2-bromophenyl, 2-methylphenyl, 2-(3-dimethylaminopropyl)phenyl, 2-methoxyphenyl, 3-fluorophenyl, 3-chlorophenyl, 3-methylphenyl, 3-methoxyphenyl, 4-florophenyl, 4-chlorophenyl, 4-bromophenyl, 4-methoxyphenyl, 2,4-difluorophenyl, 2,6-difluorophenyl, 4-fluoro-3-methoxyphenyl, 3-methoxyphenyl, 4-methoxyphenyl, 3-morpholin-4-ylmethylphenyl, imidazol-1-yl, pyrozol-4-yl, 1-methyl-pyrozol-4-yl, 2-methylpyrozol-3-yl, pyridin-2-yl, pyridin-3-yl, pyridin-4-yl, 2-fluoropyridin-3-yl, 2-methylpyridin-4-yl, 2-(4-methylpiperazin-1-yl)pyridin-4-yl, 2-methoxypyridin-4-yl, pyrimidin-5-yl, pyrrolidin-3-yl, 1-methylpyrrolidin-3-yl, piperidin-4-yl, 1-methylpiperidin-4-yl, 1-ethylpiperidin-4-yl, 1-isopropylpiperidin-4-yl, 1-acetylpiperidin-4-yl, 1-methylsulfonylpiperidin-4-yl, or 4-methylpiperazin-1-yl.

In certain embodiments, R$^{7a}$ and R$^{7b}$ together with the carbon atoms to which they are attached form C$_{3-10}$ cycloalkenyl, C$_{6-14}$ aryl, heteroaryl, or heterocyclyl, each optionally substituted with one, two, three, or four substituents Q$^a$. In certain embodiments, R$^{7a}$ and R$^{7b}$ together with the carbon atoms to which they are attached form C$_{3-10}$ cycloalkenyl, optionally substituted with one, two, three, or four substituents Q$^a$. In certain embodiments, R$^{7a}$ and R$^{7b}$ together with the carbon atoms to which they are attached form cyclohexenyl, optionally substituted with one, two, three, or four substituents Q$^a$. In certain embodiments, R$^{7a}$ and R$^{7b}$ together with the carbon atoms to which they are attached form C$_{6-14}$ aryl, optionally substituted with one, two, three, or four substituents Q$^a$. In certain embodiments, $R^{7a}$ and $R^{7b}$ together with the carbon atoms to which they are attached form phenyl, optionally substituted with one, two, three, or four substituents $Q^a$. In certain embodiments, $R^{7a}$ and $R^{7b}$ together with the carbon atoms to which they are attached form heteroaryl, optionally substituted with one, two, three, or four substituents $Q^a$. In certain embodiments, $R^{7a}$ and $R^{7b}$ together with the carbon atoms to which they are attached form monocyclic heteroaryl, optionally substituted with one, two, three, or four substituents $Q^a$. In certain embodiments, $R^{7a}$ and $R^{7b}$ together with the carbon atoms to which they are attached form 5- or 6-membered heteroaryl, optionally substituted with one, two, three, or four substituents Q. In certain embodiments, $R^{7a}$ and $R^{7b}$ together with the carbon atoms to which they are attached form bicyclic heteroaryl, optionally substituted with one, two, three, or four substituents $Q^a$. In certain embodiments, $R^{7a}$ and $R^{7b}$ together with the carbon atoms to which they are attached form heterocyclyl, optionally substituted with one, two, three, or four substituents $Q^a$. In certain embodiments, $R^{7a}$ and $R^{7b}$ together with the carbon atoms to which they are attached form monocyclic heterocyclyl, optionally substituted with one, two, three, or four substituents $Q^a$. In certain embodiments, $R^{7a}$ and $R^{7b}$ together with the carbon atoms to which they are attached form 5- or 6-membered heterocyclyl, optionally substituted with one, two, three, or four substituents $Q^a$. In certain embodiments, $R^{7a}$ and $R^{7b}$ together with the carbon atoms to which they are attached form bicyclic heterocyclyl, optionally substituted with one, two, three, or four substituents $Q^a$.

In certain embodiments, $R^{7b}$ and $R^{7c}$ together with the carbon atoms to which they are attached form $C_{3-10}$ cycloalkenyl, $C_{6-14}$ aryl, heteroaryl, or heterocyclyl, each optionally substituted with one, two, three, or four substituents $Q^a$. In certain embodiments, $R^b$ and $R^{7c}$ together with the carbon atoms to which they are attached form $C_{3-10}$ cycloalkenyl, optionally substituted with one, two, three, or four substituents $Q^a$. In certain embodiments, $R^{7b}$ and $R^{7c}$ together with the carbon atoms to which they are attached form cyclohexenyl, optionally substituted with one, two, three, or four substituents $Q^a$. In certain embodiments, $R^{7b}$ and $R^{7c}$ together with the carbon atoms to which they are attached form $C_{6-14}$ aryl, optionally substituted with one, two, three, or four substituents $Q^a$. In certain embodiments, $R^{7b}$ and $R^{7c}$ together with the carbon atoms to which they are attached form phenyl, optionally substituted with one, two, three, or four substituents $Q^a$. In certain embodiments, $R^{7b}$ and $R^{7c}$ together with the carbon atoms to which they are attached form heteroaryl, optionally substituted with one, two, three, or four substituents $Q^a$. In certain embodiments, $R^{7b}$ and $R^{7c}$ together with the carbon atoms to which they are attached form monocyclic heteroaryl, optionally substituted with one, two, three, or four substituents $Q^a$. In certain embodiments, $R^{7b}$ and $R^{7c}$ together with the carbon atoms to which they are attached form 5- or 6-membered heteroaryl, optionally substituted with one, two, three, or four substituents Q. In certain embodiments, $R^{7b}$ and $R^{7c}$ together with the carbon atoms to which they are attached form bicyclic heteroaryl, optionally substituted with one, two, three, or four substituents $Q^a$. In certain embodiments, $R^{7b}$ and $R^{7c}$ together with the carbon atoms to which they are attached form heterocyclyl, optionally substituted with one, two, three, or four substituents $Q^a$. In certain embodiments, $R^{7b}$ and $R^{7c}$ together with the carbon atoms to which they are attached form monocyclic heterocyclyl, optionally substituted with one, two, three, or four substituents $Q^a$. In certain embodiments, $R^{7b}$ and $R^{7c}$ together with the carbon atoms to which they are attached form 5- or 6-membered heterocyclyl, optionally substituted with one, two, three, or four substituents $Q^a$. In certain embodiments, $R^{7b}$ and $R^{7c}$ together with the carbon atoms to which they are attached form bicyclic heterocyclyl, optionally substituted with one, two, three, or four substituents $Q^a$.

In certain embodiments, $R^{7c}$ and $R^{7d}$ together with the carbon atoms to which they are attached form $C_{3-10}$ cycloalkenyl, $C_{6-14}$ aryl, heteroaryl, or heterocyclyl, each optionally substituted with one, two, three, or four substituents $Q^a$. In certain embodiments, $R^{7c}$ and $R^{7d}$ together with the carbon atoms to which they are attached form $C_{3-10}$ cycloalkenyl, optionally substituted with one, two, three, or four substituents $Q^a$. In certain embodiments, $R^{7c}$ and $R^{7d}$ together with the carbon atoms to which they are attached form cyclohexenyl, optionally substituted with one, two, three, or four substituents $Q^a$. In certain embodiments, $R^{7c}$ and $R^{7d}$ together with the carbon atoms to which they are attached form $C_{6-14}$ aryl, optionally substituted with one, two, three, or four substituents $Q^a$. In certain embodiments, $R^{7c}$ and $R^{7d}$ together with the carbon atoms to which they are attached form phenyl, optionally substituted with one, two, three, or four substituents $Q^a$. In certain embodiments, $R^{7c}$ and $R^{7d}$ together with the carbon atoms to which they are attached form heteroaryl, optionally substituted with one, two, three, or four substituents $Q^a$. In certain embodiments, $R^{7c}$ and $R^{7d}$ together with the carbon atoms to which they are attached form monocyclic heteroaryl, optionally substituted with one, two, three, or four substituents $Q^a$. In certain embodiments, $R^{7c}$ and $R^{7d}$ together with the carbon atoms to which they are attached form 5- or 6-membered heteroaryl, optionally substituted with one, two, three, or four substituents $Q^a$. In certain embodiments, $R^{7c}$ and $R^{7d}$ together with the carbon atoms to which they are attached form bicyclic heteroaryl, optionally substituted with one, two, three, or four substituents $Q^a$. In certain embodiments, $R^{7c}$ and $R^{7d}$ together with the carbon atoms to which they are attached form heterocyclyl, optionally substituted with one, two, three, or four substituents $Q^a$. In certain embodiments, $R^{7c}$ and $R^{7d}$ together with the carbon atoms to which they are attached form monocyclic heterocyclyl, optionally substituted with one, two, three, or four substituents $Q^a$. In certain embodiments, $R^{7c}$ and $R^{7d}$ together with the carbon atoms to which they are attached form 5- or 6-membered heterocyclyl, optionally substituted with one, two, three, or four substituents $Q^a$. In certain embodiments, $R^{7c}$ and $R^{7d}$ together with the carbon atoms to which they are attached form bicyclic heterocyclyl, optionally substituted with one, two, three, or four substituents $Q^a$.

In certain embodiments, $R^{7d}$ and $R^{7e}$ together with the carbon atoms to which they are attached form $C_{3-10}$ cycloalkenyl, $C_{6-14}$ aryl, heteroaryl, or heterocyclyl, each optionally substituted with one, two, three, or four substituents $Q^a$. In certain embodiments, $R^{7d}$ and $R^{7e}$ together with the carbon atoms to which they are attached form $C_{3-10}$ cycloalkenyl, optionally substituted with one, two, three, or four substituents $Q^a$. In certain embodiments, $R^{7d}$ and $R^{7e}$ together with the carbon atoms to which they are attached form cyclohexenyl, optionally substituted with one, two, three, or four substituents $Q^a$. In certain embodiments, $R^{7d}$ and $R^{7e}$ together with the carbon atoms to which they are attached form $C_{6-14}$ aryl, optionally substituted with one, two, three, or four substituents $Q^a$. In certain embodiments, $R^{7d}$ and $R^{7e}$ together with the carbon atoms to which they are attached form phenyl, optionally substituted with one, two, three, or four substituents $Q^a$. In certain embodiments, $R^{7d}$ and $R^{7e}$ together with the carbon atoms to which they are attached form heteroaryl, optionally substituted with one, two, three, or four substituents $Q^a$. In certain embodiments, $R^{7d}$ and $R^{7e}$ together with the carbon atoms to which they are attached form monocyclic heteroaryl, optionally substituted with one, two, three, or four substituents $Q^a$. In certain embodiments, $R^{7d}$ and $R^{7e}$ together with the carbon atoms to which they are attached form 5- or 6-membered heteroaryl, optionally substituted with one, two, three, or four substituents $Q^a$. In certain embodiments, $R^{7d}$ and $R^{7e}$ together with the carbon atoms to which they are attached form bicyclic heteroaryl, optionally substituted with one, two, three, or four substituents $Q^a$. In certain embodiments, $R^{7d}$ and $R^{7e}$ together with the carbon atoms to which they are attached form heterocyclyl, optionally substituted with one, two, three, or four substituents $Q^a$. In certain embodiments, $R^{7d}$ and $R^{7e}$ together with the carbon atoms to which they are attached form monocyclic heterocyclyl, optionally substituted with one, two, three, or four substituents $Q^a$. In certain embodiments, $R^{7d}$ and $R^{7e}$ together with the carbon atoms to which they are attached form 5- or 6-membered heterocyclyl, optionally substituted with one, two, three, or four substituents $Q^a$. In certain embodiments, $R^{7d}$ and $R^{7e}$ together with the carbon atoms to which they are attached form bicyclic heterocyclyl, optionally substituted with one, two, three, or four substituents $Q^a$.

In certain embodiments, m is 0. In certain embodiments, m is 1.

In certain embodiments, n is 0. In certain embodiments, n is 1. In certain embodiments, n is 2. In certain embodiments, n is 3. In certain embodiments, n is 4. In certain embodiments, n is 0, 1, or 2. In certain embodiments, n is 0, 1, 2, or 3. In certain embodiments, n is 1, 2, or 3. In certain embodiments, n is 1 or 2.

In certain embodiments, m is 0, and n is 0, 1, 2, or 3. In certain embodiments, m is 0, n is 0, 1, or 2. In certain embodiments, m is 0, and n is 0 or 1. In certain embodiments, m is 0, and n is 0. In certain embodiments, m is 0, and n is 1. In certain embodiments, m is 1, and n is 0, 1, 2, or 3. In certain embodiments, m is 1, and n is 0, 1, or 2. In certain embodiments, m is 1, and n is 0 or 1. In certain embodiments, m is 1, and n is 0. In certain embodiments, m is 1, and n is 1.

In specific embodiments, m is 0, n is 1, and $R^{5a}$ and $R^{5b}$ are each methyl.

In certain embodiments, X is N In certain embodiments, X is $CR^x$, wherein $R^x$ is as defined herein. In certain embodiments, X is CH.

In certain embodiments, Y is N In certain embodiments, Y is $CR^x$, wherein $R^x$ is as defined herein. In certain embodiments, Y is CH.

In certain embodiments, Z is N In certain embodiments, Z is $CR^x$, wherein $R^x$ is as defined herein. In certain embodiments, Z is CH.

In certain embodiments, X, Y, and Z are N. In certain embodiments, X and Y are N, and Z is CH. In certain embodiments, X and Z are N, and Y is CH. In certain embodiments, Y and Z are N, and X is CH.

In certain embodiments, the compound provided herein is not 4-(2-(difluoromethyl)-1H-benzo[d]imidazol-1-yl)-6-morpholino-N-(2-phenyl-2-(pyrrolidin-1-ypethyl)-1,3,5-triazin-2-amine. In certain embodiments, the compound provided herein is not 6-(2-(difluoromethyl)-1H-benzoldlimidazol-1-yl)-N-(1-(4-((R)-3-(methoxymethyl)morpholino)phenyl)ethyl)-2-morpholinopyrimidin-4-amine.

In certain embodiments, when X, Y, and Z are N, and $R^{5a}$ is hydrogen, $R^{5b}$ is not heterocyclyl. In certain embodiments, when X, Y, and Z are N, and $R^{5a}$ is hydrogen, $R^{5b}$ is not 5-membered heterocyclyl. In certain embodiments, when X, Y, and Z are N, and $R^{5a}$ is hydrogen, $R^{5b}$ is not pyrrolidinyl. In certain embodiments, when X, Y, and Z are N, and $R^{5a}$ is hydrogen, $R^{5b}$ is not pyrrolidin-1-yl.

In certain embodiments, when X and Z are N, Y is CH, and $R^{5a}$ is hydrogen, $R^{5b}$ is morpholino-substituted phenyl. In certain embodiments, when X and Z are N, Y is CH, and $R^{5a}$ is hydrogen, $R^{5b}$ is not 4-((R)-3-(methoxymethyl)morpholino)phenyl.

In one embodiment, provided herein is a compound selected from:

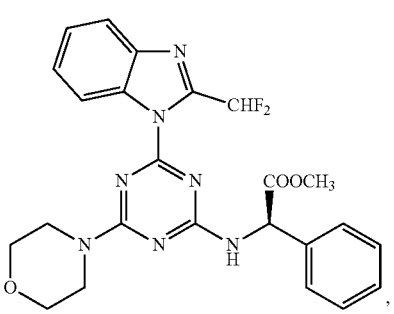

A11

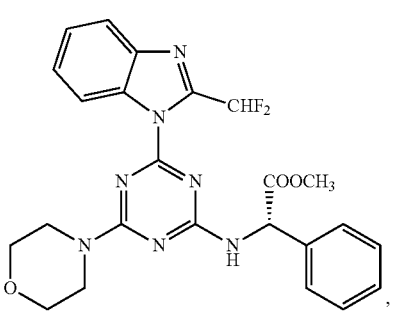

A12

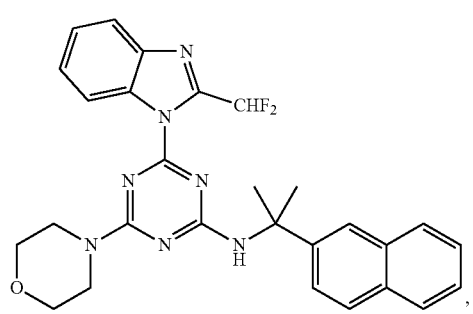

A13

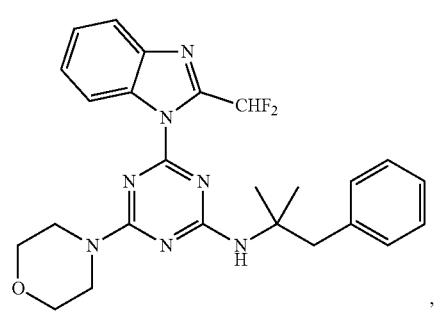

A14

-continued
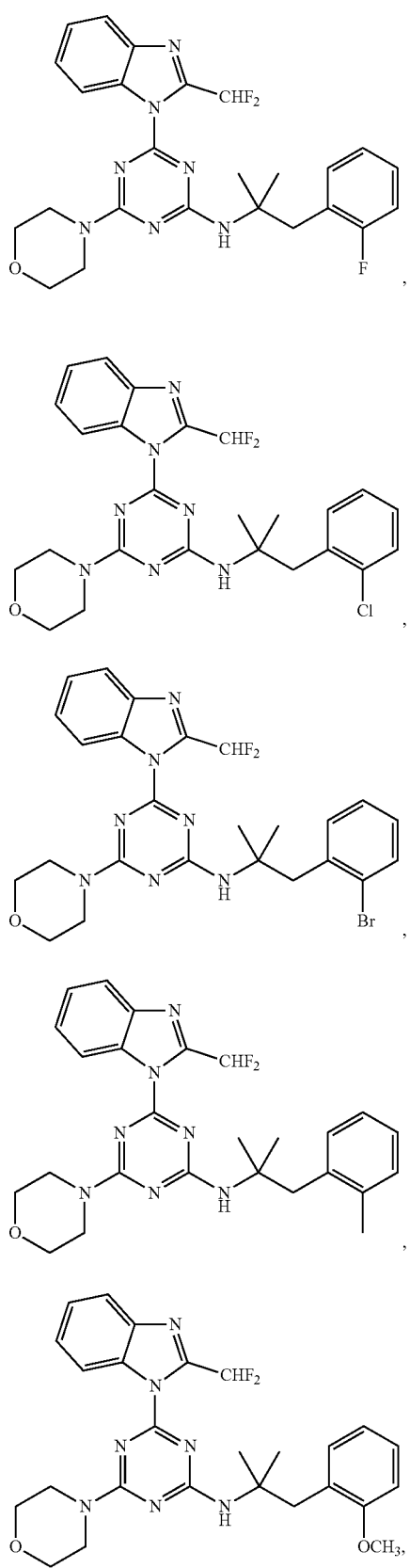
A15
A16
A17
A18
A19
-continued
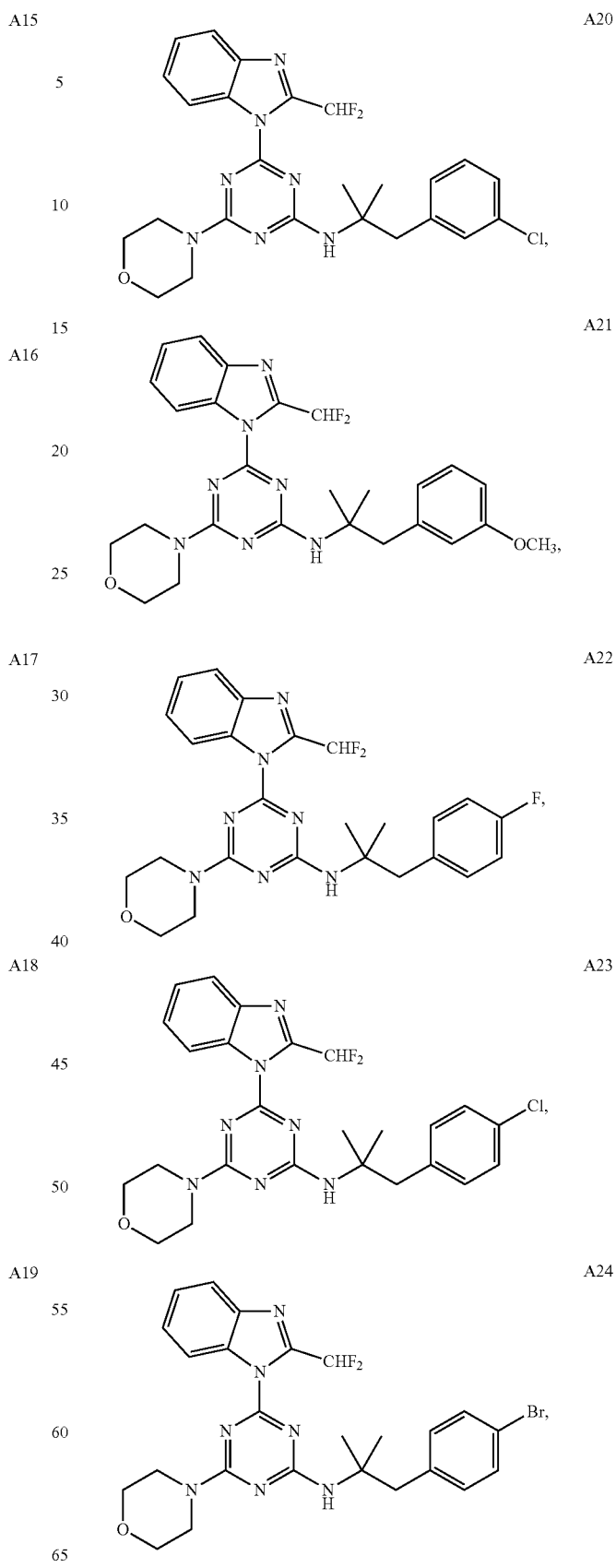
A20
A21
A22
A23
A24

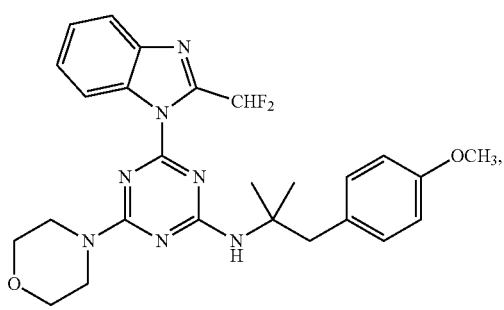
A25
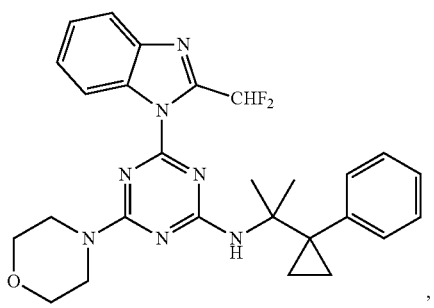
A30
A26
A31
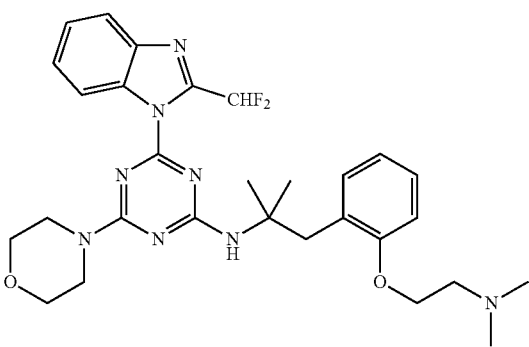
A27
A32
A28
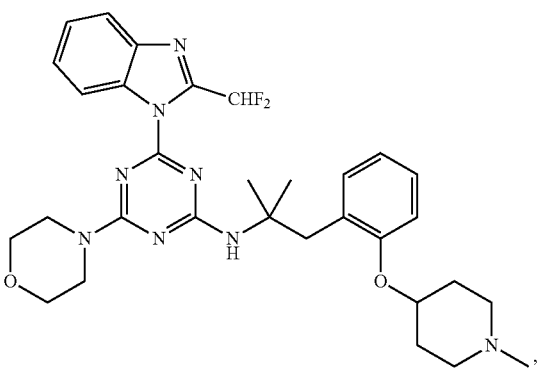
A29
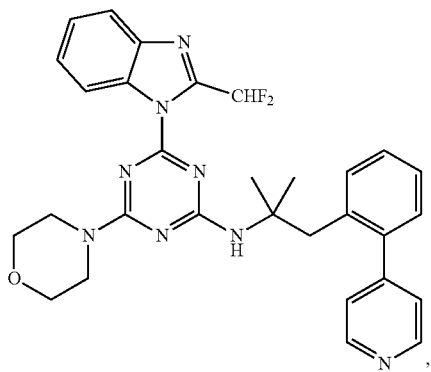
A33

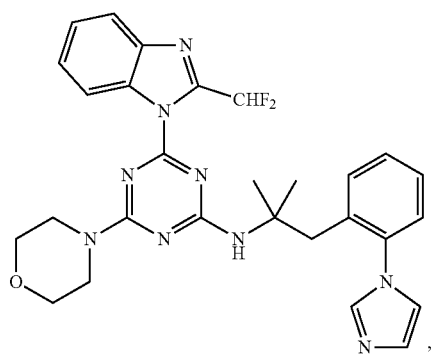
A34
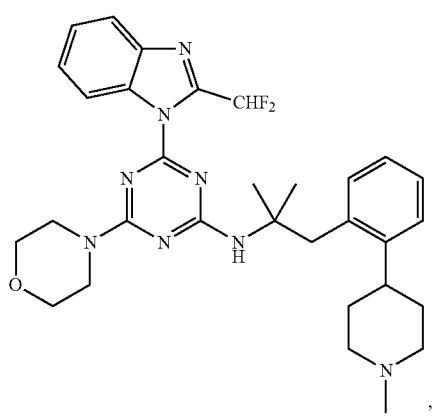
A35
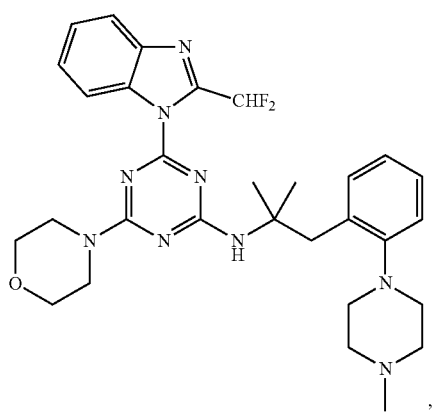
A36
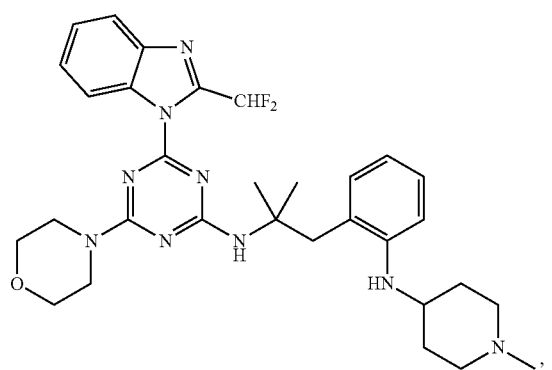
A37
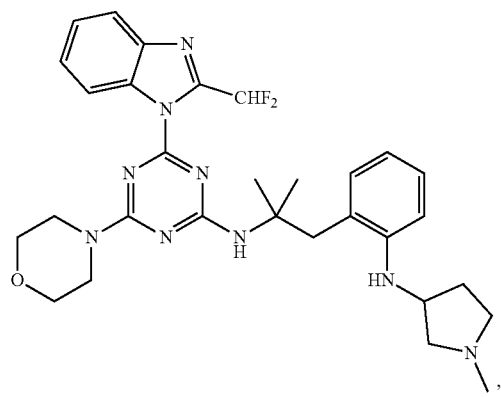
A38
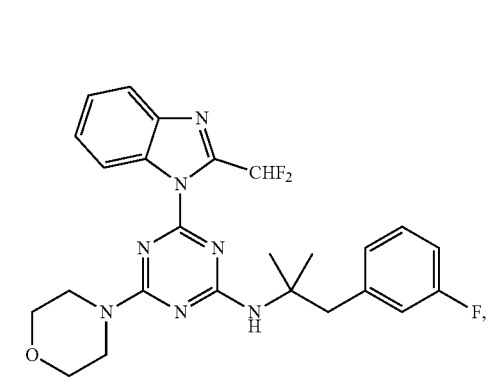
A39
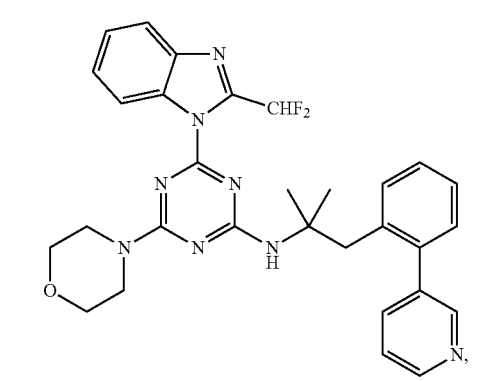
A40
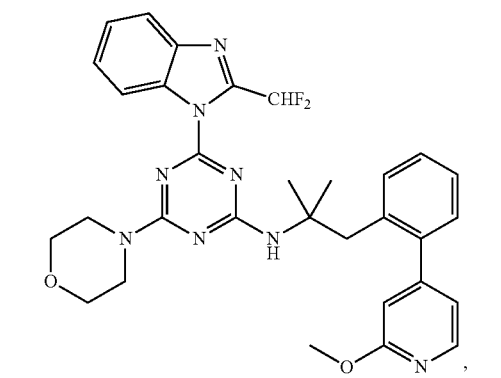
A41

A42 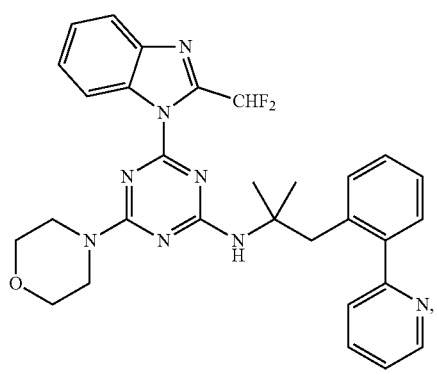
A43 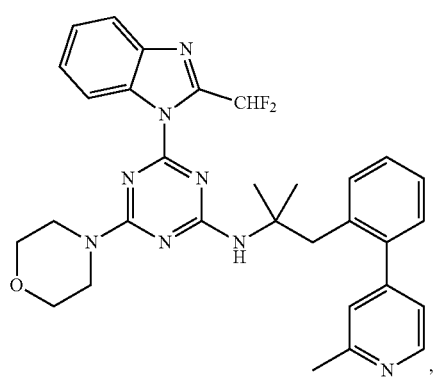
A44 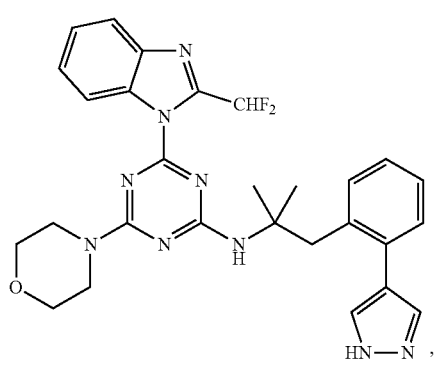
A45 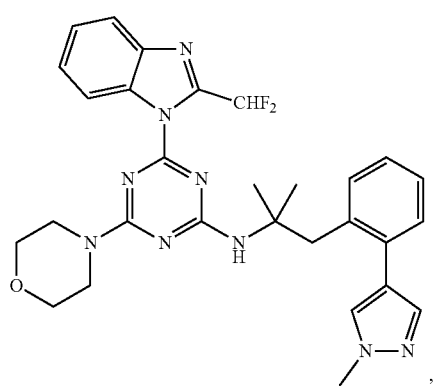
A46 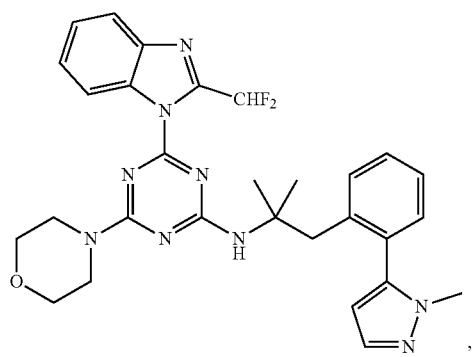
A47 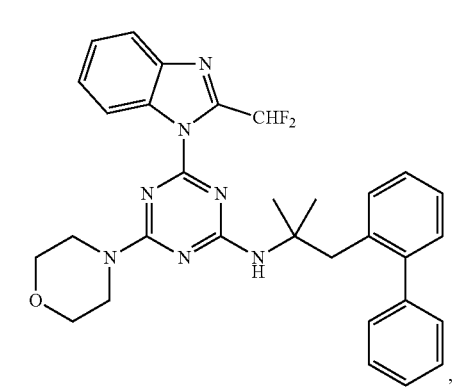
A49 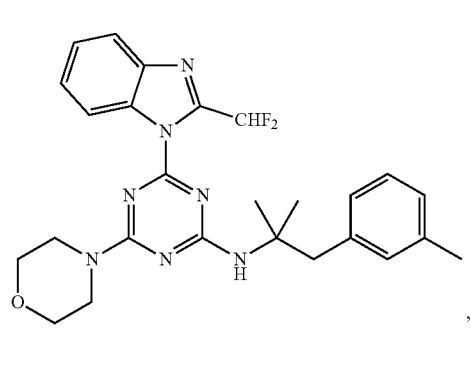
A50 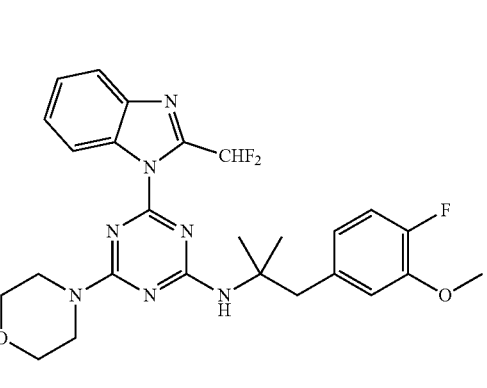

-continued
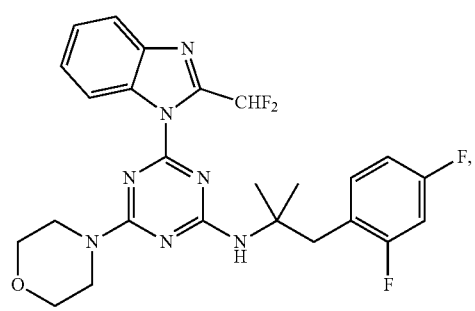
A51
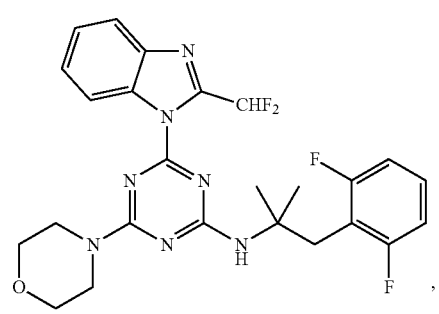
A52
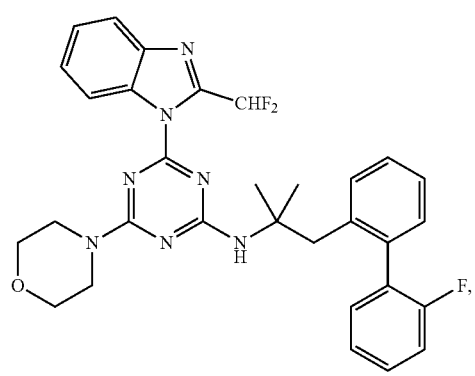
A59
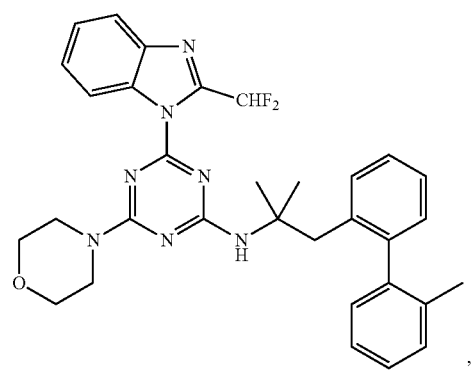
A60
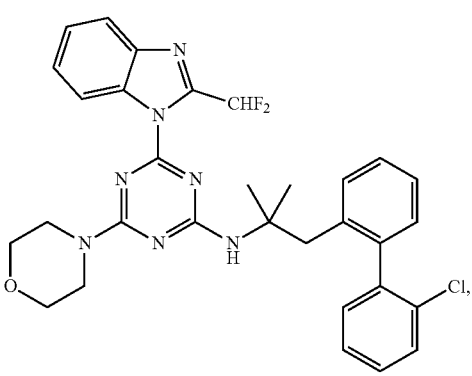
A61
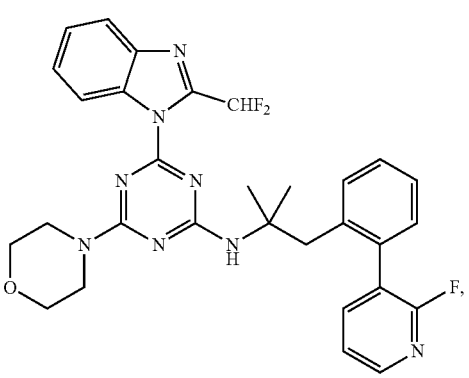
A62
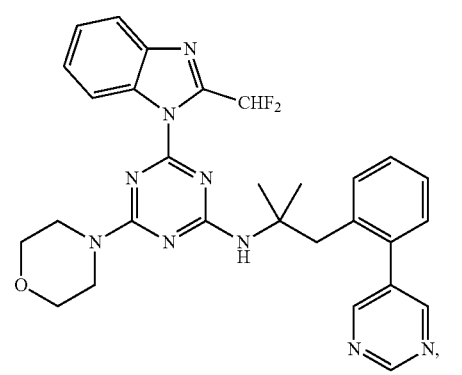
A63
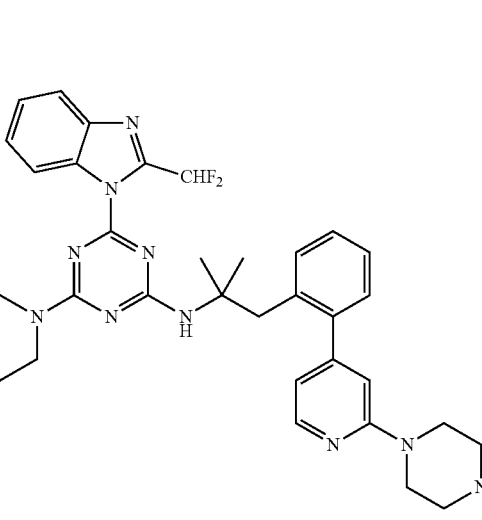
A64

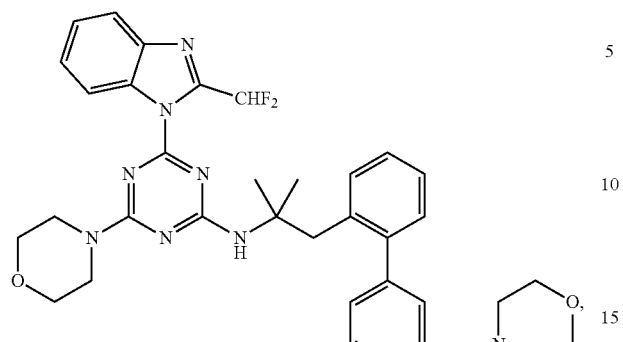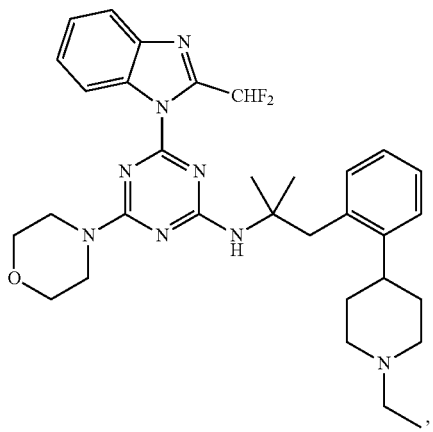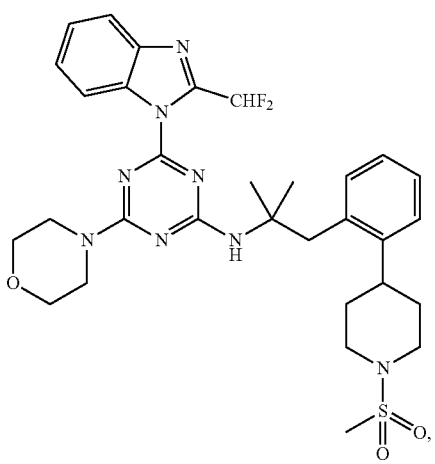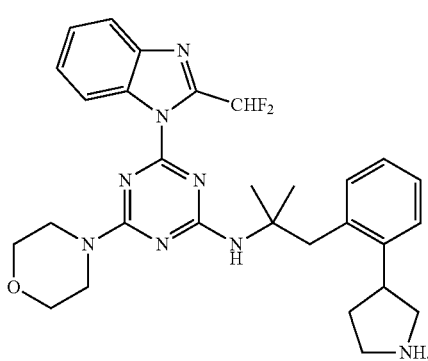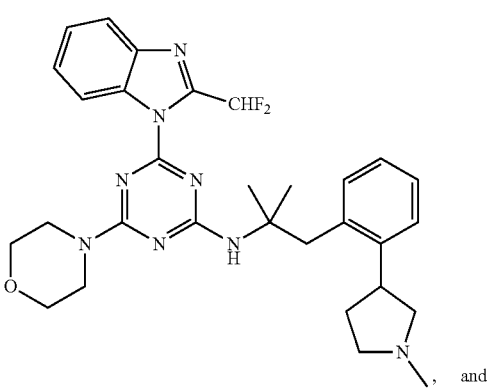

-continued

A76

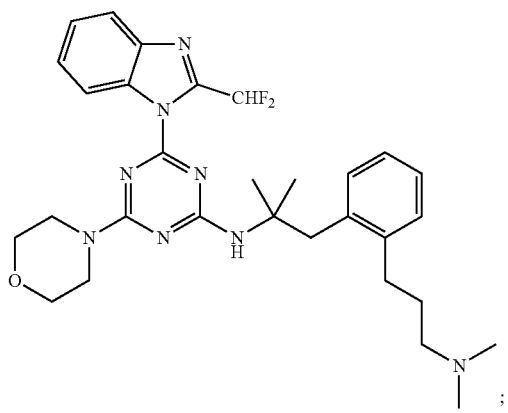

In one embodiment, the PI3K inhibitor is Compound A35, isotopic variants, pharmaceutically acceptable salts, solvates, hydrates, and prodrugs thereof. In one embodiment, the PI3K inhibitor is Compound A36, isotopic variants, pharmaceutically acceptable salts, solvates, hydrates, and prodrugs thereof. In one embodiment, the PI3K inhibitor is Compound A68, isotopic variants, pharmaceutically acceptable salts, solvates, hydrates, and prodrugs thereof. In one embodiment, the PI3K inhibitor is Compound A70, isotopic variants, pharmaceutically acceptable salts, solvates, hydrates, and prodrugs thereof. In one embodiment, the PI3K inhibitor is Compound A37, isotopic variants, pharmaceutically acceptable salts, solvates, hydrates, and prodrugs thereof. In one embodiment, the PI3K inhibitor is Compound A38, isotopic variants, pharmaceutically acceptable salts, solvates, hydrates, and prodrugs thereof. In one embodiment, the PI3K inhibitor is Compound A41, isotopic variants, pharmaceutically acceptable salts, solvates, hydrates, and prodrugs thereof. In one embodiment, the PI3K inhibitor is Compound A42, isotopic variants, pharmaceutically acceptable salts, solvates, hydrates, and prodrugs thereof. In one embodiment, the PI3K inhibitor is Compound A43, isotopic variants, pharmaceutically acceptable salts, solvates, hydrates, and prodrugs thereof. In one embodiment, the PI3K inhibitor is Compound A44, isotopic variants, pharmaceutically acceptable salts, solvates, hydrates, and prodrugs thereof. In one embodiment, the PI3K inhibitor is Compound A62, isotopic variants, pharmaceutically acceptable salts, solvates, hydrates, and prodrugs thereof. In one embodiment, the PI3K inhibitor is Compound A63, isotopic variants, pharmaceutically acceptable salts, solvates, hydrates, and prodrugs thereof. In one embodiment, the PI3K inhibitor is Compound A64, isotopic variants, pharmaceutically acceptable salts, solvates, hydrates, and prodrugs thereof. In one embodiment, the PI3K inhibitor is Compound A65, isotopic variants, pharmaceutically acceptable salts, solvates, hydrates, and prodrugs thereof. In one embodiment, the PI3K inhibitor is Compound A66, isotopic variants, pharmaceutically acceptable salts, solvates, hydrates, and prodrugs thereof. In one embodiment, the PI3K inhibitor is Compound A67, isotopic variants, pharmaceutically acceptable salts, solvates, hydrates, and prodrugs thereof.

Synthesis of compounds of any of the Formulae provided herein, e.g., Formulae (I), (IX), (X), (XI), and/or (XVI), is described in U.S. Pat. No. 9,056,852 B2, which is incorporated by reference for such disclosure.

CD20 Inhibitors

Described herein are PI3K inhibitors in combination with CD20 inhibitors.

B lymphocytes are the origin of humoral immunity, represent a substantial portion of hematopoietic malignancies, and contribute to autoimmunity. Consequently, cell surface molecules expressed by B cells and their malignant counterparts are important targets for immunotherapy. CD20, a B cell-specific member of the MS4A gene family, is expressed on the surface of immature and mature B cells and their malignant counterparts.

A limited analysis of CD20 transcripts in mouse cell lines and tissues suggests that mouse CD20 is also B cell-specific. Both human and mouse CD20 cDNAs encode a membrane-embedded protein with hydrophobic regions of sufficient length to pass through the membrane four times. Mouse and human CD20 are well conserved (73%) in amino acid sequence, particularly the transmembrane and long amino- and carboxyl-terminal cytoplasmic domains. The cytoplasmic domains are serine- and threonine-rich with multiple consensus sequences for phosphorylation. Human CD20 is not glycosylated, but three isoforms (33-, 35- and 37,000 Mr) result from the differential phosphorylation of a single protein on different serine and threonine residues.

CD20 plays a role in the regulation of human B cell activation, proliferation, and $Ca^{2+}$ transport. Antibody ligation of CD20 can generate transmembrane signals that result in enhanced CD20 phosphorylation, induction of c-myc and B-myb oncogene expression, induced serine/threonine and tyrosine phosphorylation of cellular proteins, increased CD18, CD58 and MHC class II molecule expression, and protein tyrosine kinase activation that induces B cell adhesion. CD20 ligation promotes transmembrane $Ca^{2+}$ transport, but does not usually lead to increased intracellular calcium $([Ca^{2+}]_i)_3$ levels, except after extensive crosslinking. Antibody binding to CD20 inhibits B cell progression from the G1 phase into the S/G2+M stages of cell cycle following mitogen stimulation, and inhibits mitogen-induced B cell differentiation and antibody secretion. Extensive CD20 cross-linking can also influence apoptosis. These divergent observations may be explained in part by the finding that CD20 is a component of an oligomeric complex that forms a membrane transporter or $Ca^{2+}$ ion channel that is activated during cell cycle progression. Despite this, B cell development and function in a line of CD20-deficient (CD20-/-) mice is reported to be normal.

The majority of human B cell-lineage malignancies express CD20. Chimeric or radiolabeled monoclonal antibody-based therapies directed against CD20 have been used for B cell malignancies such as non-Hodgkin's lymphoma.

Any suitable CD20 inhibitor may be used in combination with a PI3K inhibitor described herein. In some embodiments, the CD20 inhibitor is an antagonist of CD20. In some embodiments, the CD20 inhibitor is an antibody, variant, or biosimilar thereof. In some embodiments, the CD20 inhibitor is a monoclonal antibody.

Some embodiments provided herein describe a pharmaceutical compositions or methods for using the pharmaceutical compositions comprising a PI3K inhibitor described herein in combination with a CD20 inhibitor. CD20 inhibitors for use in pharmaceutical compositions and methods provided herein include but are not limited to ofatumumab, obinutuzumab, rituximab, ocaratuzumab, ocrelizumab, tositumomab, ibritumomab tiuxetan, tisotumab vedotin, ublituximab, TRU-015, veltuzumab, BTCT4465A (RG7828), EDC9, MT-3724, BLX-301, 1 F5, ATCC deposit HB-96450, BM-ca, C2H7, PRO131921, BVX-20, MEDI- 522, or a variant or biosimilar thereof, or combinations thereof. In some embodiments, the CD20 inhibitor for use in pharmaceutical compositions and methods provided herein is ofatumumab, obinutuzumab, rituximab, ocaratuzumab, ocrelizumab, tositumomab, ibritumomab tiuxetan, tisotumab vedotin, ublituximab, TRU-015, veltuzumab, BTCT4465A (RG7828), EDC9, MT-3724, or a variant or biosimilar thereof, or combinations thereof. In some embodiments, the CD20 inhibitor for use in pharmaceutical compositions and methods provided herein is ofatumumab, obinutuzumab, rituximab, ocaratuzumab, ocrelizumab, tositumomab, ibritumomab tiuxetan, tisotumab vedotin, ublituximab, veltuzumab, or a variant or biosimilar thereof, or combinations thereof. In some embodiments, the CD20 inhibitor for use in pharmaceutical compositions and methods provided herein is obinutuzumab or rituximab, or a variant or biosimilar thereof, or combinations thereof.

In some embodiments, the CD20 inhibitor is ofatumumab, an ofatumumab variant, or an ofatumumab biosimilar. In some embodiments, the CD20 inhibitor is obinutuzumab, an obinutuzumab variant, or an obinutuzumab biosimilar. In some embodiments, the CD20 inhibitor is rituximab, a rituximab variant, or a rituximab biosimilar. In some embodiments, the rituximab biosimilar is CT-P10, Reditux®, ABP 798, AcellBia, BI 695500, Maball, JHL1101, Novex, MabionCD20, PF-05280586, Kikuzubam, SAIT101, GP 2013, HLX01, CMAB304, BT-D004, AP-052 or TL-011. In some embodiments, the CD20 inhibitor is ocaratuzumab, an ocaratuzumab variant, or an ocaratuzumab biosimilar. In some embodiments, the CD20 inhibitor is ocrelizumab, an ocrelizumab variant, or an ocrelizumab biosimilar. In some embodiments, the CD20 inhibitor is tositumomab, a tositumomab variant, or a tositumomab biosimilar. In some embodiments, the CD20 inhibitor is ibritumomab tiuxetan, an ibritumomab tiuxetan variant, or an ibritumomab tiuxetan biosimilar. In some embodiments, the CD20 inhibitor is tisotumab vedotin, a tisotumab vedotin variant, or a tisotumab vedotin biosimilar. In some embodiments, the CD20 inhibitor is ublituximab, an ublituximab variant, or an ublituximab biosimilar. In some embodiments, the CD20 inhibitor is TRU-015, a TRU-015 variant, or a TRU-015 biosimilar. In some embodiments, the CD20 inhibitor is veltuzumab, a veltuzumab variant, or a veltuzumab biosimilar. In some embodiments, the CD20 inhibitor is BTCT4465A (RG7828), a BTCT4465A (RG7828) variant, or a BTCT4465A (RG7828) biosimilar. In some embodiments, the CD20 inhibitor is EDC9, an EDC9 variant, or an EDC9 biosimilar. In some embodiments, the CD20 inhibitor is MT-3724, a MT-3724 variant, or a MT-3724 biosimilar.

Methods of Use

Idelalisib is a PI3K inhibitor studied for relapsed chronic lymphocytic leukemia (CLL) in combination with rituximab. However, the combination of idelalisib and a CD20 inhibitor (e.g., rituximab or ofatumumab) has demonstrated an alarming increase in the risk of death due to infection and/or severe adverse effects, limiting the utility of the combination. Undesirable effects observed include but are not limited to infections, neutropenia, diarrhea/colitis, elevated liver transaminases (alanine aminotransferase/aspartate aminotransferase >5× upper limit of normal), pneumonitis, rash, hepatic impairment, renal impairment, pyrexia, increased triglycerides, or combinations thereof. Combinations of a PI3K inhibitor and a CD20 inhibitor with reduced side effects are needed to effectively treat cancers described herein (e.g., CLL).

Some embodiments provided herein describe a method for treating or preventing a proliferative disease or disorder comprising administering a PI3K inhibitor in combination with a CD20 inhibitor. In some embodiments provided herein is a method for preventing relapse of a proliferative disease or disorder, the method comprising administering a PI3K inhibitor in combination with a CD20 inhibitor. In some embodiments provided herein is a method for achieving and retaining partial cancer remission, the method comprising administering a PI3K inhibitor in combination with a CD20 inhibitor. In some embodiments provided herein is a method for achieving and retaining complete cancer remission, the method comprising administering a PI3K inhibitor in combination with a CD20 inhibitor. In some embodiments, the combination therapy of a PI3K inhibitor described herein (e.g., a compound of Formula (I)) and a CD20 inhibitor provides a synergistic effect. In some embodiments, the combination therapy of a PI3K inhibitor described herein (e.g., a compound of Formula (I)) and a CD20 inhibitor provides a synergistic antitumor or anticancer activity. In certain embodiments, the combination therapy described herein permits the use of lower dosages of the PI3K inhibitor and/or the CD20 inhibitor. In some embodiments, the combination therapy described herein permits less frequent administration of the PI3K inhibitor and/or the CD20 inhibitor to a subject. In some embodiments, the combination therapy described herein reduces the toxicity associated with the administration of the PI3K inhibitor and/or the CD20 inhibitor to a subject without reducing the efficacy in the prevention, management, treatment, or amelioration of cancer, such as a B cell malignancy. In some embodiments, the synergistic effect observed with the combination therapy described herein results in improved efficacy of therapies in the prevention, management, treatment, or amelioration of cancer, such as a B cell malignancy.

In some embodiments, the combination therapy described herein avoids or reduces adverse or unwanted side effects associated with the use of the PI3K inhibitor and/or the CD20 inhibitor. In some embodiments, the combination therapy described herein avoids, reduces, or minimizes the risk of death due to infections. In some embodiments, the combination therapy described herein avoids, reduces, or minimizes infections, neutropenia, diarrhea/colitis, elevated liver transaminases (alanine aminotransferase/aspartate aminotransferase >5× upper limit of normal), pneumonitis, rash, hepatic impairment, renal impairment, pyrexia, or increased triglycerides, or a combination thereof in patients receiving the combination therapy. In certain embodiments, the combination therapy described herein avoids, reduces, or minimizes the incidence of infection associated with the use of the PI3K inhibitor and/or the CD20 inhibitor. In certain embodiments, the combination therapy described herein avoids, reduces, or minimizes the incidence of neutropenia. In certain embodiments, the combination therapy described herein avoids, reduces, or minimizes the incidence of diarrhea/colitis. In certain embodiments, the combination therapy described herein avoids, reduces, or minimizes the incidence of elevated liver transaminases. In certain embodiments, the combination therapy described herein avoids, reduces, or minimizes the incidence of pneumonitis. In certain embodiments, the combination therapy described herein avoids, reduces, or minimizes the incidence of a rash. In certain embodiments, the combination therapy described herein avoids, reduces, or minimizes the incidence of hepatic impairment or renal impairment. In certain embodiments, the combination therapy described herein avoids, reduces, or minimizes the incidence of pyrexia. In certain embodiments, the combination therapy described herein avoids, reduces, or minimizes the incidence of increased triglycerides. In certain embodiments, the combination therapy described herein avoids, reduces, or minimizes enterocolitis (manifested as diarrhea), cutaneous toxicities, liver toxicity (manifested as elevation of transaminases), pulmonary toxicity (manifested as non-infectious pneumonitis), infections, or combinations thereof.

In some embodiments, the combination therapy described herein provides a high objective response rate (ORR) as determined by tumor assessment from radiological tests and/or physical examination. In some embodiments, the combination therapy described herein provides a durable response (DR) and/or increased durable response rate (DRR; a continuous response [complete or partial objective response] beginning within 12 months of treatment and lasting ≥6 months) in the subject or patient. In some embodiments, the combination therapy described herein provides complete remission. In some embodiments, the combination therapy described herein provides a better response compared to the monotherapy treatment of a compound of formula (I) and/or a CD20 inhibitor. In some embodiments, the combination therapy described herein provides complete remission beginning within 12 months of treatment and lasting ≥6 months. In some embodiments, the combination therapy described herein provides a complete response (CR) and/or no evidence of disease (NED) beginning within 12 months of treatment and lasting ≥6 months.

In certain embodiments, provided herein are methods for treating or preventing a disease comprising administering an effective amount of a compound of Formula (I), or an isotopic variant thereof or a pharmaceutically acceptable salt, solvate, hydrate, or prodrug thereof and an effective amount of a CD20 inhibitor. In some embodiments, the compound of Formula (I) is Compound A35 or an isotopic variant, pharmaceutically acceptable salt, solvate, hydrate, or prodrug thereof. In some embodiments, the compound of Formula (I) is Compound A36 or an isotopic variant, pharmaceutically acceptable salt, solvate, hydrate, or prodrug thereof. In some embodiments, the compound of Formula (I) is Compound A68 or an isotopic variant, pharmaceutically acceptable salt, solvate, hydrate, or prodrug thereof. In some embodiments, the compound of Formula (I) is Compound A70 or an isotopic variant, pharmaceutically acceptable salt, solvate, hydrate, or prodrug thereof. In some embodiments, the compound of Formula (I) is Compound A37 or an isotopic variant, pharmaceutically acceptable salt, solvate, hydrate, or prodrug thereof. In some embodiments, the compound of Formula (I) is Compound A38 or an isotopic variant, pharmaceutically acceptable salt, solvate, hydrate, or prodrug thereof. In some embodiments, the compound of Formula (I) is Compound A41 or an isotopic variant, pharmaceutically acceptable salt, solvate, hydrate, or prodrug thereof. In some embodiments, the compound of Formula (I) is Compound A42 or an isotopic variant, pharmaceutically acceptable salt, solvate, hydrate, or prodrug thereof. In some embodiments, the compound of Formula (I) is Compound A43 or an isotopic variant, pharmaceutically acceptable salt, solvate, hydrate, or prodrug thereof. In some embodiments, the compound of Formula (I) is Compound A44 or an isotopic variant, pharmaceutically acceptable salt, solvate, hydrate, or prodrug thereof. In some embodiments, the compound of Formula (I) is Compound A62 or an isotopic variant, pharmaceutically acceptable salt, solvate, hydrate, or prodrug thereof. In some embodiments, the compound of Formula (I) is Compound A63 or an isotopic variant, pharmaceutically acceptable salt, solvate, hydrate, or prodrug thereof. In some embodiments, the compound of Formula (I) is Compound A64 or an isotopic variant, pharmaceutically acceptable salt, solvate, hydrate, or prodrug thereof. In some embodiments, the compound of Formula (I) is Compound A65 or an isotopic variant, pharmaceutically acceptable salt, solvate, hydrate, or prodrug thereof. In some embodiments, the compound of Formula (I) is Compound A66 or an isotopic variant, pharmaceutically acceptable salt, solvate, hydrate, or prodrug thereof. In some embodiments, the compound of Formula (I) is Compound A67 or an isotopic variant, pharmaceutically acceptable salt, solvate, hydrate, or prodrug thereof. In some embodiments, the CD20 inhibitor is ofatumumab, obinutuzumab, rituximab, ocaratuzumab, ocrelizumab, tositumomab, ibritumomab tiuxetan, tisotumab vedotin, ublituximab, TRU-015, veltuzumab, BTCT4465A (RG7828), EDC9, MT-3724, or a variant or biosimilar thereof. In some embodiments, the CD20 inhibitor is rituximab.

In some embodiments, the compound of Formula (I) is Compound A35 or an isotopic variant, pharmaceutically acceptable salt, solvate, hydrate, or prodrug thereof and the CD20 inhibitor is rituximab, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is obinutuzumab, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is ofatumumab, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is ocaratuzumab, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is tositumomab, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is ibritumomab tiuxetan, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is ublituximab, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is EDC9, or a variant, or biosimilar thereof. In some embodiments, the compound of Formula (I) is Compound A35 or an isotopic variant, pharmaceutically acceptable salt, solvate, hydrate, or prodrug thereof and the CD20 inhibitor is MT-3724, or a variant, or biosimilar thereof.

In some embodiments, the compound of Formula (I) is Compound A36 or an isotopic variant, pharmaceutically acceptable salt, solvate, hydrate, or prodrug thereof and the CD20 inhibitor is rituximab, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is obinutuzumab, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is ofatumumab, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is ocaratuzumab, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is tositumomab, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is ibritumomab tiuxetan, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is ublituximab, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is EDC9, or a variant, or biosimilar thereof. In some embodiments, the compound of Formula (I) is Compound A36 or an isotopic variant, pharmaceutically acceptable salt, solvate, hydrate, or prodrug thereof and the CD20 inhibitor is MT-3724, or a variant, or biosimilar thereof.

In some embodiments, the compound of Formula (I) is Compound A68 or an isotopic variant, pharmaceutically acceptable salt, solvate, hydrate, or prodrug thereof and the CD20 inhibitor is rituximab, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is obinutuzumab, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is ofatumumab, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is ocaratuzumab, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is tositumomab, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is ibritumomab tiuxetan, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is ublituximab, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is EDC9, or a variant, or biosimilar thereof. In some embodiments, the compound of Formula (I) is Compound A68 or an isotopic variant, pharmaceutically acceptable salt, solvate, hydrate, or prodrug thereof and the CD20 inhibitor is MT-3724, or a variant, or biosimilar thereof.

In some embodiments, the compound of Formula (I) is Compound A70 or an isotopic variant, pharmaceutically acceptable salt, solvate, hydrate, or prodrug thereof and the CD20 inhibitor is rituximab, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is obinutuzumab, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is ofatumumab, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is ocaratuzumab, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is tositumomab, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is ibritumomab tiuxetan, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is ublituximab, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is EDC9, or a variant, or biosimilar thereof. In some embodiments, the compound of Formula (I) is Compound A70 or an isotopic variant, pharmaceutically acceptable salt, solvate, hydrate, or prodrug thereof and the CD20 inhibitor is MT-3724, or a variant, or biosimilar thereof.

In some embodiments, the compound of Formula (I) is Compound A37 or an isotopic variant, pharmaceutically acceptable salt, solvate, hydrate, or prodrug thereof and the CD20 inhibitor is rituximab, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is obinutuzumab, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is ofatumumab, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is ocaratuzumab, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is tositumomab, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is ibritumomab tiuxetan, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is ublituximab, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is EDC9, or a variant, or biosimilar thereof. In some embodiments, the compound of Formula (I) is Compound A37 or an isotopic variant, pharmaceutically acceptable salt, solvate, hydrate, or prodrug thereof and the CD20 inhibitor is MT-3724, or a variant, or biosimilar thereof.

In some embodiments, the proliferative disease is cancer. In certain embodiments, the proliferative disease is a hematological malignancy.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, non-secretory myeloma, osteosclerotic myeloma, plasma cell leukemia, solitary plasmacytoma, and extramedullary plasmacytoma; (6) Waldenstrom's macroglobulinernia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, aligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mutinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prol actin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, non-serninoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; (42) reproductive cancers, such as cervical cancer, uterus cancer, ovarian cancer, or testicular cancer; (43) esophagus cancer; (44) laryngeal cancer; (45) head and neck cancer (such as mouth, nose, throat, larynx, sinuses, or salivary glands cancer); and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). In some embodiments, the cancer is non-small cell lung cancer, melanoma, renal cell cancer, head and neck cancer, colon cancer, or mesothelioma. In some embodiments, the cancer is non-small cell lung cancer. In some embodiments, the cancer is melanoma.

In certain embodiments, provided herein are methods of treating hematological malignancy with a combination of an effective amount of a compound of Formula (I), or an isotopic variant thereof; or a pharmaceutically acceptable salt, solvate, hydrate, or prodrug thereof and an effective amount of CD20 inhibitor in a patient. In certain embodiments, the hematological malignancy is a leukemia, a lymphoma, a myeloma, a non-Hodgkin's lymphoma, a Hodgkin's lymphoma, T-cell malignancy, or a B-cell malignancy. In some embodiments, the hematological malignancy is Hodgkin's lymphoma.

In certain embodiments, the hematological malignancy is a T-cell malignancy. In certain embodiments, T-cell malignancies include peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In certain embodiments, the hematological malignancy is a B-cell malignancy. In some embodiments, the synergistic combination a PI3K inhibitor described herein and a CD20 inhibitor is used in the treatment of B cell malignancies. In certain embodiments, B cell malignancies include acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitts lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In certain embodiments, the B cell malignancy is selected from non-Hodgkin's lymphoma, Burkitt's lymphoma, small lymphocytic lymphoma, primary effusion lymphoma, diffuse large B-cell lymphoma, splenic marginal zone lymphoma, MALT (mucosa-associated lymphoid tissue) lymphoma, hairy cell leukemia, chronic lymphocytic leukemia, B-cell prolymphocytic leukemia, B cell lymphomas (e.g. various forms of Hodgkin's disease, B cell non-Hodgkin's lymphoma (NHL), leukemias (e.g. acute lymphoblastic leukemia (ALL), chronic lymphocytic leukemia (CLL; also termed B cell chronic lymphocytic leukemia BCLL), hairy cell leukemia and chronic myoblastic leukemia) and myelomas (e.g. multiple myeloma). In certain embodiments, the B-cell malignancy is diffuse large B-cell lymphoma (DLBCL). In certain embodiments, the hematological malignancy is diffuse large B-cell lymphoma (DLBCL). In certain embodiments, the DLBCL is an activated B-cell DLBCL (ABC-DLBCL), a germinal center B-cell like DLBCL (GBC-DLBCL), a double hit DLBCL (DH-DLBCL), or a triple hit DLBCL (TH-DLBCL). In some embodiments, the hematological malignancy is B-cell non-Hodgkin's lymphoma (NHL). In some embodiments, the hematological malignancy is B-cell indolent non-Hodgkin's lymphoma (NHL). In certain embodiments, the B-cell malignancy is selected from chronic lymphocytic leukemia (CLL), small lymphocytic lymphoma (SLL), follicular lymphoma (FL), marginal zone B cell lymphoma (MZL), diffuse large B-cell lymphoma (DLBCL), and high grade non-Hodgkin's lymphoma. In certain embodiments, the B-cell malignancy is selected from chronic lymphocytic leukemia (CLL), follicular lymphoma (FL), marginal zone B cell lymphoma (MZL), or diffuse large B-cell lymphoma (DLBCL).

In certain embodiments, the hematological malignancy is a relapsed or refractory hematological malignancy. In certain embodiments, the relapsed or refractory hematological malignancy is a relapsed or refractory T-cell malignancy. In certain embodiments, the relapsed or refractory hematological malignancy is a relapsed or refractory B-cell malignancy. In some embodiments, the cancer is relapsed B-cell non-Hodgkin's lymphoma (NHL) or chronic lymphocytic leukemia (CLL). In some embodiments, the hematological malignancy is relapsed B-cell non-Hodgkin's lymphoma (NHL) or chronic lymphocytic leukemia (CLL).

Dosages and Dosing Regimens

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration as described elsewhere herein.

In certain embodiments, the methods provided herein comprise administering a compound of Formula (I), or an isotopic variant thereof; or a pharmaceutically acceptable salt, solvate, hydrate, or prodrug thereof and a CD20 inhibitor to a patient simultaneously or sequentially by the same or different routes of administration.

The suitability of a particular route of administration employed for a particular active agent will depend on the active agent itself (e.g., whether it can be administered orally without decomposing prior to entering the blood stream) and the disease being treated.

In certain embodiments, the compound of Formula (I), or an isotopic variant thereof; or a pharmaceutically acceptable salt, solvate, hydrate, or prodrug thereof and a CD20 inhibitor is administered simultaneously, at essentially the same time, or sequentially. If administration takes place sequentially, the CD20 inhibitor may be administered before or after administration of a compound of Formula (I), or an isotopic variant thereof; or a pharmaceutically acceptable salt, solvate, hydrate, or prodrug thereof. In some embodiments, the CD20 inhibitor is administered before administration of a compound of Formula (I), or an isotopic variant thereof; or a pharmaceutically acceptable salt, solvate, hydrate, or prodrug thereof. In some embodiments, the CD20 inhibitor is administered simultaneously with administration of a compound of Formula (I), an isotopic variant thereof; or a pharmaceutically acceptable salt, solvate, hydrate, or prodrug thereof. In some embodiments, the CD20 inhibitor is administered after the administration of a compound of Formula (I), an isotopic variant thereof; or a pharmaceutically acceptable salt, solvate, hydrate, or prodrug thereof.

A compound of Formula (I), or an isotopic variant thereof; or a pharmaceutically acceptable salt, solvate, hydrate, or prodrug thereof and the CD20 inhibitor need not be administered by means of the same vehicle. In some embodiments, the CD20 inhibitor and a compound of Formula (I), or an isotopic variant thereof; or a pharmaceutically acceptable salt, solvate, hydrate, or prodrug thereof are administered in different vehicles. The CD20 inhibitor may be administered one or more times, and the number of administrations of each component of the combination may be the same or different. In addition, a compound of Formula (I), or an isotopic variant thereof, or a pharmaceutically acceptable salt, solvate, hydrate, or prodrug thereof and the CD20 inhibitor need not be administered at the same site.

In some instances, the methods described herein further comprise administering the PI3K inhibitor in combination with CD20 inhibitor to the subject or patient in need thereof in multiple cycles repeated on a regular schedule with periods of rest in between each cycle. For example, in some instances, treatment is given for one week followed by three weeks of rest is one treatment cycle.

In some instances, a cycle comprises administration of the PI3K inhibitor at the same time as administration of the CD20 inhibitor. In some instances, the PI3K inhibitor and the CD20 inhibitor are administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some instances, a cycle comprises administration of the PI3K inhibitor first followed by administration of the CD20 inhibitor second. In some instances, the PI3K inhibitor is administered for about 1 day, about 2 days, about 3 days, about 4 days, about 5 days, about 6 days, about 7 days, about 8 days, about 9 days, about 10 days, about 11 days, about 12 days, about 13 days, or about 14 days followed by administration of the CD20 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days.

In some instances, a cycle comprises administration of the PI3K inhibitor first followed by concurrent administration of the CD20 inhibitor. In some instances, the PI3K inhibitor is first administered for about 1 day, about 2 days, about 3 days, about 4 days, about 5 days, about 6 days, about 7 days, about 8 days, about 9 days, about 10 days, about 11 days, about 12 days, about 13 days, or about 14 days followed by the concurrent administration of the CD20 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days. In some instances, the PI3K inhibitor is first administered for about 1 day, about 2 days, about 3 days, about 4 days, about 5 days, about 6 days, or about 7 days followed by the concurrent administration of the CD20 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days. In some instances, the PI3K inhibitor is first administered for about 7 days followed by the concurrent administration of the CD20 inhibitor for about 1 day, about 2 days, about 3 days, about 4 days, about 5 days, about 6 days, about 7 days, about 8 days, about 9 days, about 10 days, about 11 days, about 12 days, about 13 days, or about 14 days. In some instances, the PI3K inhibitor is first administered for about 7 days followed by the concurrent administration of the CD20 inhibitor for about 10 days, about 11 days, about 12 days, about 13 days, or about 14 days.

In some instances, a cycle comprises administration of the PI3K inhibitor only. In some instances, the PI3K inhibitor is administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some instances, a cycle comprises administration of the the CD20 inhibitor only. In some instances, the CD20 inhibitor is administered for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some instances, the method for multiple cycle chemotherapy comprises the administration of a second cycle within about 60 days or about 3 months. In some instances, the method for multiple cycle chemotherapy comprises the administration of a second cycle within 50 days. In another instance, the second cycle is administered within 45, 40, 35, 30, 25, 21, 20, 15, 14, 10, 9, 8, 7, 6, 5, 4, 3, 2 or 1 day(s) of the first cycle. In some embodiments, the administration of any additional cycles is within 50 days of the previous cycle. In some embodiments, the administration of any additional cycles is within 10 days of the previous cycle. In some embodiments, the administration of any additional cycles is within 9 days of the previous cycle. In some embodiments, the administration of any additional cycles is within 8 days of the previous cycle. In some embodiments, the administration of any additional cycles is within 7 days of the previous cycle. In some embodiments, the administration of any additional cycles is within 6 days of the previous cycle. In some embodiments, the administration of any additional cycles is within 5 days of the previous cycle. In some embodiments, the administration of any additional cycles is within 4 days of the previous cycle. In some embodiments, the administration of any additional cycles is within 3 days of the previous cycle. In some embodiments, the administration of any additional cycles is within 2 days of the previous cycle. In some embodiments, the administration of any additional cycles is within 1 day of the previous cycle. In another embodiment, the additional cycle is administered within 45, 40, 35, 30, 25, 21, 20, 15, 14, 10, 9, 8, 7, 6, 5, 4, 3, 2, or 1 days of the previous cycle.

The length of a treatment cycle depends on the treatment being given. In some embodiments, the length of a treatment cycle ranges from two to six weeks. In some embodiments, the length of a treatment cycle ranges from four to six weeks. In some embodiments, the length of a treatment cycle is 28 days. In some embodiments, the length of a treatment cycle is 56 days. In some embodiments, a treatment cycle lasts one, two, three, or four weeks. In some embodiments, a treatment cycle lasts four weeks. The number of treatment doses scheduled within each cycle also varies depending on the drugs being given.

In certain instances, the compound of Formula (I), or an isotopic variant thereof; or a pharmaceutically acceptable salt, solvate, hydrate, or prodrug thereof, is administered to the subject on a 28-day cycle. In some embodiments, the compound of Formula (I), or an isotopic variant thereof; or a pharmaceutically acceptable salt, solvate, hydrate, or prodrug thereof, is administered to the subject for at least one 28-day cycle. In some embodiments, the compound of Formula (I), or an enantiomer, a mixture of enantiomers, a mixture of two or more diastereomers, or an isotopic variant thereof; or a pharmaceutically acceptable salt, solvate, hydrate, or prodrug thereof, is administered to the subject for at least two 28-day cycles.

In certain embodiments, the compound of Formula (I), or an enantiomer, a mixture of enantiomers, a mixture of two or more diastereomers, or an isotopic variant thereof; or a pharmaceutically acceptable salt, solvate, hydrate, or prodrug thereof, is administered to the subject for a period of up to about 7 days. In some embodiments, the days over which the compound of Formula (I), or an enantiomer, a mixture of enantiomers, a mixture of two or more diastereomers, or an isotopic variant thereof; or a pharmaceutically acceptable salt, solvate, hydrate, or prodrug thereof are intermittent. In some embodiments, administering to subject the compound of Formula (I), or an enantiomer, a mixture of enantiomers, a mixture of two or more diastereomers, or an isotopic variant thereof; or a pharmaceutically acceptable salt, solvate, hydrate, or prodrug thereof for about 7 consecutive days in a 28-day cycle.

In some embodiments, the method comprises an intermittent dosing schedule (IS), comprising administering to subject the compound of Formula (I), or an enantiomer, a mixture of enantiomers, a mixture of two or more diastereomers, or an isotopic variant thereof; or a pharmaceutically acceptable salt, solvate, hydrate, or prodrug thereof once daily for 7 consecutive days followed by 21 days without treatment in a 28-day cycle. In some embodiments, the compound of Formula (I), or an enantiomer, a mixture of enantiomers, a mixture of two or more diastereomers, or an isotopic variant thereof; or a pharmaceutically acceptable salt, solvate, hydrate, or prodrug thereof, is administered to the subject for at least one 28-day cycle. In some embodiments, the IS avoids or reduces adverse or unwanted side effects associated with the use of the PI3K inhibitor, such as enterocolitis (manifested as diarrhea), cutaneous toxicities, liver toxicity (manifested as elevation of transaminases), pulmonary toxicity (manifested as non-infectious pneumonitis), and infections. In some embodiments, the IS avoids or reduces enterocolitis, rash, transaminitis, or combinations thereof.

In some embodiments, the method comprises a continuous daily dosing schedule (CS), comprising administering to subject the compound of Formula (I), or an enantiomer, a mixture of enantiomers, a mixture of two or more diastereomers, or an isotopic variant thereof; or a pharmaceutically acceptable salt, solvate, hydrate, or prodrug thereof once daily for 28 consecutive days in a 28-day cycle. In some embodiments, the compound of Formula (I), or an enantiomer, a mixture of enantiomers, a mixture of two or more diastereomers, or an isotopic variant thereof, or a pharmaceutically acceptable salt, solvate, hydrate, or prodrug thereof, is administered to the subject for at least two CS 28-day cycles. In certain instances, the method comprises a continuous daily dosing schedule (CS) for at least two CS 28-day cycles, followed by an intermittant dosing schedule (IS), comprising administering to subject the compound of Formula (I), or an enantiomer, a mixture of enantiomers, a mixture of two or more diastereomers, or an isotopic variant thereof; or a pharmaceutically acceptable salt, solvate, hydrate, or prodrug thereof once daily for 7 consecutive days followed by 21 days without treatment in a 28-day cycle after the at least two CS 28-day cycles. In some embodiments, the dosing schedule avoids or reduces adverse or unwanted side effects associated with the use of the PI3K inhibitor, such as enterocolitis (manifested as diarrhea), cutaneous toxicities, liver toxicity (manifested as elevation of transaminases), pulmonary toxicity (manifested as non-infectious pneumonitis), and infections. In some embodiments, the dosing schedule avoids or reduces enterocolitis, rash, transaminitis, or combinations thereof.

In some instances, the method for the administration of multiple compounds comprises administering compounds within 48 hours or less of each other. In some embodiments administration occurs within 24 hours, 12 hours, 6 hours, 3 hours, 1 hour, or 15 minutes. In some instances, the compounds are administered simultaneously. One example of simultaneous administration is the injection of one compound immediately before, after, or during the oral administration of the second compound, immediately referring to a time less than about 5 minutes.

In some instances, the method for the administration of multiple compounds occurs in a sequential order, wherein the PI3K inhibitor is administered before the CD20 inhibitor. In another instance, the CD20 inhibitor is administered before the PI3K inhibitor.

In some instances, the method for administering the PI3K inhibitor is oral and the method for administering the CD20 inhibitor is by injection. In some instances, the method for administering the PI3K inhibitor is by inhalation and the method for administering the CD20 inhibitor is by injection. In some instances, the method for administering the PI3K inhibitor is by injection and the method for administering the CD20 inhibitor is by injection.

In certain embodiments, a compound of Formula (I), or an isotopic variant thereof, or a pharmaceutically acceptable salt, solvate, hydrate, or prodrug thereof and a CD20 inhibitor is cyclically administered to a patient. As discussed above, cycling therapy involves the administration of an active agent or a combination of active agents for a period of time, followed by a rest for a period of time, and repeating this sequential administration. In some embodiments, cycling therapy reduces the development of resistance to one or more of the therapies, avoid or reduce the side effects of one of the therapies, and/or improves the efficacy of the treatment.

In some embodiments, the compound of Formula (I) is administered daily, every other day, every other day 3 times a week, every 2 weeks, every 3 weeks, every 4 weeks, every 5 weeks, every 3 days, every 4 days, every 5 days, every 6 days, weekly, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some embodiments, the compound of Formula (I) is administered daily. In some embodiments, the compound of Formula (I) is administered daily for a period of up to about 28 days. In some embodiments, the compound of Formula (I) is administered daily for a period of up to about 7 days.

In some embodiments, the CD20 inhibitor is administered daily, every other day, every other day 3 times a week, every 3 days, every 4 days, every 5 days, every 6 days, weekly, every 2 weeks, every 3 weeks, every 4 weeks, every 5 weeks, bi-weekly, 3 times a week, 4 times a week, 5 times a week, 6 times a week, once a month, twice a month, 3 times a month, once every 2 months, once every 3 months, once every 4 months, once every 5 months, or once every 6 months. In some embodiments, the CD20 inhibitor is administered 8 times in 6 months.

In some instances, the compound of Formula (I) or the CD20 inhibitor is optionally given continuously; alternatively, the dose of drug being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 8 days, 9 days, 10 days, 12 days, 14 days, 15 days, 20 days, 21 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In certain embodiments, in the treatment, prevention, or amelioration of one or more symptoms of the disorders, diseases, or conditions described herein, an appropriate dosage level of a compound of Formula (I), or an isotopic variant thereof; or a pharmaceutically acceptable salt, solvate, hydrate, or prodrug thereof generally is ranging from about 1 to 1000 mg, from about 1 to about 500 mg, from about 5 to about 500 mg, from about 5 to about 200 mg, from about 5 to about 250 mg or from about 10 to about 150 mg which can be administered in single or multiple doses. In certain embodiments, the compound of Formula (I), or an isotopic variant thereof; or a pharmaceutically acceptable salt, solvate, hydrate, or prodrug thereof is administered in an amount of about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 225, 250, 275, 300, 325, 350, 375, 400, 450 or 500 mg. In certain embodiments, the compound of Formula (I), or an isotopic variant thereof; or a pharmaceutically acceptable salt, solvate, hydrate, or prodrug thereof is administered in an amount of about 60 mg, about 120 mg, about 150 mg, or about 180 mg. In certain embodiments, the compound of Formula (I), or an isotopic variant thereof; or a pharmaceutically acceptable salt, solvate, hydrate, or prodrug thereof is administered in an amount of about 60 mg. In certain embodiments, the compound of Formula (I), or an isotopic variant thereof; or a pharmaceutically acceptable salt, solvate, hydrate, or prodrug thereof is administered in an amount of about 1, about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 225, about 250, about 275, about 300, about 325, about 350, about 375, about 400, about 450, or about 500 mg/day. In certain embodiments, the compound of Formula (I), or an isotopic variant thereof; or a pharmaceutically acceptable salt, solvate, hydrate, or prodrug thereof is administered in an amount of about 45 mg/day. In certain embodiments, the compound of Formula (I), or an isotopic variant thereof; or a pharmaceutically acceptable salt, solvate, hydrate, or prodrug thereof is administered in an amount of about 60 mg/day. In certain embodiments, the compound of Formula (I), or an isotopic variant thereof; or a pharmaceutically acceptable salt, solvate, hydrate, or prodrug thereof is administered in an amount of about 90 mg/day. In certain embodiments, the compound of Formula (I), or an isotopic variant thereof; or a pharmaceutically acceptable salt, solvate, hydrate, or prodrug thereof is administered in an amount of about 120 mg/day. In certain embodiments, the compound of Formula (I), or an isotopic variant thereof; or a pharmaceutically acceptable salt, solvate, hydrate, or prodrug thereof is administered in an amount of about 150 mg/day. In certain embodiments, the compound of Formula (I), or an isotopic variant thereof; or a pharmaceutically acceptable salt, solvate, hydrate, or prodrug thereof is administered in an amount of about 180 mg/day.

For oral administration, the pharmaceutical compositions provided herein can be formulated in the form of tablets containing from about 1.0 to about 1,000 mg of a compound of Formula (I), or an isotopic variant thereof; or a pharmaceutically acceptable salt, solvate, hydrate, or prodrug thereof, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the a compound of Formula (I), or an isotopic variant thereof; or a pharmaceutically acceptable salt, solvate, hydrate, or prodrug thereof for the symptomatic adjustment of the dosage to the patient to be treated.

In some embodiments, the pharmaceutical compositions provided herein can be formulated in the form of tablets containing about 45 mg of a compound of Formula (I), or an isotopic variant thereof; or a pharmaceutically acceptable salt, solvate, hydrate, or prodrug thereof. The pharmaceutical compositions can be administered on a regimen of 1 to 4 times per day, including once, twice, three times, and four times per day. In certain embodiments, a compound of Formula (I), or an isotopic variant thereof; or a pharmaceutically acceptable salt, solvate, hydrate, or prodrug thereof is administered to a patient in need thereof in an amount of about 45 mg daily for 28 days or 56 days. In certain specific embodiments, a compound of Formula (I), or an isotopic variant thereof, or a pharmaceutically acceptable salt, solvate, hydrate, or prodrug thereof is administered to a patient in need thereof in an amount of about 45 mg daily for 28 days. In other specific embodiments, a compound of Formula (I), or an isotopic variant thereof; or a pharmaceutically acceptable salt, solvate, hydrate, or prodrug thereof is administered to a patient in need thereof in an amount of about 45 mg daily for 56 days.

In some embodiments, the pharmaceutical compositions provided herein can be formulated in the form of tablets containing about 60 mg of a compound of Formula (I), or an isotopic variant thereof; or a pharmaceutically acceptable salt, solvate, hydrate, or prodrug thereof. The pharmaceutical compositions can be administered on a regimen of 1 to 4 times per day, including once, twice, three times, and four times per day. In certain embodiments, a compound of Formula (I), or an isotopic variant thereof; or a pharmaceutically acceptable salt, solvate, hydrate, or prodrug thereof is administered to a patient in need thereof in an amount of about 60 mg daily for 28 days or 56 days. In certain specific embodiments, a compound of Formula (I), or an isotopic variant thereof; or a pharmaceutically acceptable salt, solvate, hydrate, or prodrug thereof is administered to a patient in need thereof in an amount of about 60 mg daily for 28 days. In other specific embodiments, a compound of Formula (I), or an isotopic variant thereof; or a pharmaceutically acceptable salt, solvate, hydrate, or prodrug thereof is administered to a patient in need thereof in an amount of about 60 mg daily for 56 days.

In some embodiments, the pharmaceutical compositions provided herein can be formulated in the form of tablets containing about 90 mg of a compound of Formula (I), or an isotopic variant thereof; or a pharmaceutically acceptable salt, solvate, hydrate, or prodrug thereof. The pharmaceutical compositions can be administered on a regimen of 1 to 4 times per day, including once, twice, three times, and four times per day. In certain embodiments, a compound of Formula (I), or an isotopic variant thereof; or a pharmaceutically acceptable salt, solvate, hydrate, or prodrug thereof is administered to a patient in need thereof in an amount of about 90 mg daily for 28 days or 56 days. In certain specific embodiments, a compound of Formula (I), or an isotopic variant thereof; or a pharmaceutically acceptable salt, solvate, hydrate, or prodrug thereof is administered to a patient in need thereof in an amount of about 90 mg daily for 28 days. In other specific embodiments, a compound of Formula (I), or an isotopic variant thereof; or a pharmaceutically acceptable salt, solvate, hydrate, or prodrug thereof is administered to a patient in need thereof in an amount of about 90 mg daily for 56 days.

In some embodiments, the pharmaceutical compositions provided herein can be formulated in the form of tablets containing about 120 mg of a compound of Formula (I), or an isotopic variant thereof; or a pharmaceutically acceptable salt, solvate, hydrate, or prodrug thereof. The pharmaceutical compositions can be administered on a regimen of 1 to 4 times per day, including once, twice, three times, and four times per day. In certain embodiments, a compound of Formula (I), or an isotopic variant thereof; or a pharmaceutically acceptable salt, solvate, hydrate, or prodrug thereof is administered to a patient in need thereof in an amount of about 120 mg daily for 28 days or 56 days. In certain specific embodiments, a compound of Formula (I), or an isotopic variant thereof; or a pharmaceutically acceptable salt, solvate, hydrate, or prodrug thereof is administered to a patient in need thereof in an amount of about 120 mg daily for 28 days. In other specific embodiments, a compound of Formula (I), or an isotopic variant thereof; or a pharmaceutically acceptable salt, solvate, hydrate, or prodrug thereof is administered to a patient in need thereof in an amount of about 120 mg daily for 56 days.

In some embodiments, the pharmaceutical compositions provided herein can be formulated in the form of tablets containing about 150 mg of a compound of Formula (I), or an isotopic variant thereof; or a pharmaceutically acceptable salt, solvate, hydrate, or prodrug thereof. The pharmaceutical compositions can be administered on a regimen of 1 to 4 times per day, including once, twice, three times, and four times per day. In certain embodiments, a compound of Formula (I), or an isotopic variant thereof; or a pharmaceutically acceptable salt, solvate, hydrate, or prodrug thereof is administered to a patient in need thereof in an amount of about 150 mg daily for 28 days or 56 days. In certain specific embodiments, a compound of Formula (I), or an isotopic variant thereof, or a pharmaceutically acceptable salt, solvate, hydrate, or prodrug thereof is administered to a patient in need thereof in an amount of about 150 mg daily for 28 days. In other specific embodiments, a compound of Formula (I), or an isotopic variant thereof, or a pharmaceutically acceptable salt, solvate, hydrate, or prodrug thereof is administered to a patient in need thereof in an amount of about 150 mg daily for 56 days.

In some embodiments, the pharmaceutical compositions provided herein can be formulated in the form of tablets containing about 180 mg of a compound of Formula (I), or an isotopic variant thereof; or a pharmaceutically acceptable salt, solvate, hydrate, or prodrug thereof. The pharmaceutical compositions can be administered on a regimen of 1 to 4 times per day, including once, twice, three times, and four times per day. In certain embodiments, a compound of Formula (I), or an isotopic variant thereof; or a pharmaceutically acceptable salt, solvate, hydrate, or prodrug thereof is administered to a patient in need thereof in an amount of about 180 mg daily for 28 days or 56 days. In certain specific embodiments, a compound of Formula (I), or an isotopic variant thereof, or a pharmaceutically acceptable salt, solvate, hydrate, or prodrug thereof is administered to a patient in need thereof in an amount of about 180 mg daily for 28 days. In other specific embodiments, a compound of Formula (I), or an isotopic variant thereof; or a pharmaceutically acceptable salt, solvate, hydrate, or prodrug thereof is administered to a patient in need thereof in an amount of about 180 mg daily for 56 days.

In certain embodiments, the CD20 inhibitor used in combination with a compound of Formula (I), or an isotopic variant thereof, or a pharmaceutically acceptable salt, solvate, hydrate, or prodrug, is rituximab. In certain embodiments, the methods described herein further comprise administering rituximab as an intravenous infusion in 28 days cycles. In certain embodiments, rituximab is administered as an intravenous infusion for multiple 28 days cycles. In certain embodiments, rituximab is administered as an intravenous infusion at a dose of 375 mg/m$^2$ in the first cycle and 500 mg/m$^2$ in cycles 2-6. In certain embodiments, rituximab is administered intravenously as an infusion at a dose of 375 mg/m$^2$ per cycle. In certain embodiments, rituximab is administered as an intravenous infusion at a dose of 375 mg/m$^2$ for a total of 8 doses in 6 months.

In certain embodiments, the CD20 inhibitor used in combination with a compound of Formula (I), or an isotopic variant thereof, or a pharmaceutically acceptable salt, solvate, hydrate, or prodrug, is ofatumumab. In certain embodiments, the methods described herein further comprise administering ofatumumab as an intravenous infusion every week. In certain embodiments, ofatumumab is administered as an intravenous infusion for multiple cycles. In certain embodiments, ofatumumab is administered as an intravenous infusion at a dose of 300 mg initial dose, followed 1 week later by 2,000 mg weekly for 7 doses, followed 4 weeks later by 2,000 mg every 4 weeks for 4 doses.

In certain embodiments, the CD20 inhibitor used in combination with a compound of Formula (I), or an isotopic variant thereof; or a pharmaceutically acceptable salt, solvate, hydrate, or prodrug, is obinutuzumab. In certain embodiments, the methods described herein further comprise administering obinutuzumab as an intravenous infusion in 28 days cycles. In certain embodiments, obinutuzumab is administered as an intravenous infusion for multiple cycles 28 days cycles. In certain embodiments, obinutuzumab is administered as an intravenous infusion at a dose of 100 mg on day 1 and 900 mg on day 2 Cycle 1, 1000 mg on day 8 and 15 of Cycle 1, and 1000 mg on day 1 of Cycles 2-6. In certain embodiments, obinutuzumab is administered as an intravenous infusion at a dose of 1000 mg on day 1, 8 and 15 of Cycle 1, and 1000 mg on day 1 of Cycles 2-6, and then every 2 months for 2 years.

In certain embodiments, the CD20 inhibitor used in combination with a compound of Formula (I), or an isotopic variant thereof; or a pharmaceutically acceptable salt, solvate, hydrate, or prodrug, is ocaratuzumab. In certain embodiments, the methods described herein further comprise administering ocaratuzumab as a subcutaneous injection every week. In certain embodiments, ocaratuzumab is administered as a subcutaneous injection for multiple cycles. In certain embodiments, ocaratuzumab is administered at a dose between about 20 mg to about 100 mg per week. In certain embodiments, ocaratuzumab is administered at a dose of about 40 mg per week. In certain embodiments, ocaratuzumab is administered at a dose of about 80 mg per week.

In certain embodiments, the CD20 inhibitor used in combination with a compound of Formula (I), or an isotopic variant thereof; or a pharmaceutically acceptable salt, solvate, hydrate, or prodrug, is ocrelizumab. In certain embodiments, the methods described herein further comprise administering ocrelizumab as an intravenous infusion in 24 weeks cycles. In certain embodiments, ocrelizumab is administered as an intravenous infusion for multiple cycles. In certain embodiments, ocrelizumab is administered as an intravenous infusion at a dose of 600 mg as a 300 mg infusions on days 1 and 15 for the first dose and as a single infusion of 600 mg for all subsequent infusions every 24 weeks.

In certain embodiments, the CD20 inhibitor used in combination with a compound of Formula (I), or an isotopic variant thereof; or a pharmaceutically acceptable salt, solvate, hydrate, or prodrug, is ublituximab. In certain embodiments, the methods described herein further comprise administering ublituximab as an intravenous infusion in cycles. In certain embodiments, ublituximab is administered as an intravenous infusion for multiple cycles. In certain embodiments, ublituximab is administered as an intravenous infusion at day 1, day 8 and day 15 of every cycle.

In certain embodiments, the CD20 inhibitor used in combination with a compound of Formula (I), or an isotopic variant thereof; or a pharmaceutically acceptable salt, solvate, hydrate, or prodrug, is BTCT4465A. In certain embodiments, the methods described herein further comprise administering BTCT4465A as an intravenous infusion in 21 days cycles. In certain embodiments, BTCT4465A is administered as an intravenous infusion for multiple cycles. In certain embodiments, BTCT4465A is administered as an intravenous infusion on Day 1 of each 21-day cycle. In certain embodiments, BTCT4465A is administered as an intravenous infusion on Days 1, 8, and 15 of Cycle 1 and thereafter on Day 1 of each 21-day cycle.

In certain embodiments, the CD20 inhibitor used in combination with a compound of Formula (I), or an isotopic variant thereof; or a pharmaceutically acceptable salt, solvate, hydrate, or prodrug, is veltuzumab. In certain embodiments, the methods described herein further comprise administering veltuzumab as an intravenous infusion or a subcutaneous injection in weekly cycles. In certain embodiments, veltuzumab is administered as an intravenous infusion or a subcutaneous injection for multiple weekly cycles. In certain embodiments, veltuzumab is administered as an intravenous infusion or a subcutaneous injection at a dose of 80 mg/m$^2$ once weekly for 4 weeks. In certain embodiments, veltuzumab is administered as an intravenous infusion or a subcutaneous injection at a dose of 120 mg/m$^2$ once weekly for 4 weeks. In certain embodiments, veltuzumab is administered as an intravenous infusion or a subcutaneous injection at a dose of 200 mg/m$^2$ once weekly for 4 weeks. In certain embodiments, veltuzumab is administered as an intravenous infusion or a subcutaneous injection at a dose of 375 mg/m$^2$ once weekly for 4 weeks.

In certain embodiments, the CD20 inhibitor used in combination with a compound of Formula (I), or an isotopic variant thereof; or a pharmaceutically acceptable salt, solvate, hydrate, or prodrug, is TRU-015. In certain embodiments, the methods described herein further comprise administering TRU-015 as an intravenous infusion in weekly cycles. In certain embodiments, TRU-015 is administered as an intravenous infusion for multiple weekly cycles. In certain embodiments, TRU-015 is administered at a dose between about 100 mg to about 1200 mg per week. In certain embodiments, TRU-015 is administered at a dose of about 400 mg per week. In certain embodiments, TRU-015 is administered at a dose of about 700 mg per week. In certain embodiments, TRU-015 is administered at a dose of about 1000 mg per week.

In certain embodiments, a CD20 inhibitor is administered once per day, twice per day, or three times per day. In certain embodiments, the CD20 inhibitor is administered once per day. In certain embodiments, the CD20 inhibitor is administered once per day, twice per day, or three times per day. In certain embodiments, the CD20 inhibitor is administered once per day. In certain embodiments, the CD20 inhibitor is co-administered (e.g., in a single dosage form), once per day.

In certain embodiments, the CD20 inhibitor is administered weekly. In certain embodiments, the CD20 inhibitor is administered once every two, three, four, or five weeks. In certain embodiments, the CD20 inhibitor is administered once every four weeks. In certain embodiments, the CD20 inhibitor is administered is 21 days cycles. In certain embodiments, the CD20 inhibitor is administered is 28 days cycles. In certain embodiments, the CD20 inhibitor is administered intravenously. In certain embodiments, the CD20 inhibitor is administered as an intravenous infusion. In certain embodiments, the CD20 inhibitor is administered subcutaneously.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Additional Combination Therapy

In certain embodiments, the methods of combination therapy comprising a compound of Formula (I), an isotopic variant thereof; or a pharmaceutically acceptable salt, solvate, hydrate, or prodrug thereof and a CD20 inhibitor can also be combined or used in combination with a third agent or therapies useful in the treatment, prevention, or amelioration of one or more symptoms of a proliferative disorders, diseases, or conditions.

Suitable third agent of therapies include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and xirnelagatran, (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma monists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid secjuestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) famesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat, and (54) other miscellaneous agents, such as, hydroxyurea, procarbazine, mitotane, hexamethylmelamine, and gold compounds.

In certain embodiments, the third therapies that may be used in combination with the methods provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

In certain embodiments, the third therapeutic agents that may be used in combination with the compounds provided herein include, but are not limited to, alkylating drugs (mechlorethamine, chlorambucil, cyclophosphamide, melphalan, and ifosfamide), antimetabolites (cytarabine (also known as cytosine arabinoside or Ara-C), and methotrexate), purine antagonists and pyrimidine antagonists (6-mercaptopurine, 5-fluorouracil, cytarbine, and gemcitabine), spindle poisons (vinblastine, vincristine, and vinorelbine), podophyllotoxins (etoposide, irinotecan, and topotecan), antibiotics (daunorubicin, doxorubicin, bleomycin, and mitomycin), nitrosoureas (carmustine and lomustine), enzymes (asparaginasc), and hormones (tamoxifen, leuprolide, flutamide, and megestrol), imatinib, adriamycin, dexamethasone, and cyclophosphamide.

In another embodiment, the method provided herein comprises administration of a compound of Formula (I), or an isotopic variant thereof, or a pharmaceutically acceptable salt, solvate, hydrate, or prodrug thereof and a CD20 inhibitor, together with administering one or more chemotherapeutic agents and/or therapies selected from: alkylation agents (e.g., cisplatin, carboplatin); antimetabolites (e.g., methotrexate and 5-FU); antitumor antibiotics (e.g., adriamymycin and bleomycin); antitumour vegetable alkaloids (e.g., taxol and etoposide); antitumor hormones (e.g., dexamethasone and tamoxifen); antitumour immunological agents (e.g., interferon α, β, and γ); radiation therapy; and surgery. In certain embodiments, the one or more chemotherapeutic agents and/or therapies are administered to the subject before, during, or after the administration of a compound of Formula (I), or an isotopic variant thereof, or a pharmaceutically acceptable salt, solvate, hydrate, or prodrug thereof and a CD20 inhibitor.

Such other agents, or drugs, can be administered, by a route and in an amount commonly used therefor, simultaneously or sequentially with a compound of Formula (I), or an isotopic variant thereof; or a pharmaceutically acceptable salt, solvate, hydrate, or prodrug thereof and a CD20 inhibitor. When a compound of Formula (I) and a CD20 inhibitor are used contemporaneously with one or more other drugs, a pharmaceutical composition containing such other drugs in addition to the compound of Formula (I), or an isotopic variant thereof; or a pharmaceutically acceptable salt, solvate, hydrate, or prodrug thereof and a CD20 inhibitor can be utilized, but is not required. Accordingly, the pharmaceutical compositions provided herein include those that also contain one or more other active ingredients or therapeutic agents, in addition to a compound of Formula (I).

Pharmaceutical Compositions and Routes of Administration

Provided herein is a pharmaceutical composition comprising a compound of Formula (I), a CD20 inhibitor and a pharmaceutically acceptable excipient, adjuvant, carrier, buffer, or stabilizer. In some embodiments, the compound of Formula (I) and a CD20 inhibitor are present in the same pharmaceutical composition. In some embodiments, the compound of Formula (I) and the CD20 inhibitor are in different pharmaceutical compositions.

In one embodiment, the pharmaceutical compositions are provided in a dosage form for oral administration, which comprise a compound provided herein, and one or more pharmaceutically acceptable excipients or carriers. The pharmaceutical compositions provided herein that are formulated for oral administration may be in tablet, capsule, powder, or liquid form. In some embodiments, a tablet comprises a solid carrier or an adjuvant. Liquid pharmaceutical compositions generally comprise a liquid carrier such as water, petroleum, animal or vegetable oils, mineral oil, or synthetic oil. Physiological saline solution, dextrose or other saccharide solution, or glycols such as ethylene glycol, propylene glycol, or polyethylene glycol may be included. In some embodiments, a capsule comprises a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. In some embodiments, preservatives, stabilizers, buffers, antioxidants, and/or other additives are included.

In yet another embodiment, the pharmaceutical compositions are provided in a dosage form for topical administration, which comprise a compound provided herein, and one or more pharmaceutically acceptable excipients or carriers.

The pharmaceutical compositions can also be formulated as modified release dosage forms, including delayed-, extended-, prolonged-, sustained-, pulsatile-, controlled-, accelerated-, fast-, targeted-, and programmed-release, and gastric retention dosage forms. These dosage forms can be prepared according to conventional methods and techniques known to those skilled in the art (see, Remington: The Science and Practice of Pharmacy, supra; Modified-Release Drug Delivery Technology, 2nd Edition, Rathbone et al., Eds., Marcel Dekker, Inc.: New York, N.Y., 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In certain embodiments, the pharmaceutical compositions provided herein further comprise one or more chemotherapeutic agents as defined herein.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate;

microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W. R. Grace Co., Baltimore, Md.) and CAB-0-SILO (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-0-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or poly-alkylene glycol, including, 1,2-dimetboxymethane, diglyme, triglyme, tetraglyme, polyethylene glycol-350-dimethyl ether, polyethylene glycol-550-dimcthyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice ofPharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungi static concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and metliacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, buty] rubber epichlorohydrin rubbers, ethylene/vinyl alcohol copolymer, ethylene/vinyl acetate/vinyl alcohol terpolymer, and ethylene/vinyloxyethanol copolymer.

Articles of Manufacture

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes one or more containers and a dosage form of a compound of Formula (I), or an isotopic variant thereof; or a pharmaceutically acceptable salt, solvate, hydrate, or prodrug thereof and a CD20 inhibitor.

In certain embodiments, the kit provided herein includes one or more containers and a dosage form of a compound of Formula (I), or an isotopic variant thereof; or a pharmaceutically acceptable salt, solvate, hydrate, or prodrug thereof and CD20 inhibitor. Kits provided herein can further include devices that are used to administer the active ingredients. Examples of such devices include, but are not limited to, syringes, needle-less injectors drip bags, patches, and inhalers.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL, (microliters); M (molar); mM (millimolar), µM (micro molar); eq. (equivalent); mmol (millimoles), Hz (Hertz), MHz (megahertz); hr or hrs (hour or hours); min (minutes); and MS (mass spectrometry).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated herein are intended to exemplify the applicable chemistry through the use of specific examples and are not indicative of the scope of the disclosure.

Syntheses of Compounds I-XVI are described in U.S. Pat. No. 9,056,852 B2, which is incorporated by reference for such disclosure.

Example 1

Study of a Combination of a PI3K Inhibitor and a CD20 Inhibitor in Patients with Relapsed-Refractory CLL or Richter's Transformation The purpose of this study is to evaluate the safety and effectiveness of Compound A35, A36, A68, or A70 (three does: 60 mg, 120 mg, and 150 mg/day) and rituximab, in patients with advanced CLL or Richter's Transformation.

| Condition | Intervention | Phase |
|---|---|---|
| Chronic Lymphocytic Leukemia | Drug: Compound A35, A36, A68, or A70<br>Biological: rituximab | Phase 1/Phase 2 |

Study Type: Interventional
Study Design: Intervention Model: Single Group Assignment
Masking: No masking
Primary Purpose: Treatment
  Primary Outcome Measures:
Determine Acceptable Adverse Events That Are Related to Treatment [Time Frame: 6 months of therapy]. To determine the incidence of adverse events, any potential abnormal laboratory results and any dose-limiting toxicities
  Secondary Outcome Measures:
Overall Response Rate [Time Frame: Up to 1 year]. The overall response rate (ORR) in patients with CLL and Richter's Transformation treated with a combination of Compound A35, A36, A68, or A70 and rituximab.

| Arms | Assigned Interventions |
|---|---|
| Experimental:<br>rituximab + Compound A35, A36, A68, or A70 rituximab - 375 mg/m² in the first cycle and 500 mg/m² in cycles 2-6, administered every 28 days<br>Compound A35, A36, A68, or A70 oral daily dose - 60 mg | Drug:<br>Compound A35, A36, A68, or A70<br>A once daily oral agent<br>Biological: rituximab<br>IV anti-CD20 monoclonal antibody |
| Experimental:<br>rituximab + Compound A35, A36, A68, or A70 rituximab - 375 mg/m² in the first cycle and 500 mg/m² in cycles 2-6, administered every 28 days<br>Compound A35, A36, A68, or A70 oral daily dose - 120 mg | Drug:<br>Compound A35, A36, A68, or A70<br>A once daily oral agent<br>Biological: rituximab<br>IV anti-CD20 monoclonal antibody |
| Experimental:<br>rituximab + Compound A35, A36, A68, or A70 rituximab - 375 mg/m² in the first cycle and 500 mg/m² in cycles 2-6, administered every 28 days<br>Compound A35, A36, A68, or A70 oral daily dose - 150 mg | Drug:<br>Compound A35, A36, A68, or A70<br>A once daily oral agent<br>Biological: rituximab<br>IV anti-CD20 monoclonal antibody |

Eligibility
Ages Eligible for Study: 18 Years and older (Adult, Senior)
Sexes Eligible for Study: All
Accepts Healthy Volunteers: No
Criteria
Inclusion Criteria:
Confirmed diagnosis of B-cell Chronic Lymphocytic Leukemia or Richter's Transformation
Refractory to or relapsed after at least 1 prior treatment regimen
Eastern Cooperative Oncology Group (ECOG) score of 0 to 2
Exclusion Criteria:
Any major surgery, chemotherapy or immunotherapy within the last 14 days
Known hepatitis B virus, hepatitis C virus or HIV infection
Active autoimmune disorder (with the exception of autoimmune hemolytic anemia or ITP)

Example 2

Study of a Combination of a PI3K Inhibitor and a CD20 Inhibitor in Patients with Relapsed B-Cell Non-Hodgkin's Lymphoma (NHL), Including Chronic Lymphocytic Leukemia (CLL)

The purpose of this study is to evaluate the safety and effectiveness of Compound A35 (single dose: 60 mg/day) and rituximab, in patients with relapsed B-cell malignancies.

| Condition | Intervention | Phase |
|---|---|---|
| Chronic Lymphocytic Leukemia (CLL)<br>Small Lymphocytic Lymphoma (SLL)<br>Follicular Lymphoma (FL)<br>Marginal Zone B Cell Lymphoma (MZL)<br>Diffuse Large B-cell Lymphoma (DLBCL)<br>High Grade Non-Hodgkin's Lymphoma | Drug: Compound A35<br>Biological: rituximab | Phase 1b |

Study Type: Interventional
Study Design: Intervention Model: Single Group Assignment
Masking: No masking
Primary Purpose: Treatment
  Primary Outcome Measures:
Determine Acceptable Adverse Events That Are Related to Treatment [Time Frame: 6 months of therapy]. To determine the incidence of adverse events, any potential abnormal laboratory results and any dose-limiting toxicities
Secondary Outcome Measures:
Efficacy of Compound A35 with Rituximab as assessed by Overall Response (OR) [Time Frame: 2 years]. The efficacy of Compound A35 with Rituximab will be determined by the overall response of subjects calculated as the percent of subjects achieving a complete remission (CR) or a complete remission with incomplete marrow recovery (CRi) or a partial response (PR) according to the International Workshop on Chronic Lymphocytic Leukemia (IWCLL).
Evaluate the PK of Compound A35 with Rituximab (AUC) [Time Frame: 2 years] Determined by the Area Under the Concentration time curve (AUC)
Evaluate the PK of Compound A35 with Rituximab (Cmax) [Time Frame: 2 years] Determined by Peak Plasma Concentration (Cmax)

| Arms | Assigned Interventions |
|---|---|
| Experimental: rituximab + Compound A35 rituximab - 375 mg/m², administered for a total of 8 doses in 6 months Compound A35 oral daily dose - 60 mg | Drug: Compound A35<br>A once daily oral agent<br>Biological: rituximab<br>IV anti-CD20 monoclonal antibody |

Eligibility
Ages Eligible for Study: 18 Years and older (Adult, Senior)
Sexes Eligible for Study: All
Accepts Healthy Volunteers: No
Criteria
Inclusion Criteria:
Diagnosis of relapsed/refractory CLL SLL or FL, MZL, DLBCL and high-grade B-cell lymphoma. Subjects must meet the following criteria for relapsed or refractory disease:

Relapsed disease: a subject who previously achieved a CR or PR, but demonstrated disease progression after a response duration of >6 months Refractory disease: a subject who demonstrated disease progression within 6 months of most recent therapy No prior therapy with PI3K6 inhibitors No prior therapy with Bruton tyrosine kinase (BTK) inhibitors unless the subject was intolerant of BTK therapy Subjects with CLL, SLL, FL, and MZL must have a failure of at least 1 prior systemic therapy and be considered by the investigator a candidate for therapy with a rituximab-based regimen; subjects with DLBCL and high-grade B-cell lymphoma must have a failure of at least 2 prior therapies.

QT-interval corrected according to Fridericia's formula (QTcF) ≤450 milliseconds (ms)

Left ventricular ejection fraction >50%

For subjects, except those with CLL, must have at least one bi-dimensionally measurable nodal lesion >1.5 cm, as defined by 2014 Lugano Classification (Cheson et al., J Clin Oncol 2014; 32(27):3059-68)

Willingness to participate in collection of pharmacokinetic samples

A negative serum pregnancy test within 14 days of study Day 0 for females of childbearing potential Exclusion Criteria:

Known histological transformation from CLL to an aggressive lymphoma

Uncontrolled autoimmune hemolytic anemia or immune thrombocytopenia

Subjects who have tested positive for hepatitis B surface antigen and/or hepatitis B core antibody Positive for hepatitis C virus antibody (HCV Ab) or human immunodeficiency virus (HIV) antibody Ongoing drug-induced pneumonitis History of clinically significant cardiovascular abnormalities Baseline Characterization Fifteen patients were enrolled. The demographics and disease characteristics are consistent with those of patients with relapsed B-cell NHL and CLL/SLL enrolled in other trials.

|  | FL N = 9 | DLBCL/ MZL/CLL N = 6 | Total N = 15 |
|---|---|---|---|
| Age in years, median (range) | 61 (38-81) | 71 (57-78) | 62 (38-78) |
| Men, N (%) | 7 (78%) | 2 (33%) | 9 (60%) |
| Number of prior therapies, median (range) | 3 (1-10) | 2 (1-3) | 2 (1-10) |
| Subjects with prior anti-CD20 therapy, N (%) | 9 (100%) | 5/5 (100%) * | 14/14 (100%) |
| Subjects with prior alkylating therapy, N (%) | 9 (100%) | 4/5 (80%) * | 13/14 (93%) |
| Subjects with lymph nodes ≥5 cm, N (%) | 3 (33%) | 4/5 (80%) * | 7/14 (50%) |

* Data not available in 1 patient with CLL recently enrolled in the study

Dosing Schedule for Compound A35

Dosing of Compound A35 is done on a continuous dosing schedule (CS) or an intermittent dosing schedule (IS). On an IS, patients take 60 mg administered once a day on 7 consecutive days followed by 21 days without therapy, with cycles repeated every 28 days. On a CS, patients take 60 mg/day for the entirety of a 28 day cycle. All patients are started on a CS dosing regimen. Patients who complete two cycles of CS are switched to the IS.

In all cases, the dosing of rituximab is 375 mg/m2, administered for a total of 8 doses in 6 months.

Results

On the CS of Compound A35, a response was reported in 7 of 10 patients (70%) with indolent non-Hodgkin's lymphoma (NHL), 9 patients with FL and 1 patient with MZL. Only 1 patient had disease progression and discontinued from the study. For the other 9 patients, the median follow-up is 5.4 months (range, 3.3-7.7 months). Compound A35 in combination with rituximab achieves a very high rate of response in patients.

A response was reported in 1 of 4 patients (25%) with DLBCL. The patient who achieved a disease response has been on study for 5.4 months and the other 3 patients were discontinued due to disease progression.

Switch to the IS after 2 Cycles on the CS 15 patients were treated with a regimen consisting of rituximab 375 mg/m$^2$×8 doses over 6 months and Compound A35 at 60 mg on the CS for 2 cycles then switching to the IS.

To date 10/15 patients have completed 2 cycles on the CS and were switched to the IS, and only 1/10 patients (10%) developed delayed immune-related toxicity with a median follow-up of 3.4 months (range, 1.5-5.7) on the IS.

Of the 8 patients who achieved a disease response after 2 cycles of therapy, none had disease progression on the IS, with a median follow-up of 5.2 months (range, 3.1-7.5) from enrollment.

Compound A35 in combination with rituximab achieves a very high rate of response in patients with relapsed indolent NHL and CLL/SLL. These responses appear durable. These results compare favorably to other treatment approaches in these disease. Preliminary data suggest that the IS appears to reduce the incidence of delayed onset immune toxicities without erosion in treatment efficacy.

What is claimed is:

1. A method for treating a hematological malignancy, comprising administering:
    (i) an effective amount of a compound of Formula (I);

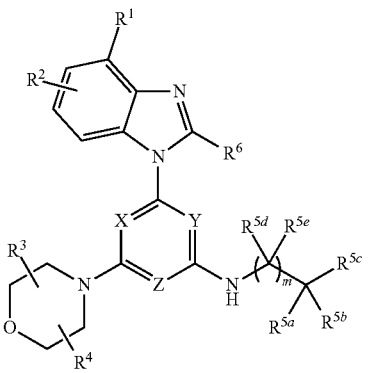

Formula (I)

or an enantiomer, a mixture of enantiomers, a mixture of two or more diastereomers, or an isotopic variant thereof; or a pharmaceutically acceptable salt, solvate, hydrate, or prodrug thereof; wherein:

X, Y, and Z are each independently N or CR$^X$, with the proviso that at least two of X, Y, and Z are nitrogen atoms; where R$^X$ is hydrogen or C$_{1-6}$ alkyl;

$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)$R^{1a}$, —C(O)O$R^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$ NR$^{1b}$R$^{1c}$, —S(O)R$^{1a}$, —S(O)$_2$R$^{1a}$, —S(C)NR$^{1b}$R$^{1c}$, or —S(O)$_2$NR$^{1b}$R$^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^{5a}$ is (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5b}$ is (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$ NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5c}$ is —(CR$^{5f}$R$^{5g}$)$_n$—(C$_{6-14}$ aryl) or —(CR$^{5f}$R$^{5g}$)$_n$-heteroaryl;

$R^{5d}$ and $R^{5e}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

$R^{5f}$ and $R^{5g}$ are each independently (a) hydrogen or halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$; or —S(O)$_2$NR$^{1b}$R$^{1c}$; or (d) when one occurrence of $R^{5f}$ and one occurrence of $R^{5g}$ are attached to the same carbon atom, the $R^{5f}$ and $R^{5g}$ together with the carbon atom to which they are attached form a $C_{3-10}$ cycloalkyl or heterocyclyl;

$R^6$ is hydrogen, $C_{1-6}$ alkyl, —S—$C_{1-6}$ alkyl, —S(O)—$C_{1-6}$ alkyl, or —SO$_2$—$C_{1-6}$ alkyl;

m is 0 or 1; and n is 0, 1, 2, 3, or 4;

wherein each alkyl, alkylene, heteroalkylene, alkenyl, alkenylene, heteroalkenylene, alkynyl, cycloalkyl, aryl, aralkyl, heteroaryl, and heterocyclyl in $R^1$, $R^2$, $R^3$, $R^4$, $R^6$, $R^X$, $R^{1a}$, $R^{1b}$, $R^{1c}$, $R^{1d}$, $R^{5a}$, $R^{5b}$, $R^{5c}$, $R^{5d}$, $R^{5e}$, $R^{5f}$, and $R^{5g}$ is optionally substituted with one, two, three, four, or five substituents Q, wherein each substituent Q is independently selected from (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one, two, three, or four, substituents $Q^a$; or (iii) $R^b$ and $R^c$ together with the N atom to which they are attached form heterocyclyl, which is further optionally substituted with one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl;

wherein two substituents Q that are adjacent to each other optionally form a $C_{3-10}$ cycloalkenyl, $C_{6-14}$ aryl, heteroaryl, or heterocyclyl, each optionally substituted with one, two, three, or four substituents $Q^a$; and (ii) an effective amount of a CD20 inhibitor to a patient in need thereof.

2. The method of claim 1, wherein $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

3. The method of claim 1, wherein $R^{5a}$ and $R^{5b}$ are each independently (a) halo; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$.

4. The method of claim 3, wherein $R^{5a}$ and $R^{5b}$ are each methyl, optionally substituted with one, two, or three halos.

5. The method of claim 4, wherein n is 1, m is 0, and $R^{5f}$ and $R^{5g}$ are each hydrogen.

6. The method of claim 1, wherein the compound of Formula (I) is of Formula (XI):

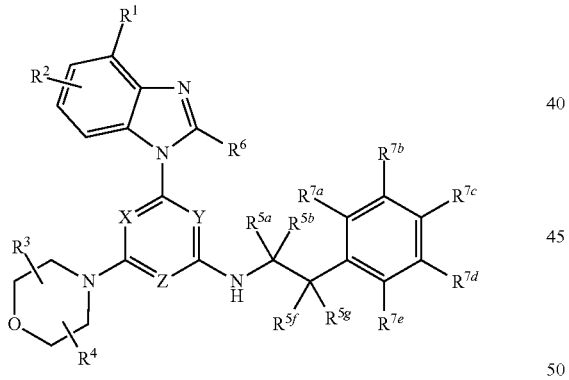

Formula (XI)

or an enantiomer, a mixture of enantiomers, a mixture of two or more diastereomers, or an isotopic variant thereof; or a pharmaceutically acceptable salt, solvate, hydrate, or prodrug thereof; wherein:

$R^{7a}$, $R^{7b}$, $R^{7c}$, $R^{7d}$, and $R^{7e}$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one, two, three, or four substituents $Q^a$; or (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, or —S(O)$_2$NR$^b$R$^c$; or two of $R^{7a}$, $R^{7b}$, $R^{7c}$, $R^{7d}$, and $R^{7e}$ that are adjacent to each other form $C_{3-10}$ cycloalkenyl, $C_{6-14}$ aryl, heteroaryl, or heterocyclyl, each optionally substituted with one, two, three, or four substituents $Q^a$.

7. The method of claim 1, wherein the compound of Formula (I) is selected from the group consisting of:

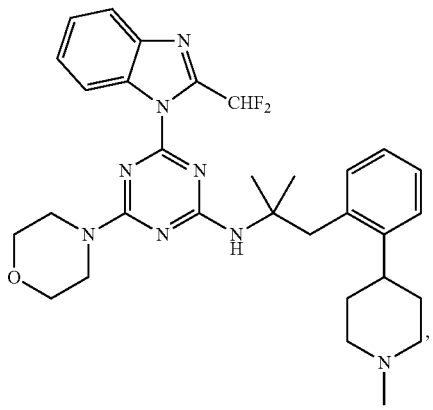

,

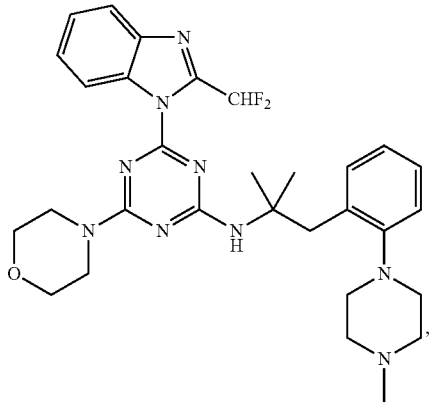

,

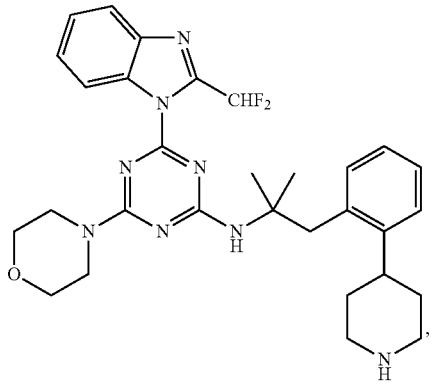

,

119
-continued
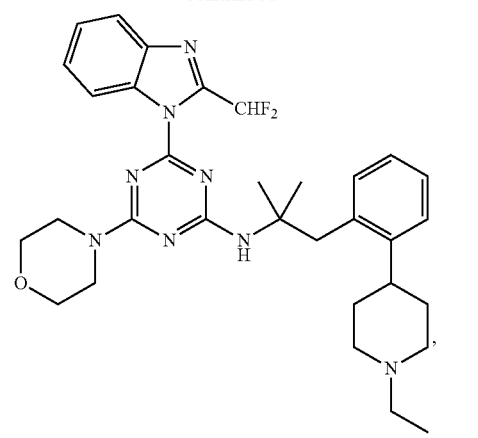
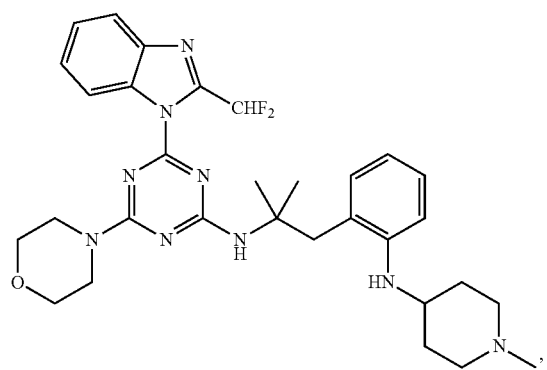
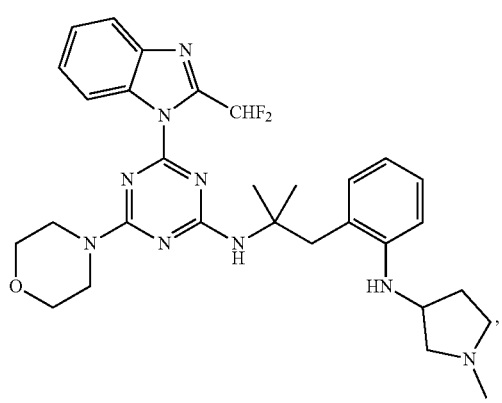
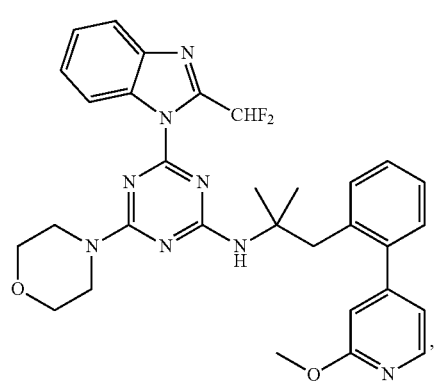
120
-continued
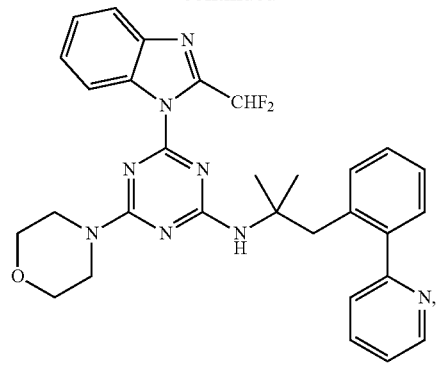
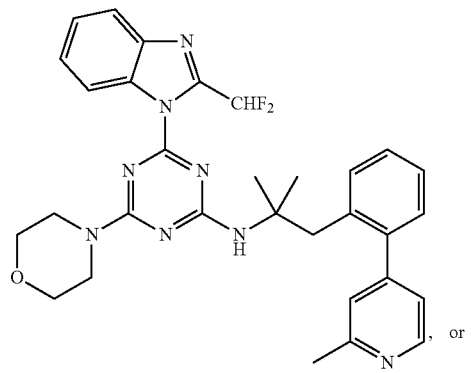
, or
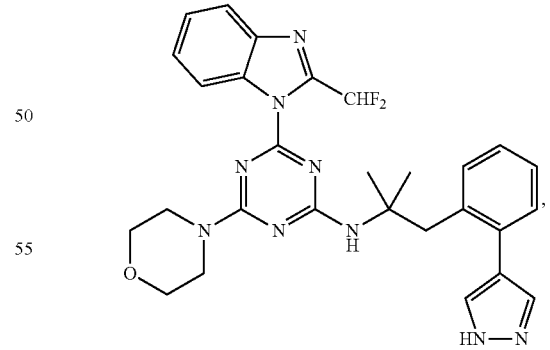
or an isotopic variant thereof, a pharmaceutically acceptable salt, solvate, hydrate, or prodrug thereof.
8. The method of claim 1, wherein the compound of Formula (I) is Compound A35:

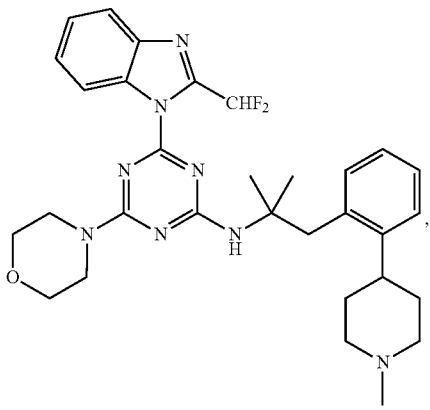

Compound A35 or an isotopic variant thereof, a pharmaceutically acceptable salt, solvate, hydrate, or prodrug thereof.

9. The method of claim 1, wherein the CD20 inhibitor is ofatumumab, obinutuzumab, rituximab, ocaratuzumab, ocrelizumab, tositumomab, ibritumomab tiuxetan, tisotumab vedotin, ublituximab, TRU-015, veltuzumab, BTCT4465A (RG7828), EDC9, MT-3724, or a variant or biosimilar thereof, or combinations thereof.

10. The method of claim 9, wherein the CD20 inhibitor is rituximab or a variant or biosimilar thereof.

11. The method of claim 1, wherein the hematological malignancy is a B-cell malignancy.

12. The method of claim 11, wherein the B-cell malignancy is selected from chronic lymphocytic leukemia (CLL), small lymphocytic lymphoma (SLL), follicular lymphoma (FL), marginal zone B cell lymphoma (MZL), diffuse large B-cell lymphoma (DLBCL), and high grade non-Hodgkin's lymphoma.

13. The method of claim 11, wherein the B-cell malignancy is selected from chronic lymphocytic leukemia (CLL), follicular lymphoma (FL), marginal zone B cell lymphoma (MZL), or diffuse large B-cell lymphoma (DLBCL).

14. The method of claim 1, wherein the cancer is relapsed B-cell non-Hodgkin's lymphoma (NHL) or chronic lymphocytic leukemia (CLL).

15. The method of claim 1, wherein about 60 mg/day of the compound of Formula (I), or an enantiomer, a mixture of enantiomers, a mixture of two or more diastereomers, or an isotopic variant thereof; or a pharmaceutically acceptable salt, solvate, hydrate, or prodrug thereof, is administered to the subject.

16. The method of claim 15, wherein the method comprises an intermittent dosing schedule (IS), comprising administering to subject the compound of Formula (I), or an enantiomer, a mixture of enantiomers, a mixture of two or more diastereomers, or an isotopic variant thereof; or a pharmaceutically acceptable salt, solvate, hydrate, or prodrug thereof once daily for 7 consecutive days followed by 21 days without treatment in a 28-day cycle.

17. The method of claim 7, further comprising administering an effective amount of cyclophosphamide, doxorubicin, vincristine, prednisolone, or a combination thereof.

18. The method of claim 17, wherein the hematological malignancy is diffuse large B-cell lymphoma (DLBCL) or follicular lymphoma (FL).

19. The method of claim 1, wherein the hematological malignancy is a relapsed or refractory B-cell malignancy.

* * * * *